US007801741B2

(12) United States Patent
Fracek, Jr. et al.

(10) Patent No.: US 7,801,741 B2
(45) Date of Patent: Sep. 21, 2010

(54) WEB LINKED DATABASE FOR TRACKING CLINICAL ACTIVITIES AND COMPETENCIES AND EVALUATION OF PROGRAM RESOURCES AND PROGRAM OUTCOMES

(75) Inventors: Stephen P. Fracek, Jr., Texas City, TX (US); Jon O. Nilsestuen, Friendswood, TX (US); Marilyn R. Childers, League City, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1693 days.

(21) Appl. No.: 10/817,385

(22) Filed: Apr. 2, 2004

(65) Prior Publication Data

US 2005/0015309 A1 Jan. 20, 2005

Related U.S. Application Data

(63) Continuation of application No. 09/731,367, filed on Dec. 6, 2000.

(60) Provisional application No. 60/169,175, filed on Dec. 6, 1999.

(51) Int. Cl.
*G06Q 10/00* (2006.01)
*G06Q 50/00* (2006.01)

(52) U.S. Cl. ........................................................ 705/2

(58) Field of Classification Search .................... 705/2, 705/4, 10; 235/375

See application file for complete search history.

(56) References Cited

U.S. PATENT DOCUMENTS

| | | | | |
|---|---|---|---|---|
| 5,616,899 | A * | 4/1997 | Recigno | 235/375 |
| 5,864,845 | A | 1/1999 | Voorhees et al. | |
| 5,864,846 | A | 1/1999 | Voorhees et al. | |
| 6,477,504 | B1 * | 11/2002 | Hamlin et al. | 705/10 |

OTHER PUBLICATIONS

"Microcomputer Management Information System for a University Allied Health Clinical Training Program" Kersting, Frank M. Dissertation for George Peabody College for Teachers of Vanderbilt University, Dec. 1983.*

Liaison Committee on Medical Education (LCME) "Overview" Jul. 22, 1997.*

Joint Commission on Accreditation of Hospitals (JCOAH) "A Journey Through the History of the Joint Commission" 1987.*

* cited by examiner

*Primary Examiner*—Gerald J. O'Connor
*Assistant Examiner*—John A Pauls
(74) *Attorney, Agent, or Firm*—Robert W Strozier

(57) ABSTRACT

A medical student and school program entry and/or medical professional entry, verification and tracking system is disclosed which is implemented on a computer with remote login and logoff capabilities. The system and methods utilizing the system includes login routines for medical students, medical staff, supervisors and accrediting agencies, medical discipline selection screens, protocol/procedure selection screens, data entry windows or areas associated with the protocol/procedure screens, logout routines, submission routines and polling routines.

9 Claims, 54 Drawing Sheets

| Clinical | RC Links |
| Respiratory Care Home Page | SAHS Home Page | UTMB Home Page |

For technical problems at this website, please send email to:
SAHS WebMaster

Please review disclaimer and Internet guidelines

1328

Respiratory Care

RC Student Time Clock Log In

Please enter the following information to complete you log record

I am — - Select Student - / - Select Student - / Name 1 / Name 2 / Name 3 / Name 4 / Name 5 / Name 6 / Name 7 / Name 8 / Name 9 (1422)

I am taking — - Select Courses - / - Select Courses - / COURSE 1 – Description 1 / COURSE 2 – Description 2 / COURSE 3 – Description 3 (1426, 1428)

Send Information (1430)   Clear Form (1432)

Respiratory Care

RC Student Time Clock Log Out

Hello Student Name, you logged in at 12:46:29 PM on Tuesday, June 8, 1999

The database will automatically record the log out hour and the data when you press the "Send Information" button. Please enter the following information to validate our daily time log:

1462

I was at: [Emergency Room ▼▲] — 1464

My Cl[ient] ...was [  st Name  ] (last name) — 1466

(first [  ] ) — 1468 Last Name

Dropdown options:
- Emergency Room
- Burn Unit
- Adult Floors
- Pediatric Floors
- Emergency Room
- PICU
- ISCU
- MICU
- SICU
- TDC-ICU
- Clinical Specialist
- THI-CS

[Send Information] — 1470  [Clear Form] — 1472

1460

Browser Banner

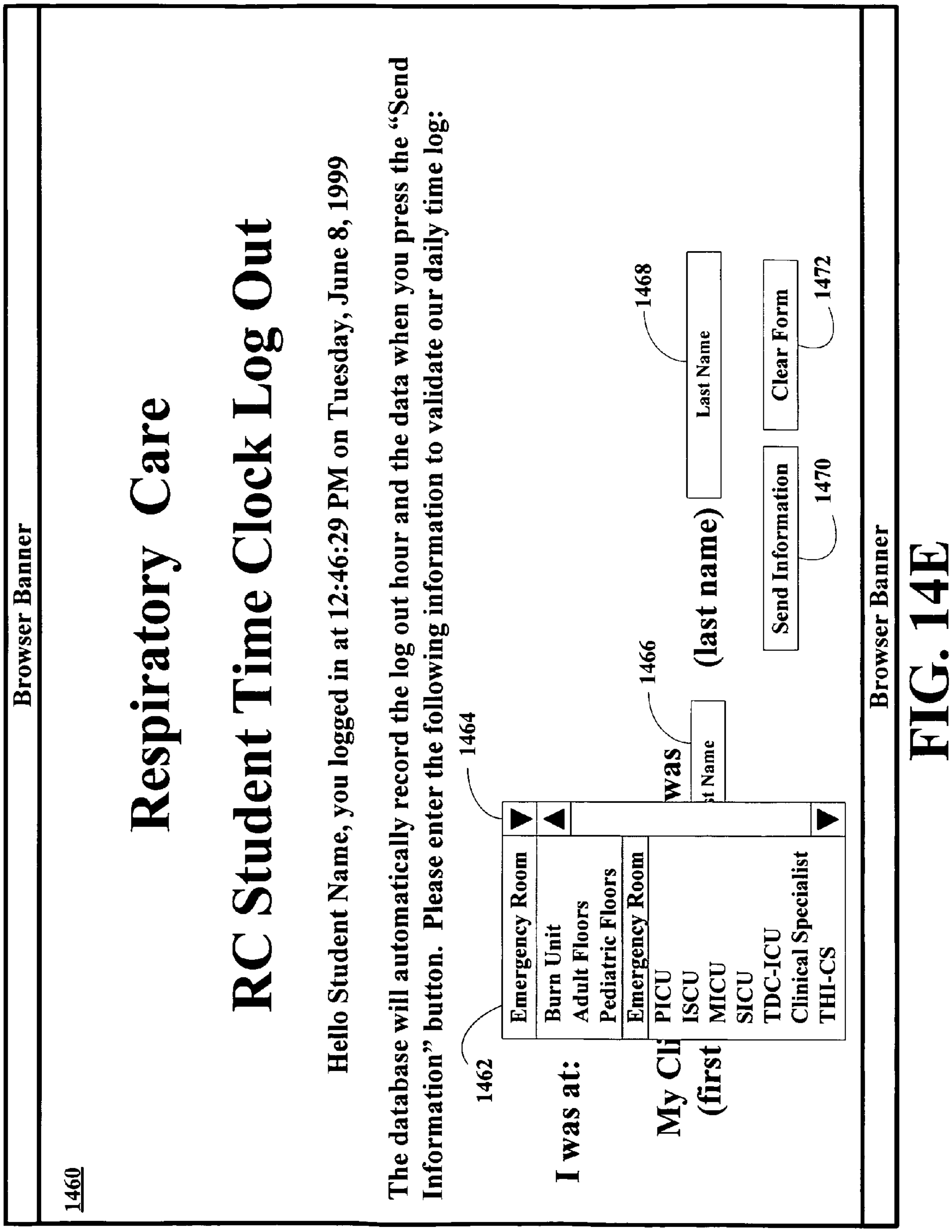

FIG. 14E

Browser Banner

1480

Respiratory Care

Student Name, thank you for filling out the time clock form. The following information has been reorded:

1482

| 1484<br>Time and<br>Date In: | 1485<br>3:37:19 PM<br>Thursday, July 8, 1999 | 1486<br>Course: | 1487<br>COURSE # - Course Description |
|---|---|---|---|
| 1488<br>Time and<br>Date Out: | 1489<br>3:40 PM<br>Thursday, July 8, 1999 | 1490<br>Location: | 1491<br>Adult Floors |
| 1492<br>Total Time:<br>(Hours) | 1493<br>.04 | 1494<br>Clinical Instructor: | 1495<br>Instructor Name |

1483

Please EXIT or QUIT the browser. The browser will retain your name and password until you exit or quit. DO NOT minimize the browser.

NOTE: If any of the above information is NOT correct please email us and tell us exactly what was incorrect so that we can adjust your time card and fix the database. Thank you.

Go to:

| Guest Book | Email | Video |

| General Info | Student Info | Courses | Continuing Ed | Databases | Clinical | RC Links |

| Respiratory Care Home Page | SAHS Home Page | UTMB Home Page |

Browser Banner

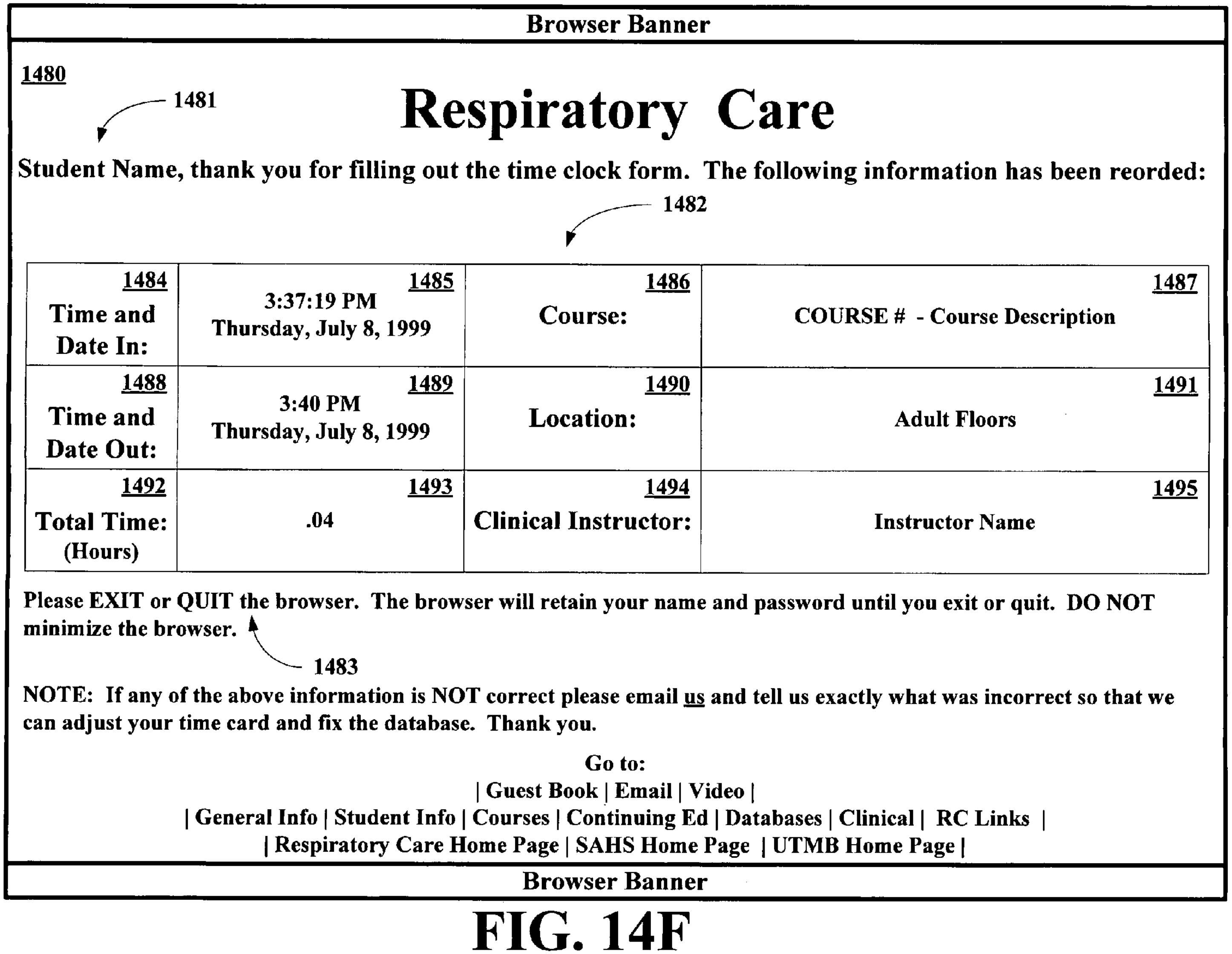

FIG. 14F

Respiratory Care

1532

Thank you, Clinical Instructor, for filling out the Adult Daily Log form for Student Name. Your time is greatly appreciated.

If you are done filling out Daily Log forms, please EXIT or QUIT the browser. The browser will retain you name and password until you exit or quit. Do NOT minimize browser.

Go to:
| Guest Book | Email | Video |
| General Info | Student Info | Courses | Continuing Ed | Databases | Clinical | RC Links |
| Respiratory Care Home Page | SAHS Home Page | UTMB Home Page |

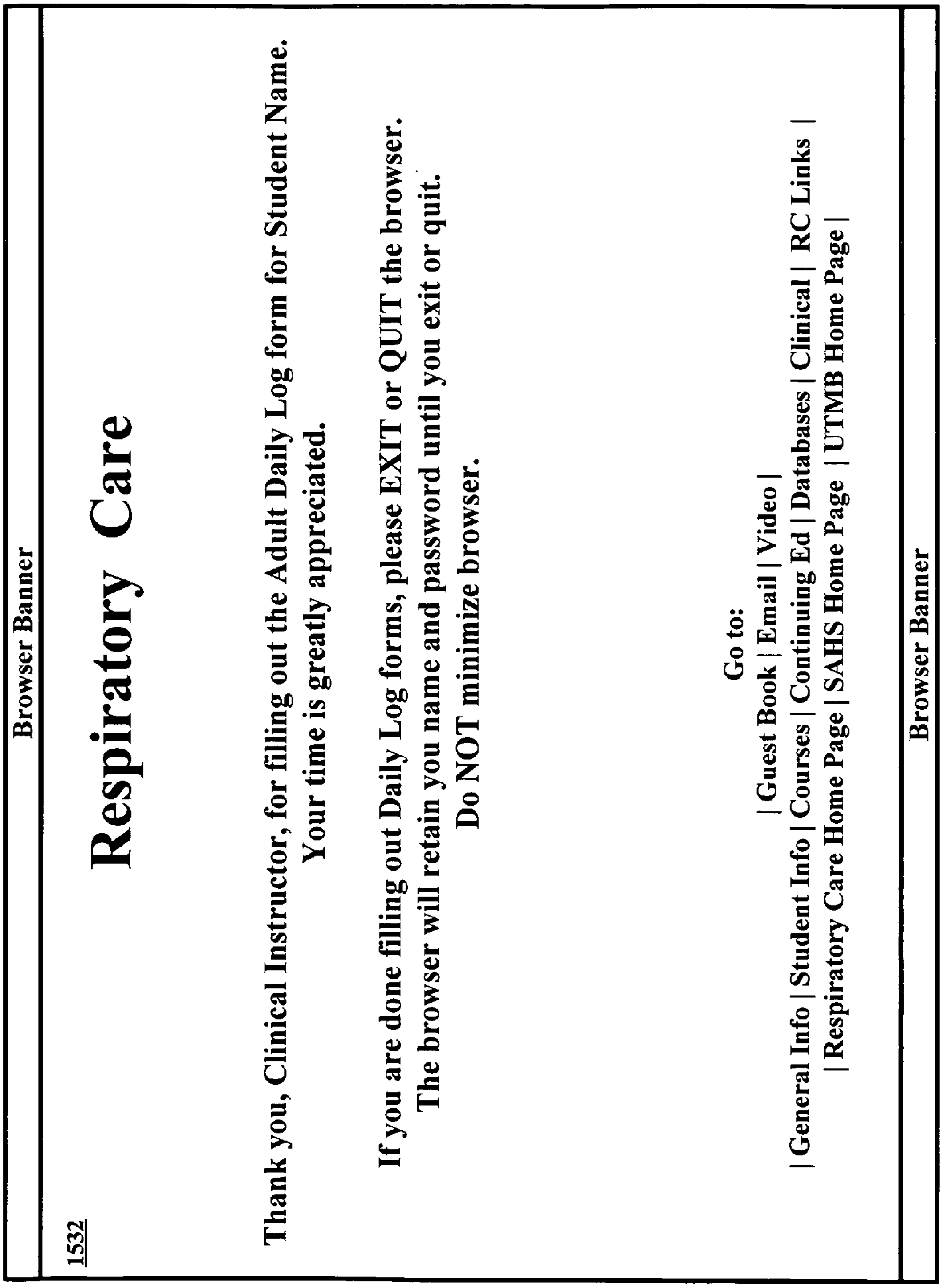

| Adult Critical Care Competencies | |
|---|---|
| Therapy Group | Special Competency |
| Manual Resuscitators | Setup & Ventilation via Endotracheal Tube |
| | Setup & Ventilation via Mask |
| Suction Procedure | ETS – Endotracheal Suctioning |
| | NTS – Nasotracheal Suctioning |
| | Tracheal Suctioning |
| | In-Line Suctioning |
| Endotracheal Tube / Tracheostomy Care | Securing Tracheostomy Tube |
| | Tracheostomy Care |
| | Cuff Management |
| | Intubation |
| Ventilatory Care | Ventiator Setup |
| | Routine Ventilator Check |
| | Ventilator Circuit Change |
| | Ventilator Graphics Analysis |
| | Capnography |
| Weaning from Mechanical Ventilation | Spontaneous Parameters |
| | Weaning Modes |
| Noninvasive Positive Pressure Ventilation | Noninvasive Ventilator Setup |
| | Noninvasive Ventilator Check |
| 1610 Patient Transport | Manual Ventilations during Transport |
| | Transport Ventilation Setup 1614 |

Adult Critical Care Competencies

| Therapy Group | Special Competency |
|---|---|
| Manual Resuscitators | BLS – Basic Life Support |
| | Hand Washing |
| | Isolation Procedures |
| | Charges |
| Patient Data | Vital Signs |
| | Chest Assessment |
| | Patient Assessment |
| | X-Ray Interpretation |
| | Isolation Procedures |
| Oxygen Therapy | Nasal Cannula |
| | Simple Mask |
| | Partial Rebreather |
| | Non-Rebreather |
| | Venti-Mask |
| | Pulse Oximetry |
| Aerosol & Humidity Therapy | Face Tent |
| | Face Mask |
| | Trach Collar |
| | T-Piece |
| | USN – Ultrasound Nebulizer |
| Aerosol & Drug Administration | MDI – Metered Dose Inhaler |
| | SVN – Small Volume Nebulizer |
| Hyperinflation Therapy | IS – Incetive Spirometry |
| | IPPB – Intermittent Positive Pressure Breathing |
| Bronchial Hygiene | Chest Physiotherapy |
| | Coughing |
| | Breathing Exercises |
| 1622 | Muscous Clearance Adjunts |
| | (PEP – Positive Expiratory Pressure, 1626 |

Respiratory Care

Adult Floor Therapy – Oxygen Therapy – Nasal Cannula
1634

REQUIRED: This evaluation was done (date): [06/07/99]   Enter date as m/d/y, for example 12/25/98 for December 25, 1998. If you leave the year space blank and enter 12/25, the program will automatically fill in the current year.

REQUIRED: Instructor
- Select Instructor -
- Select Instructor -
Instructor #1
Instructor #2
Instructor #3
Instructor #4
Instructor #5
Instructor #6
Instructor #7
Instructor #8
Instructor #9
Instructor #10
Instructor #11

1636  1638  1640

REQUIRED: Student
- Select Student -
- Select Student -
Student #1
Student #2
Student #3
Student #4
Student #5
Student #6
Student #7
Student #8
Student #9
Student #10
Student #11

1642  1644

Conditions (describe):

1460

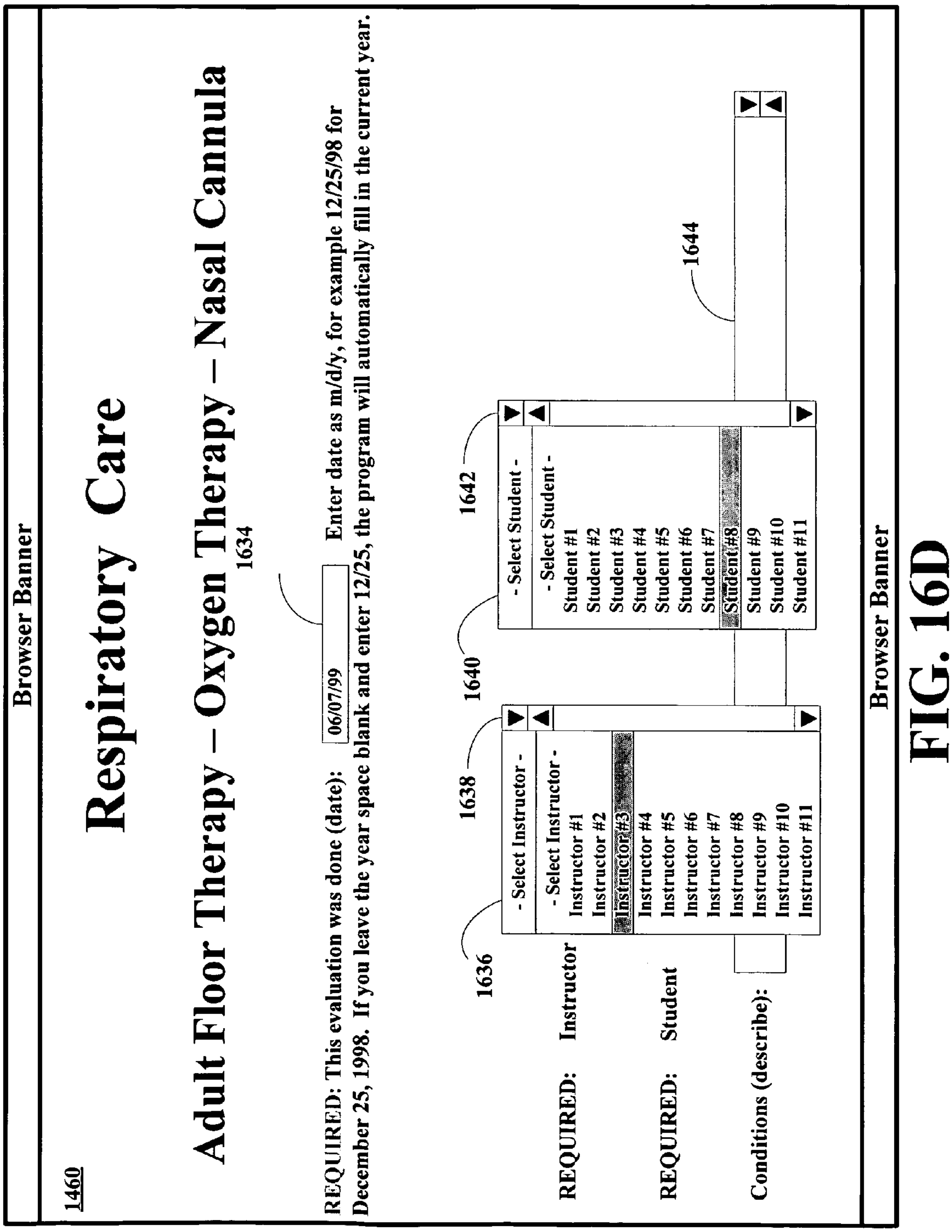

FIG. 16D

Additional comments: include errors of omission and commission, communicative skills, and effectiveness of patient interaction:

Student forgot to place the "NO SMOKING" sign. — 1646

Summary performance evaluation and recommendations

Please use the following criteria and select the appropriate pop-up menu.

- Satisfactory – student ready for minimally supervised application and refinement. Student performed without error or prompting, or able to self-correct, no critical errors.
- Unsatisfactory – prompting required; performed with critical errors, potentially harmful.
  - Minor – Unsatisfactory: Student requires re-evaluation after minor deficiencies are corrected.
  - Major – Unsatisfactory: Student requires complete re-evaluation.

REQUIRED: Summary Performance Evaluation:

- Select Evaluation - ▼   — 1652
 - Select Evaluation -
 Satisfactory
 Minor-Unsatisfactory
 Major-Unsatisfactory

1654

Send Information     Clear Form — 1650

1648

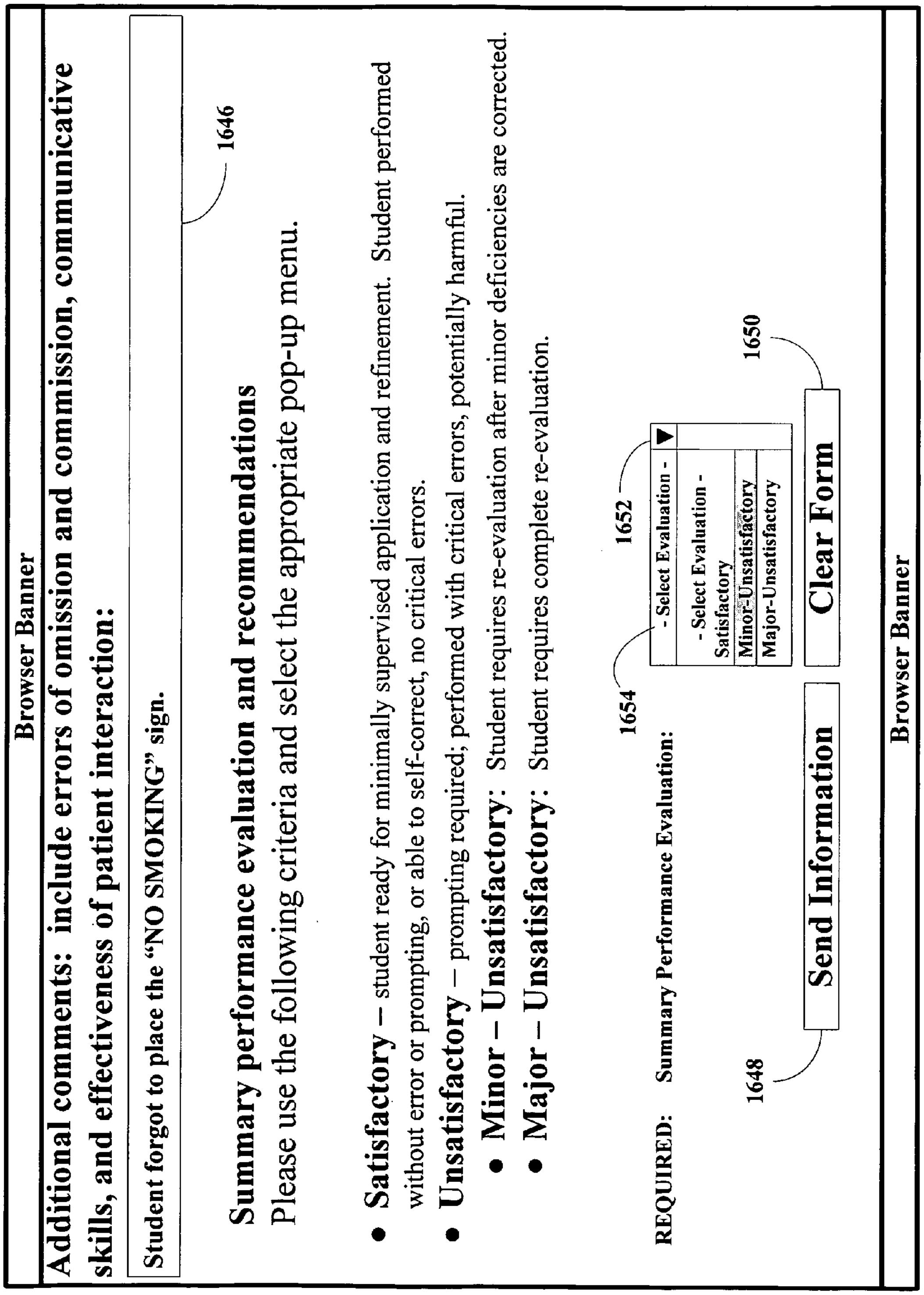

FIG. 16E

Browser Banner

Additional comments: include errors of omission and commission, communicative skills, and effectiveness of patient interaction:

Student forgot to place the "NO SMOKING" sign.

Summary performance Enter Network Password ▼ ...erformed

Please use the following  Please enter your authentication information    OK

...re corrected.

Cancel

- Satisfactory – student rea  Resource:   Database clinical competencies.fp3
  without error or prompting, or
- Unsatisfactory – prompti   User Name   User name
  - Minor – Unsatisfa           Password    *****
  - Major – Unsatisfa REQUIRED: Summary Performance Evaluation: Minor-Unsatisfactory ▼

Send Information    Clear Form

Browser Banner

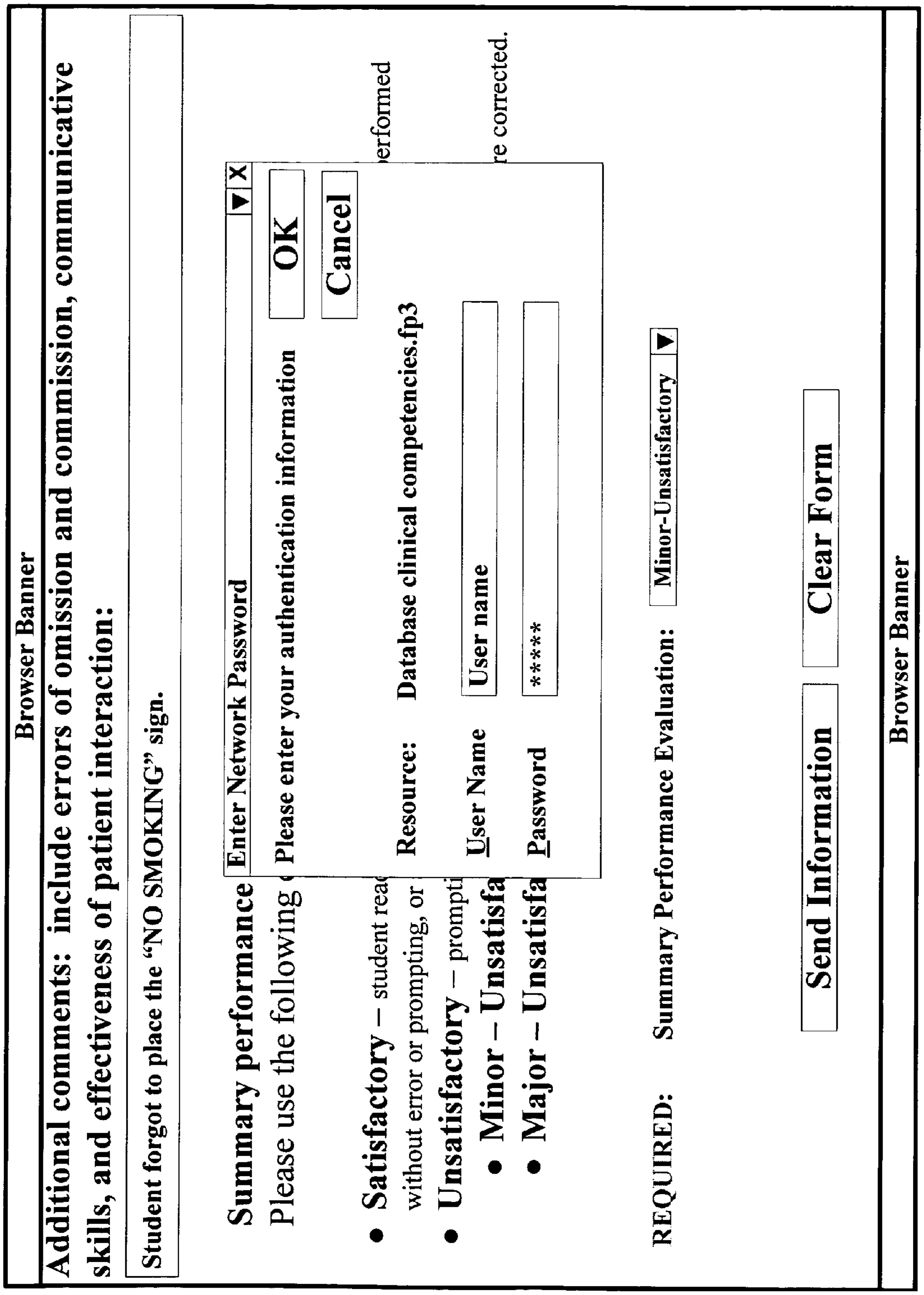

FIG. 16F

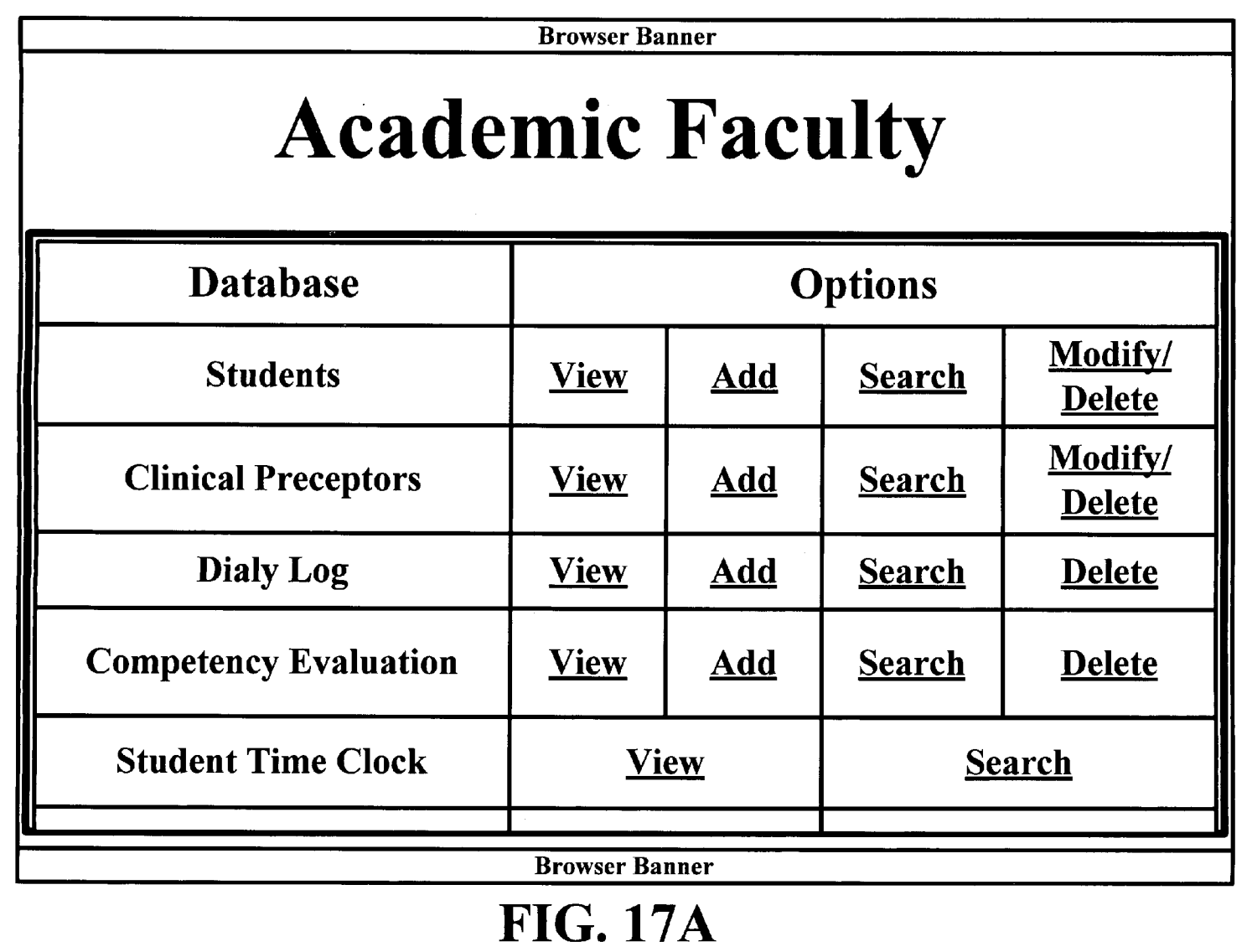

Browser Banner

Academic Faculty

| Database | Options | | | |
|---|---|---|---|---|
| Students | View | Add | Search | Modify/ Delete |
| Clinical Preceptors | View | Add | Search | Modify/ Delete |
| Dialy Log | View | Add | Search | Delete |
| Competency Evaluation | View | Add | Search | Delete |
| Student Time Clock | View | | Search | |

Browser Banner

FIG. 17A

Browser Banner

This form is used to modify or delete the record of Student Name
- To modify this record, make the necessary changes then client the MODIFY button.
- To delete this record client the DELETE button – WARNING – Deleted records can NOT be recovered!

First Name: [1721]
Last Name: [1722]
ID: [1723]
Email: [1724]
Address: [1725]
City: [1726]
State – (two letters): [ ] 1727
Zip Code: [1728]
Phone Number: [1729]

Browser Banner

The students in this Respiratory Care Program are:
Student 1
Student 2
Student 3
Student 4
Student 5
Student 6
Student 7
Student 8
Student 9
Student 10
Student 11

1730

1732

[MODIFY] 1731   [DELETE]   [Reset Form] 1733

Browser Banner

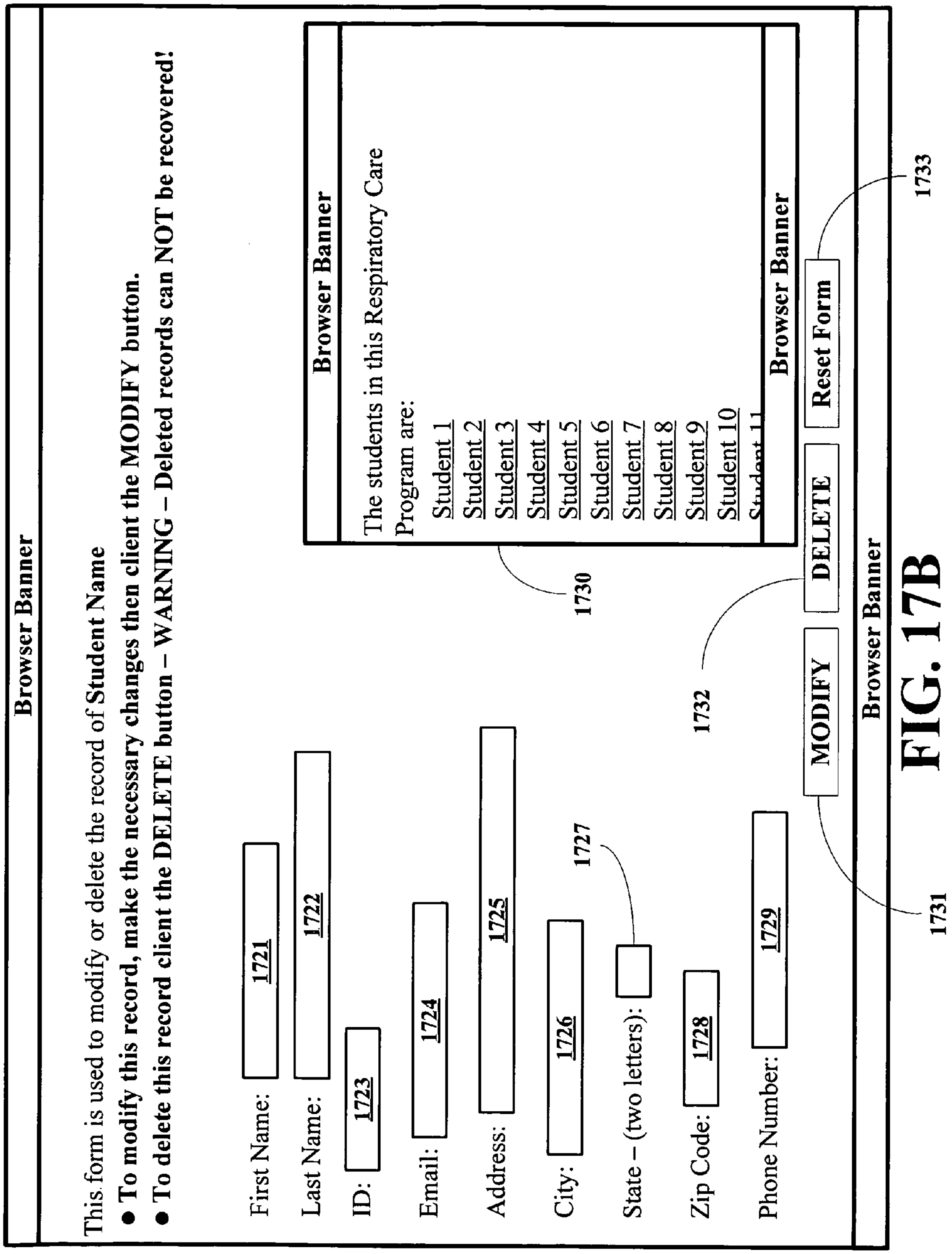

FIG. 17B

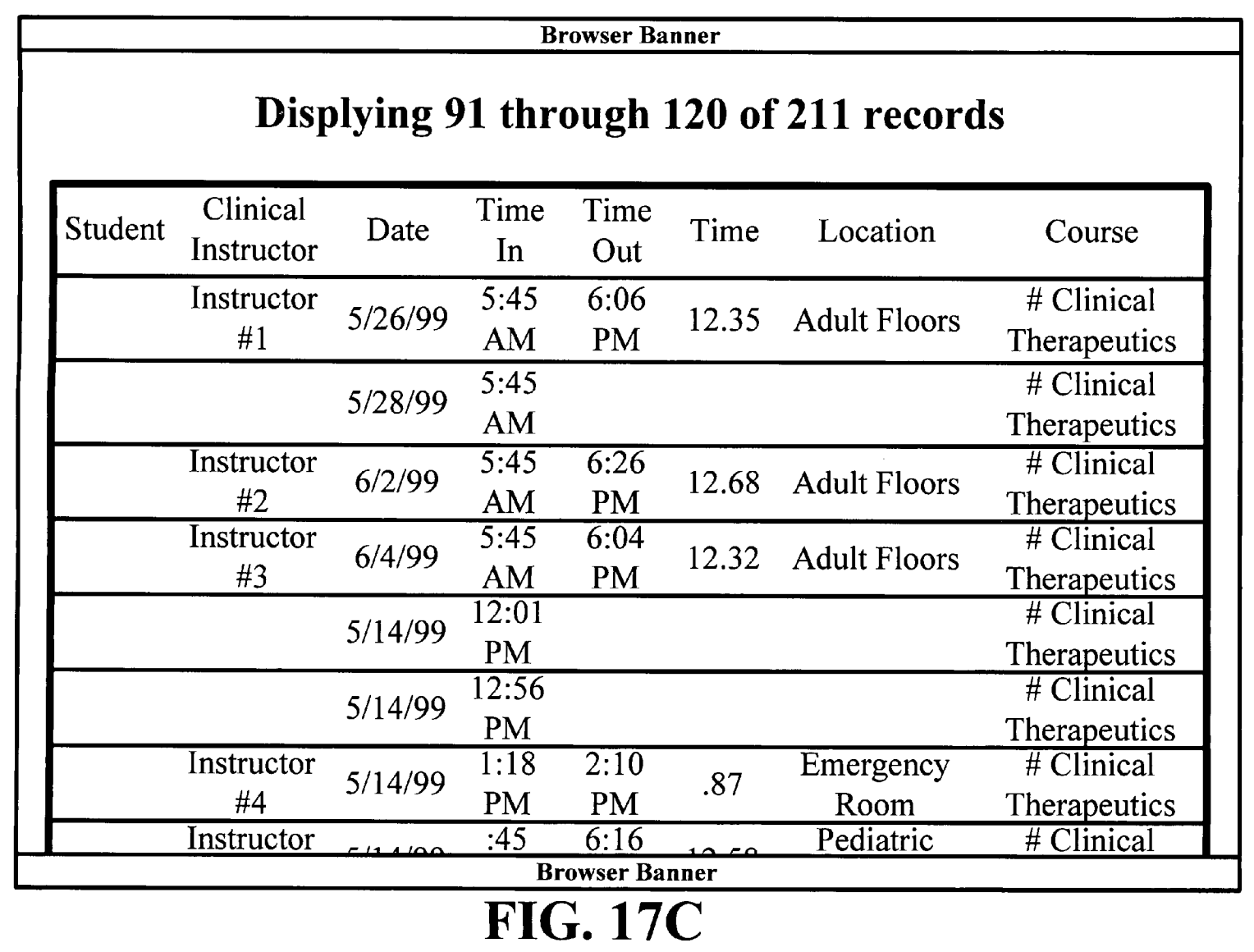

Browser Banner

Displying 91 through 120 of 211 records

| Student | Clinical Instructor | Date | Time In | Time Out | Time | Location | Course |
|---|---|---|---|---|---|---|---|
| | Instructor #1 | 5/26/99 | 5:45 AM | 6:06 PM | 12.35 | Adult Floors | # Clinical Therapeutics |
| | | 5/28/99 | 5:45 AM | | | | # Clinical Therapeutics |
| | Instructor #2 | 6/2/99 | 5:45 AM | 6:26 PM | 12.68 | Adult Floors | # Clinical Therapeutics |
| | Instructor #3 | 6/4/99 | 5:45 AM | 6:04 PM | 12.32 | Adult Floors | # Clinical Therapeutics |
| | | 5/14/99 | 12:01 PM | | | | # Clinical Therapeutics |
| | | 5/14/99 | 12:56 PM | | | | # Clinical Therapeutics |
| | Instructor #4 | 5/14/99 | 1:18 PM | 2:10 PM | .87 | Emergency Room | # Clinical Therapeutics |
| | Instructor | [illegible] | :45 | 6:16 | [illegible] | Pediatric | # Clinical |

Browser Banner

FIG. 17C

Respiratory Care

This form is used to search the Student Clinical Time Clock Record List

List <u>All Records</u> in the Student Clinical Time Clock Record List

To find Specific Records, enter the appropriate information in the following list.

- Student's Name: [Student Name ▼] — 1751, 1752
- Clinical Instructor's Last Name: [Instructor's Last Name ▼] — 1753, 1754
  [_____] — 1755, 1756, 1757
- Date: on or after this date [10/01/99] — 1758, 1759
- Location: [Location ▼] — 1760, 1761
- Course: [Course Number – Course Name ▼] — 1762

[Send Search Request]  [Clear Form] — 1763

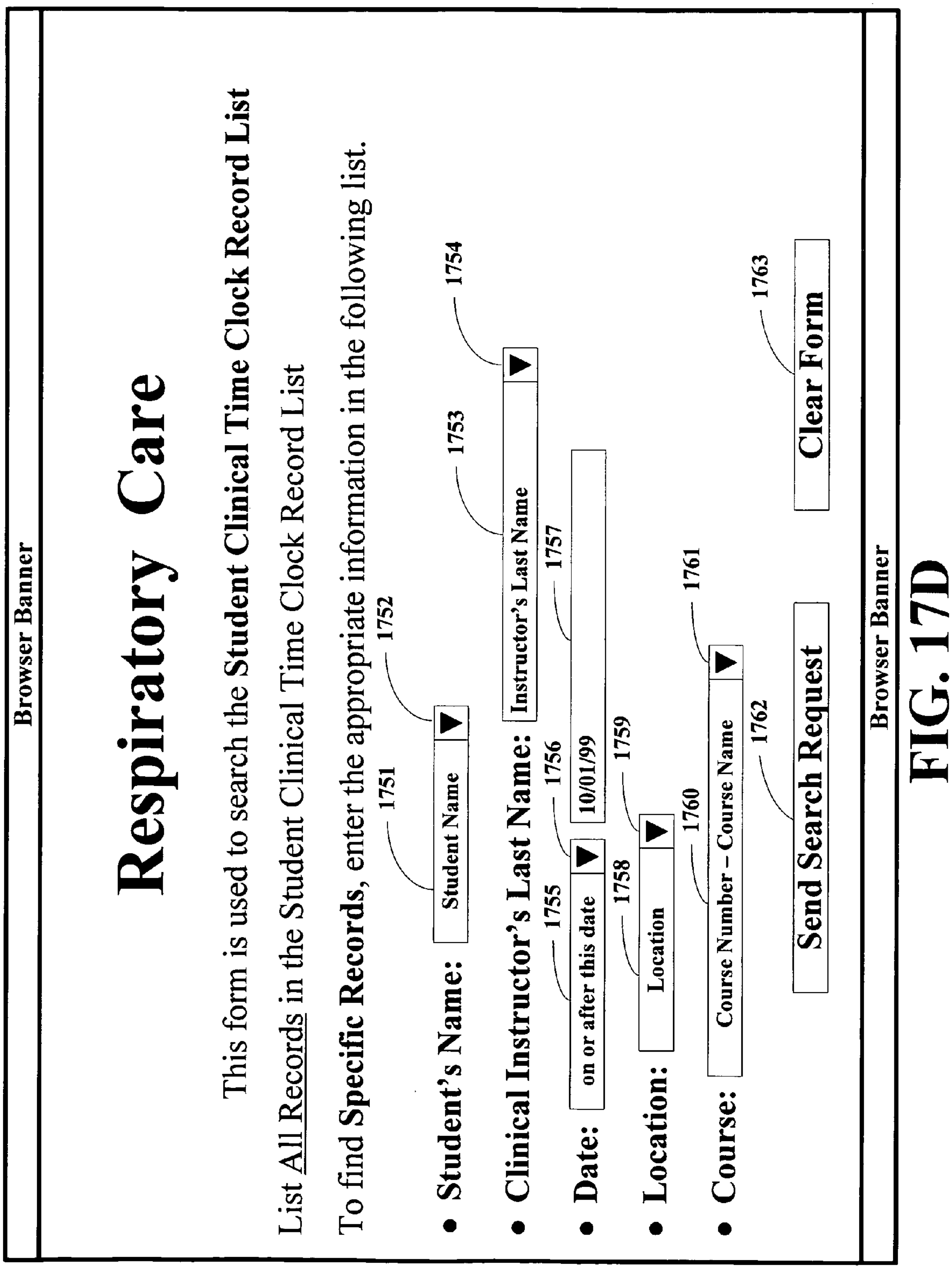

FIG. 17D

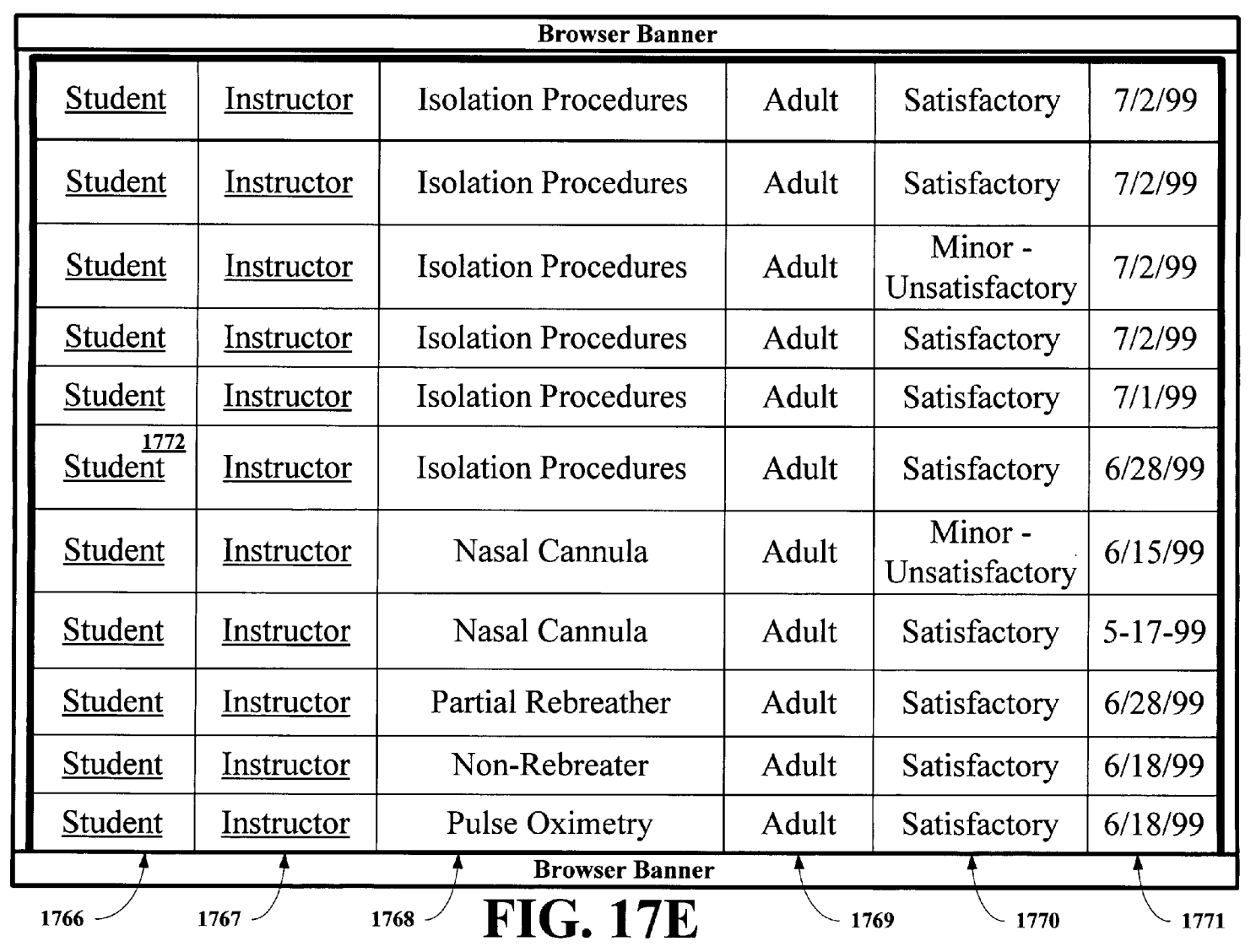

Browser Banner

| | | | | | |
|---|---|---|---|---|---|
| Student | Instructor | Isolation Procedures | Adult | Satisfactory | 7/2/99 |
| Student | Instructor | Isolation Procedures | Adult | Satisfactory | 7/2/99 |
| Student | Instructor | Isolation Procedures | Adult | Minor - Unsatisfactory | 7/2/99 |
| Student | Instructor | Isolation Procedures | Adult | Satisfactory | 7/2/99 |
| Student | Instructor | Isolation Procedures | Adult | Satisfactory | 7/1/99 |
| 1772 Student | Instructor | Isolation Procedures | Adult | Satisfactory | 6/28/99 |
| Student | Instructor | Nasal Cannula | Adult | Minor - Unsatisfactory | 6/15/99 |
| Student | Instructor | Nasal Cannula | Adult | Satisfactory | 5-17-99 |
| Student | Instructor | Partial Rebreather | Adult | Satisfactory | 6/28/99 |
| Student | Instructor | Non-Rebreater | Adult | Satisfactory | 6/18/99 |
| Student | Instructor | Pulse Oximetry | Adult | Satisfactory | 6/18/99 |

Browser Banner 1766 1767 1768 1769 1770 1771

FIG. 17E

Respiratory Care

Adult Floor Therapy – Oxygen Therapy – Nasal Cannula

1773

The database automatically recorded the following information (data is presented in blue, red, or yellow):

Student: Student Name
Competency: Nasal Cannula – Adult Floor Therapy
Time and Date: 11:58:57 AM – Tuesday, June 15, 1999

Conditions: This is a test

Equipment: This is still a test. Under "Equipment and Patient Preparation," item #6 is unsatisfactory and will generate an unsatisfactory – minor in the general summary.

NOTE: For the following questions the default selection is SATISFACTORY. The other selections are UNSATISFACTORY, NOT OBSERVED, and NOT APPLICABLE.

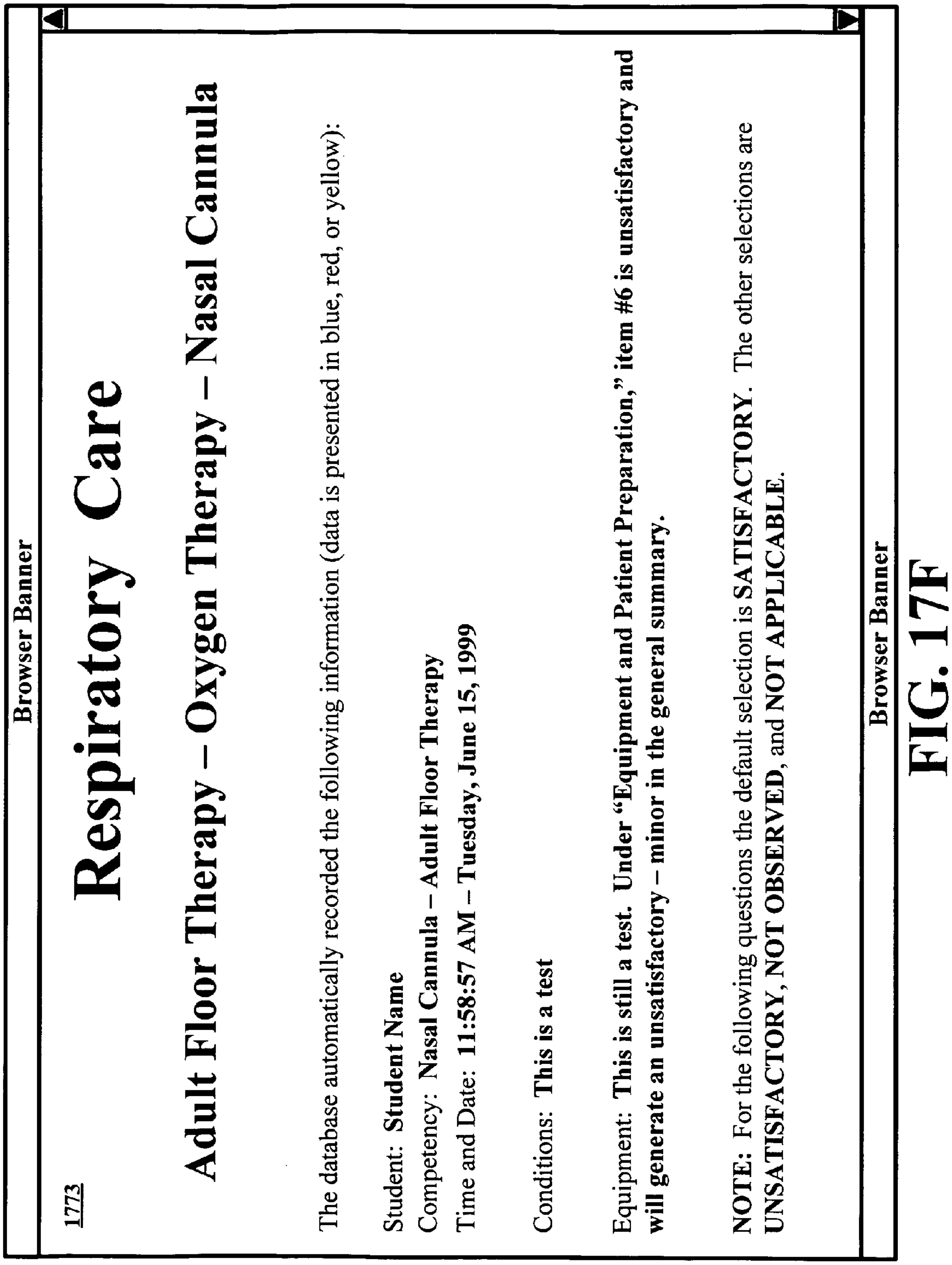

FIG. 17F

Browser Banner

1780     This form is used to search the Clinical Competency Database.

List All Records in the Clinical Competency Database
- Default Sort – sort the records using the default criteria (first by specific competency by order of appearance in the Unit Rotations (Hand Washing, BLS, Vital Signs, etc.), then ascending alphabetically by student's last name, then by patient by rank (adult, pediatric, neonatal), then by descending date, then ascending alphabetically by the instructor's last name.)
- Custom Sort    1781

To find Specific Records, enter the appropriate information in the following list.

- Student's Name:    - Select Student - ▼    1783   1784
- Preceptor' Name:    - Select Instructor - ▼    1785   1786
- Patient:    - Select Patient - ▼
- Date:    - Select Log Date - ▼    1788B   1787   1788A
- Summary:    - Select Summary - ▼
- Unit Rotation:    - Select Unit Rotation - ▼    1792   1791   1789   1790
- Therapy Groups:    - Select Therapy Group - ▼    1794   1793
- Specific Competency:    - Select Specific Competency - ▼    1796   1795

1797    Send Search Request    Clear Form    1798

Please specify the sort strategy. NOTE: the default sort strategy is preselected. To use the default sort strategy with the search criteria selected above, just click on the Search Request button. To modify the sort strategy, adjust the sort criteria and sort order to match your needs. Then click on the Send Search Request button.

Browser Banner

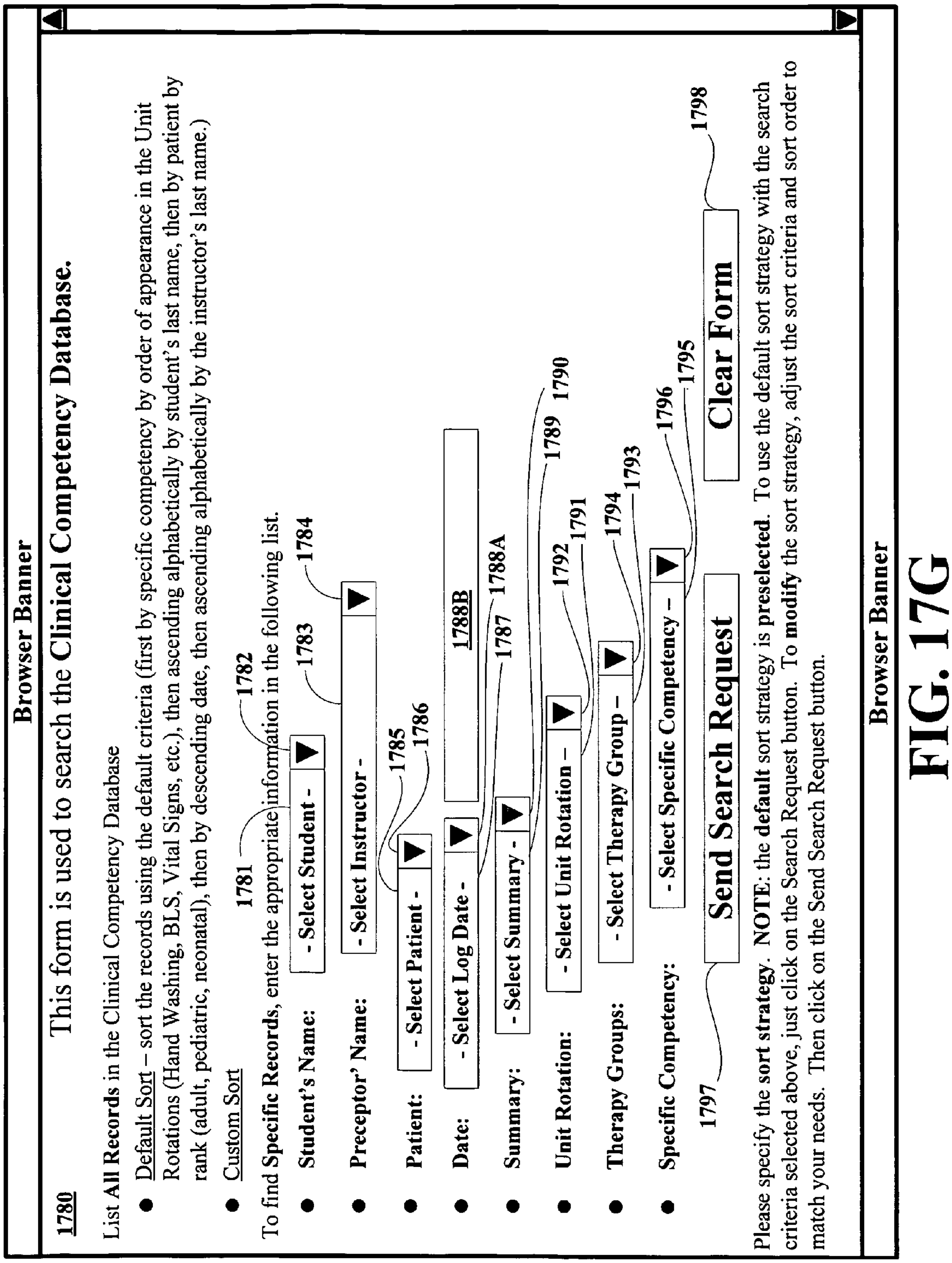

FIG. 17G

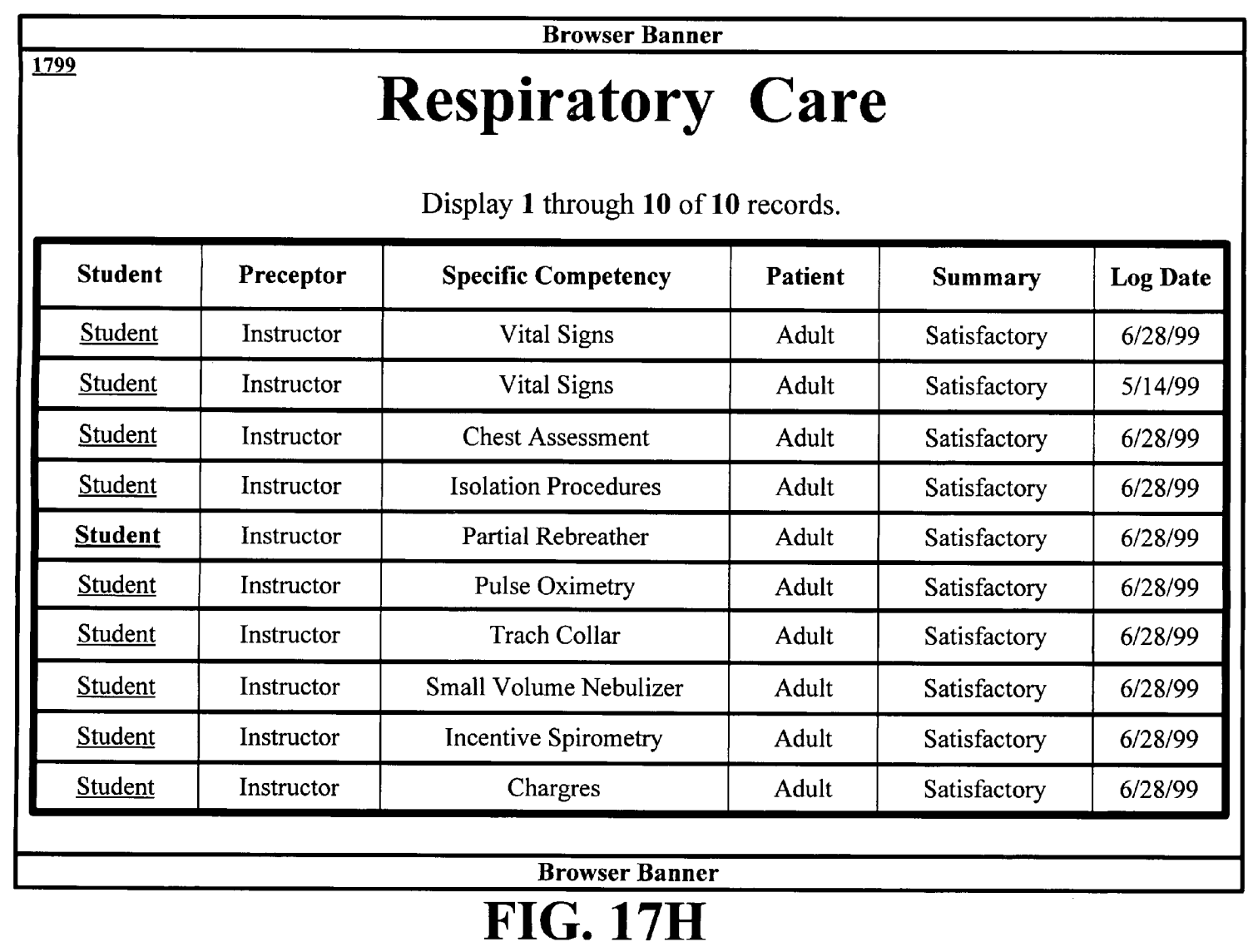

Browser Banner

1799

Respiratory Care

Display 1 through 10 of 10 records.

| Student | Preceptor | Specific Competency | Patient | Summary | Log Date |
|---|---|---|---|---|---|
| Student | Instructor | Vital Signs | Adult | Satisfactory | 6/28/99 |
| Student | Instructor | Vital Signs | Adult | Satisfactory | 5/14/99 |
| Student | Instructor | Chest Assessment | Adult | Satisfactory | 6/28/99 |
| Student | Instructor | Isolation Procedures | Adult | Satisfactory | 6/28/99 |
| Student | Instructor | Partial Rebreather | Adult | Satisfactory | 6/28/99 |
| Student | Instructor | Pulse Oximetry | Adult | Satisfactory | 6/28/99 |
| Student | Instructor | Trach Collar | Adult | Satisfactory | 6/28/99 |
| Student | Instructor | Small Volume Nebulizer | Adult | Satisfactory | 6/28/99 |
| Student | Instructor | Incentive Spirometry | Adult | Satisfactory | 6/28/99 |
| Student | Instructor | Chargres | Adult | Satisfactory | 6/28/99 |

Browser Banner

FIG. 17H

| PROCEDURES: | | OBSERVATIONS: | PERFORMANCES: | EVALUATIONS: |
|---|---|---|---|---|
| | | Patient Data | | |
| Vital Signs | 16 | | 8 | 2 |
| Chest Assessment | 15 | | 68 | 1 |
| Patient Assessments | 15 | | 56 | 1 |
| Isolation Procedures | 12 | | 60 | 1 |
| | | Oxygen Therapy | | |
| Nasal Cannula | 7 | | 34 | 1 |
| Simple Mask | 3 | | 25 | 1 |
| Venti-Maks | 4 | | 5 | |
| Partial Rebreather | | | 6 | 1 |
| Non-Rebreather | 1 | | 1 | 1 |
| Pulse Oximetry | 12 | | 11 | 1 |
| Cylinder Transport | 1 | | 58 | |

STUDENT PROGRAM RESOURCE SURVEY RESULTS

University of Texas Medical Branch – School of Allied Health Sciences – Department of Respiratory Care

CERTIFIED ELIGIBLE PROGRAM NUMBER: 10000
CERTIFIED ELIGIBLE PROGRAM NUMBER: 20000

*The purpose of this survey instrument is to evaluate our program resources. The data compiled will aid the program in an ongoing process of program improvement.*

This survey is for the Summer semester of 1999

INSTRUCTIONS: Consider each item separately and rate each item independently of all others. Select the rating that indicates the extent to which you agree with each statement. Please do not skip any rating. If you to not know about a particular area, please select Not Applicable.

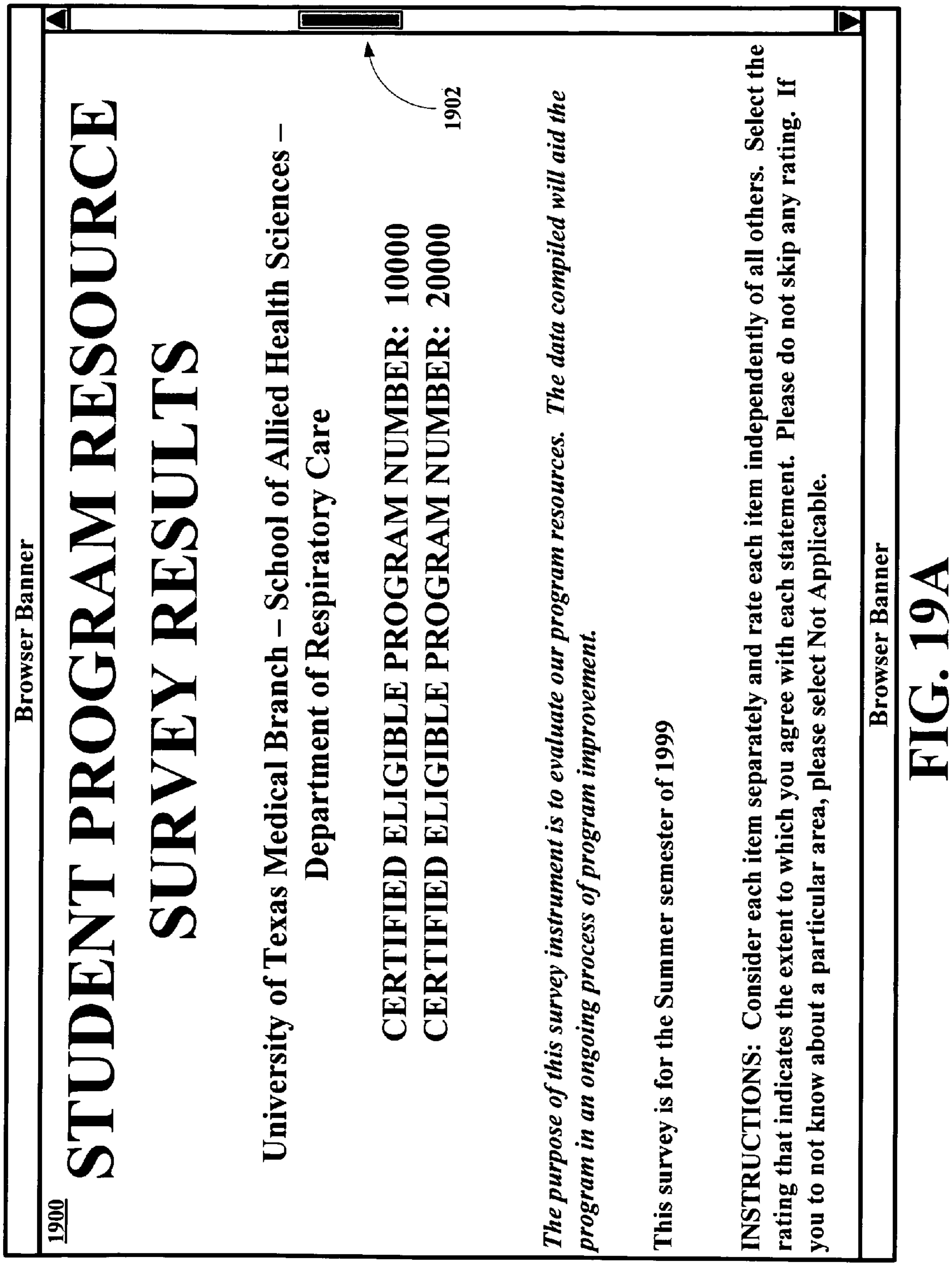

FIG. 19A

Respiratory Care

STUDENT PROGRAM RESOURCE SURVEY

University of Texas Medical Branch - School of Allied Health Sciences - Department of Respiratory Care CERTIFIED ELIGIBLE PROGRAM NUMBER: 100000
REGISTRY ELIGIB1LE PROGRAM NUMBER: 200000

*The purpose of this survey instrument is to evaluate our program resources. The data compiled will aid the program in an ongoing process of program improvement.*

I am a [Select ▼]. This Survey is for the [Select Semester ▼] semester of [Select Year ▼].

FIG. 20A

INSTRUCTIONS: Consider each item separately and rate each item independently of all others. Select the rating that indicates the extent to which you agree with each statement. Please do not skip any rating. If you do not know about a particular area, please select Not Applicable.

5 = Strongly Agree 4 = Generally Agree 3 = Neutral (acceptable)
2 = Generally Disagree 1 = Strongly Disagree NA = Not Applicable

I. PERSONNEL RESOURCES (PROGRAM FACULTY)

A. FACULTY TEACH EFFECTIVELY:

1. In the classroom ○ 5 ○ 4 ○ 3 ○ 2 ○ 1 ○ NA
2. In the laboratory ○ 5 ○ 4 ○ 3 ○ 2 ○ 1 ○ NA
3. In the clinical area ○ 5 ○ 4 ○ 3 ○ 2 ○ 1 ○ NA

B. FACULTY NUMBER IS ADEQUATE:

4. In the classroom ○ 5 ○ 4 ○ 3 ○ 2 ○ 1 ○ NA
5. In the laboratory ○ 5 ○ 4 ○ 3 ○ 2 ○ 1 ○ NA
6. In the clinical area ○ 5 ○ 4 ○ 3 ○ 2 ○ 1 ○ NA

C. FACULTY MEMBERS HAVE GOOD RAPPORT WITH STUDENTS. ○ 5 ○ 4 ○ 3 ○ 2 ○ 1 ○ NA

D. FACULTY MEMBERS ARE WILLING TO HELP STUDENTS WITH ACADEMIC NEEDS. ○ 5 ○ 4 ○ 3 ○ 2 ○ 1 ○ NA

E. FACULTY ENSURE STUDENT REPRESENTATION ON THE ADVISORY BOARD. ○ 5 ○ 4 ○ 3 ○ 2 ○ 1 ○ NA

Comments:

FIG. 20B

INSTRUCTIONS: Consider each item separately and rate each item independently of all others. Select the rating that indicates the extent to which you agree with each statement. Please do not skip any rating. If you do not know about a particular area, please select Not Applicable.

5 = Strongly Agree 4 = Generally Agree 3 = Neutral (acceptable)
2 = Generally Disagree 1 = Strongly Disagree NA = Not Applicable

II. PHYSICAL RESOURCES

A. INSTRUCTIONAL RESOURCES: CLASSROOMS

1. Are adequate in size. O5O4O3O2O1ONA
2. Have adequate lighting. O5O4O3O2O1ONA
3. Contain adequate seating. O5O4O3O2O1ONA
4. Have adequate ventilation. O5O4O3O2O1ONA
5. Are provided with appropriate equipment to support effective instruction. O5O4O3O2O1ONA

B. INSTRUCTIONAL RESOURCES: LABORATORY

1. Is adequate in size. O5O4O3O2O1ONA
2. Has adequate lighting. O5O4O3O2O1ONA
3. Has adequate seating. O5O4O3O2O1ONA
4. Is as adequate ventilation. O5O4O3O2O1ONA
5 Is equipped with the amount of equipment necessary for student performance of required laboratory exercises. O5O4O3O2O1ONA
6. Is equipped with the variety of equipment necessary for student performance of required laboratory exercises. O5O4O3O2O1ONA

FIG. 20C

7. Is equipped with the amount of supplies necessary for student performance of required laboratory exercises. O5O4O3O2O1ONA 8. Is equipped with the variety of supplies necessary for student performance of required laboratory exercises. O5O4O3O2O1ONA 9. Activities prepare the student to perform effectively in the clinical setting. O5O4O3O2O1ONA 10. Is accessible to students outside regularly scheduled class times. O5O4O3O2O1ONA Comments:

INSTRUCTIONS: Consider each item separately and rate each item independently of all others. Select the rating that indicates the extent to which you agree with each statement. Please do not skip any rating. If you do not know about a particular area, please select Not Applicable.

5 = Strongly Agree 4 = Generally Agree 3 = Neutral (acceptable)
2 = Generally Disagree 1 = Strongly Disagree NA = Not Applicable

III. LEARNING RESOURCES

A.LIBRARIES (SCHOOL AND AFFILIATES)

I. The program faculty and/or the library personnel, offer orientation and demonstration of the library services. O5O4O3O2O1ONA

FIG. 20D

2. The institutional library personnel provide assistance to the students when needed. O5O4O3O2O1ONA 3. The libraries provide sufficient materials to support classroom assignments. O5O4O3O2O1ONA 4. The library hours are convenient to student schedules. O5O4O3O2O1ONA 5. Program assignments require the use of library resources. O5O4O3O2O1ONA

B. STUDENT INSTRUCTIONAL SUPPORT SERVICES (TUTORS, COMPUTER LAB. ETC.)

1. Tutors provide assistance to the students when needed. O5O4O3O2O1ONA

2. Audiovisual and computer equipment are available to students for class assignments and activities. O5O4O3O2O1ONA 3. Computer resources are adequate to support the curriculum. O5O4O3O2O1ONA 4. Student Instructional Support Services are open an adequate number of hours. O5O4O3O2O1ONA Comments:

INSTRUCTIONS: Consider each item separately and rate each item independently of all others. Select the rating that indicates the extent to which you agree with each statement. Please do not skip any rating. If you do not know about a particular area, please select Not Applicable.

5 = Strongly Agree 4 = Generally Agree 3 = Neutral (acceptable)
2 = Generally Disagree 1 = Strongly Disagree NA = Not Applicable

FIG. 20E

IV. CLINICAL RESOURCES

A. CLINICAL ROTATIONS

1. Facilities a. The clinical facilities offer an adequate number of procedures for the student to meet clinical objectives. O5O4O3O2O1ONA b. The clinical facilities offer an adequate variety of procedures for the student to meet clinical objectives. O5O4O3O2O1ONA c. The clinical facilities provide a variety of current equipment. O5O4O3O2O1ONA 2. Experiences a. Each clinical rotation is of sufficient length to enable the student to complete clinical objectives. O5O4O3O2O1ONA b. Clinical rotations are sufficient to provide overall equivalent competencies for all students. O5O4O3O2O1ONA

B. CLINICAL INSTRUCTION

1. Students are adequately oriented to assigned clinical areas, and procedures. O5O4O3O2O1ONA 2. Clinical instructors are sufficiently knowledgeable to provide student instruction. O5O4O3O2O1ONA 3. Clinical instructors direct the students in completing the assigned objectives. O5O4O3O2O1ONA

FIG. 20F

4. Clinical instructors are consistent in their evaluation of student performance. O5O4O3O2O1ONA 5. Clinical instructors are readily available to assist students when needed. O5O4O3O2O1ONA Comments:

2012

INSTRUCTIONS: Consider each item separately and rate each item independently of all others. Select the rating that indicates the extent to which you agree with each statement. Please do not skip any rating. If you do not know about a particular area, please select Not Applicable.

5 = Strongly Agree 4 = Generally Agree 3 = Neutral (acceptable)
2 = Generally Disagree 1 = Strongly Disagree NA = Not Applicable

V. PHYSICIAN INTERACTION

A. Physician/student interaction facilitates the development of effective communication skills between physicians and students. O5O4O3O2O1ONA B. Physician contact is sufficient to provide the student with a physician perspective of patient care. O5O4O3O2O1ONA C. Overall student exposure to physicians ill the program is adequate. O5O4O3O2O1ONA Comments:

VI. ADDITIONAL COMMENTS

How long have you been a student in the program? [ ]

OVERALL RATING:
Please rate the OVERALL quality of the resources supporting the program. (Select one)

○ 5 = Excellent ○ 4 = Very Good ○ 3 = Good
○ 2 = Fair ○ 1 = Poor

Based on your experience, which program resources provided you with the most support?

[2012 ▼▲]

Why?

[2012 ▼▲]

Based on your experience, which program resources could be improved?

[2012 ▼▲]

How?

Please provide comments and suggestions that would help to improve the overall resources of the program.

▼
2012
▲

2014

2016

Thank You!

Go to:
| Guest Book | Email | Video |
| General Info | Student Info | Courses | Continuing Ed | Databases | Clinical
| RC Links |
| Respiratory Care Home Page | SAHS Home Page | UTMB Home Page |

WEB LINKED DATABASE FOR TRACKING CLINICAL ACTIVITIES AND COMPETENCIES AND EVALUATION OF PROGRAM RESOURCES AND PROGRAM OUTCOMES

RELATED APPLICATION

This application is a continuation of U.S. patent application Ser. No. 09/731,367 filed 6 Dec. 2000, which claims provisional priority to United States Provisional Patent Application Ser. No. 60/169,175 filed Dec. 6, 1999.

BACKGROUND OF THE INVENTION

1. Field of the Invention

The present invention relates to a program tracking and accreditation system and methods for using same.

More particularly, the present invention relates to a program tracking and accreditation system implemented on a distributed computer network such as the internet that tracks student personal educational data (e.g., addresses, telephone numbers, e-mail, exams scores, board scores, or any other relevant personnel information including career progress, internships, residences, specializations, etc.); allows medical students to track time spent at training sites and log training events, instructors to validate and certify student task completions and evaluate student competencies, supervisors to track and report/document student activities, and accreditation organizations to review medical school performance criteria and student training events remotely and methods for using same.

The system also accommodates performance and evaluation of medical staff in clinical settings. Supervisors can validate and certify medical staff competency for reporting to hospital accreditation agencies.

2. Description of the Related Art

Currently, medical student training and tracking and accreditation review and tracking is labor intensive and paper intensive. Records must then be collected and data entered to make the data accessible to computer tracking, report generation, and accreditation reviews.

Although, some systems exist to automate portions of this process, no system currently allows the unified data entry, validation and certification, tracking and accreditation of medical students and medical training facilities using a single database structure and a single interface to the database structure. Thus, there is a need in the art for a user friendly, server based system that allows medical students to directly enter their patient care data and/or laboratory training data, supervisors to directly track and verify student activities, medical schools to track student progress and performance in their programs and to evaluate program efficiency and effectiveness, and accreditation organizations to track student and school performance.

SUMMARY OF THE INVENTION

The present invention provides a system implemented on a computer, preferably a server connected to an intranet or internet, for entering, tracking and verifying medical student patient and procedure activity data where the entered data is databased for retrieval and review by instructors, supervisors, faculty members, program directors, medical school and/or accreditation agencies. The system includes a graphical users interface (GUI) subsystem for interacting with a user having screens designed to facilitate data entry, a database subsystem for storing, manipulating and polling data and a logon subsystem to log in to the database subsystem via the GUI subsystem and verifying user identity or establishing new user identities.

The present invention provides a method implemented on a computer, preferably a server connected to an intranet or internet, including the step of logging onto the system, selecting a medical discipline, selecting a medical protocol and/or procedure within the selected discipline, time stamping the selection, entering data associated with the protocol and/or procedure in appropriate fields in a GUI screen associated with the protocol and/or procedure, logging off of system after completion of the protocol data entry. The method can also include the step of submitting the protocol data to the database after review by a supervisor and polling entered data, where the submitting step can include changing a status of the entered data from a first state indicating initial data entry by a student and a second state indicating verification by an instructor. The submitting step can also include entering comments and levels of completion for student feed-back and/or protocol repeat or to repeat steps within the procedure.

The present invention also provides a method for automating an accreditation procedure including the steps of selecting an institution, retrieving protocol and/or procedure data, where the data evidences the protocol and/or procedures used by the institution to train and certify medical students. The method also includes the step of retrieving medical student data corresponding to each students performance on each protocol and/or procedure and comparing the protocol and student data to a standard to determine accreditation problems and/or deficiencies.

The present invention also provides a method for taking, storing and analyzing surveys used for the purpose of outcome evaluation, where faculty, students, graduates and employers or other related personnel may evaluate performance using standard evaluation instruments. Data acquisition protocols allow for immediate acquisition of statistical reports.

DESCRIPTION OF THE DRAWINGS

The invention can be better understood with reference to the following detailed description together with the appended illustrative drawings in which like elements are numbered the same:

FIG. 14A-F depict a preferred set of screen images associated with the student Time Clock functions—Time In and Time Out functions of this invention;

FIGS. 15A-D depicts a preferred set of screen images associated with the instructor daily log function of this invention;

FIGS. 16A-F depicts a preferred set of screen images associated with the clinical competencies function of this invention;

FIGS. 17A-H depicts a preferred set of screen images associated with the faculty subsystem of this invention;

FIGS. 20A-I depicts an example of a student program resource survey.

DETAILED DESCRIPTION OF THE INVENTION

Figure 1A:
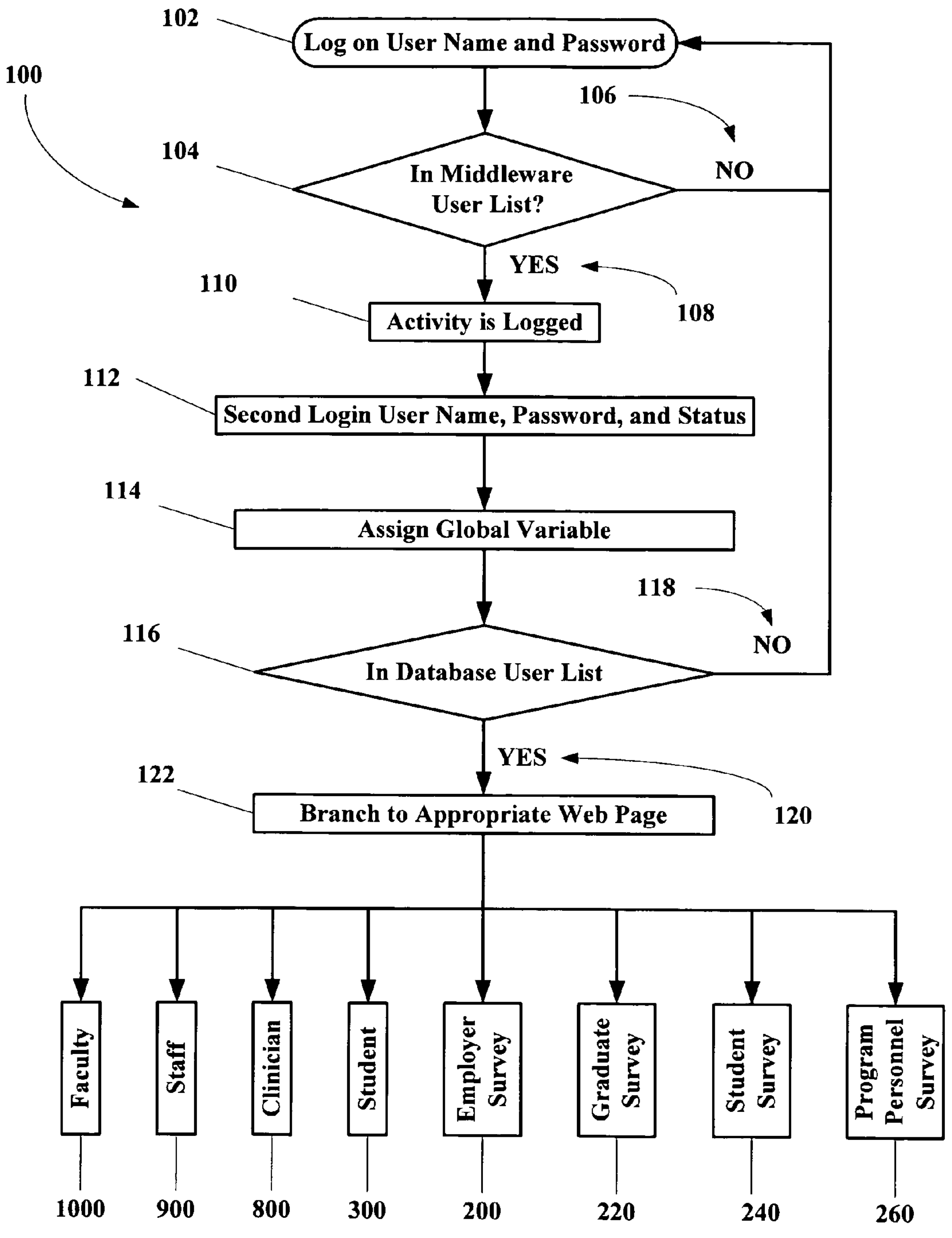
FIG. 1A depicts a block diagrams of a preferred embodiment of a start layout of the system of the present invention.

The inventors have found that an efficient and cost effective computer based system and methodology can be constructed that provides a uniform, single site computer based facility for entering, tracking, verifying and analyzing medical student and school performance on a set of standardized medical training protocols and/or procedures in a medical discipline. The system is designed to work with any medical or related health science discipline where students are certified according to a set of standardized training protocols and/or procedures. The system is preferably implemented on a single site server facility associated with an intranet or internet or other wide-band, distributed computer network which provides for remote entry by a large number of students, instructors, supervisors, faculty members and accreditation agency personnel, simultaneously.

The clinical database tracking system and program resource and outcomes evaluation system has been under development for some time. The clinical tracking system is used to replace the current voluminous paper system that programs are required to have in order to track student progress in learning clinical competencies. While students are in the clinic they can enter all of their therapeutic and diagnostic information and data into the computer, where it is recorded in a database subsystem. This allows the individual student and program faculty to have continuous and up to date information and data regarding the procedures the students have performed. In addition, all of the clinical evaluation forms are linked to the database subsystem in order to track how students are progressing in completing their competencies.

The program resource and outcomes evaluation system in an automated system that again allow students, program personnel, graduates and employers to enter evaluation information or data into a database subsystem via a global computer network such as the internet or intranet networks connecting a select set of computers. This allows for program faculty to automate the data collection process used for accreditation annual reports and self-study programs.

There are actually three products that are used via the internet. The first product is the time clock. The time clock tracks students' time during clinical rotations. When a student arrives at a clinical site, the student logs in to the system via the internet instead of a physical time clock, phone or pager system. The time clock function is password protected for each student and can be programmed to identify the computer being used to enter data. The time is acquired from an atomic time clock internet site such as a site in Denver, Colo. By utilizing this time clock function, students cannot alter their time of arrival or departure from a clinical site.

The second product is a clinical tracking database subsystem, which is capable of tracking student observations, performances and evaluations of clinical procedures. The old adage of "see one, do one, teach one" does not stand up in the legal system of this day and age. Therefore, if we can provide the clinical site with a system to document the number of times a student observes and performs a procedure we can help ensure that when the student is evaluated they have had to follow the necessary steps to prepare for the competency evaluation.

The third product is the program resource and outcomes evaluation system. This is an automated system that again allows students, program personnel, graduates and employers to enter evaluation information or data into a database subsystem via a global computer network such as the internet or intranet networks connecting a select set of computers. This allows for program faculty to automate the data collection process used for accreditation annual reports and self-study analysis and reports.

There are several benefits to this type of system: 1) program personnel have access to student data reports that display student progress in a concise format without having to weed through student notebooks and parse often difficult handwriting styles; 2) users have the capability for remote clinical sites to have direct access via the internet to the current forms being used by a medical field such as a respiratory care program; 3) finally, whenever the database is upgraded to reflect changes in the field of respiratory care (or other disciplines), the system is automatically upgraded for all programs using the system.

The time clock helps circumvent students abusing time entry and exit hours and keeps track of the number of hours students spend in clinical rotations. This data becomes useful when reporting clinical hours to state agencies or clinical sites.

The old system consisted of student generated paper forms with lots of observations and performance records, and required clinical faculty to spend countless hours tabulating the data. The present invention is an application of a database program that has the capability of generating reports and, thus, providing faculty with a precise and up to date picture of how students are progressing in completing their required clinical competencies.

The standardized forms will provide increased anonymity, increased response rates to surveys and automated analysis of the results.

Each of these programs will reduce the amount of paper generated by the current process, greatly reducing faculty time in developing reports, and convert data storage from hardcopy to digital format.

The streamlining really comes to fruition on the reporting end. It is much faster and easier to generate a report of student clinical hours when using the database generated report. The same is true for clinical observations, performance, evaluations and program surveys.

Currently, some of the clinical forms are still done via the old paper method due to lack of training of personnel in different departments. An example of this would be students rotating through the cardiac catheterization laboratory. In our institution students spend a day or two observing in this area and the clinical staff are not part of the respiratory care department. The time it would take to orient them to using the system and setting up login and passwords would not be worthwhile for such a short duration of clinical rotations.

Students had a half-day training session that simulated clinical rotations and completion of the computer based forms. Initially, clinical instructors were oriented individually or in group training sessions, subsequently the clinical database orientation system is performed during the new employee orientation process.

The system required user logon name and passwords specific to each student and clinical instructor for data entry. Data retrieval is currently linked to user logon status and access is restricted by middleware user protocol. For example, students can access only their own data and reports, while faculty can access all student data and view or generate individual or summative reports.

The major cost savings for the clinical database system comes from reduction in faculty hours in generating student clinical data reports. The program resource assessment and outcomes system reduces the man-hours needed to prepare survey packets and repeated mailings by using an internet based system. In addition, the major benefit is data reporting function that provides instant reports and automatic statistical analysis; and eliminates tallying the surveys generating data reports.

The present invention relates broadly to a system implemented on a computer and accessible over an intranet or internet, preferably a server connected to a intranet or internet, for entering, tracking, verifying, searching, certifying medical student patient and procedure activity data where the entered data is databased for retrieval and review by clinicians or instructors or supervisors, faculty members, program directors, medical school and/or accreditation agencies. The system includes a GUI subsystem for interacting with a user having screens designed to facilitate database interaction, data entry and display, a database subsystem for storing, manipulating and polling data and a logon subsystem to log in to the database subsystem via the GUI subsystem and verifying user identity or establishing new user identities.

The system can also include a middleware software program and routines for storing, manipulating and polling data and for performing most interactions with the database. The middleware allows the construction and storage of variables and variable list, certain statistics about variables such as means, median, standard deviations, or the like and allow for efficient and effective interaction with a rational database. The system also includes functions that allow students to login to the system, identify their instructors or clinicians, the medical discipline or area of training and the medical procedure for which the student is training. The student logs into the system, the system verifies the student status, the student can then time clock in which establishes a record with a time stamp for that student.

Once the student completes the task, rotation or assignment, the user selects a time out function that asks the student information about the clinician, hospital location and procedure. The system then enters the information into the database. The entry is then stored into the database in a non-validated state. A non-validated state means that the clinician or instructor has not reviewed the entry and certified or verified that the entry is accurate. The system also includes a daily log subsystem where a student can view daily log data, search for particular daily log data, add new daily log data into the database and generate summary reports. The system also includes a clinical competency subsystem where a student can view clinical competency data, search for particular clinical competency data, and generate summary reports. The system also allows the student to view and/or update the student's personal data.

The system also includes a clinician or instructor subsystem which allows the clinicians to validate student daily log and/or clinical competency data. The clinicians can also enter daily logs and enter comments about student daily log and/or competency data. The system also allows the clinicians to view and/or update their personal data.

The system also includes a staff subsystem that allows staff members to view, search, add, modify and/or delete records from the student and/or clinician entries.

The system also includes a summary or summary reports subsystem where time clock, daily log and/or clinical competency data can be searched, categorized, analyzed or manipulated to determine student activities, rankings, performance, timeliness or the like. The summary subsystem also allows faculty members to review student progress in the program, outcome variations between different training sites, and comparative evaluation of clinician/instructor performance. The data also allows faculty members to determine program deficiencies or other training inadequacies and to develop procedures to correct such deficiencies or inadequacies.

The system also includes a subsystem for performing surveys designed to allow users to comment on all aspects of the training program in a given institution or in all institutions in general.

Because all medical students have to be proficient in a standardized set of protocols and procedures, the system includes data entry forms for each such standardized protocol (protocols and procedures may be established by accreditation agencies or other regulatory agencies, or designed by individual institutions). Moreover, because the system is designed to store and track such data for all medical students having access to the system, the data can be analyzed for overall procedural and design errors in the standardized protocols or procedures.

The present invention also relates broadly to a method implemented on a computer, preferably a server connected to an intranet or internet, including the step of logging onto the system, selecting a medical discipline, selecting a medical protocol and/or procedure within the selected discipline, time stamping the selection, entering data associated with the protocol and/or procedure in appropriate fields in a GUI screen associated with the protocol and/or procedure, logging off of system after completion of the protocol data entry. The method can also include the step of submitting the protocol data to the database after review by a supervisor and polling entered data, where the submitting step can include changing a status of the entered data from a first state indicating initial data entry by a student and a second state indicating verification by an instructor. The submitting step can also include entering comments and levels of completion for student feedback and/or protocol repeat or to repeat steps within the procedure.

The present invention utilizes time clock routines to track student activity in hospital rotation programs. The system allows the student to log onto the time clock routine upon start of a given clinical task, training exercise, training program, rotation, etc. in a given department with a particular clinician. The system allows the student to enter competency and daily log data into the data base and then time clock out of the system when the rotation program is complete. The records entered by the student are tagged as non-validated. These records are then retrievable by the clinician or associated faculty member that can review the time clock data, the daily log data and the competencies data to certify that the student has attained the necessary time and proficiency in the protocol or procedure performed in a given rotation. The clinician or faculty member can leave comments and adequacy marks in the student records. If the record is sufficient, then the clinician or faculty member can validate the record or the student will have to pass back through the rotation to complete or redo the necessary protocol or procedure to attain validation.

Because the data is now stored in a database in a time relevant manner, statistics on programs, protocols, procedures, clinicians and/or faculty member evaluations can be performed in a time efficient and cost effective manner. The procedure simply corresponds to the execution of various functions in the system to attain evaluation statistics such as student time duration necessary to be certified in a given procedure, ranking of students, ranking of clinicians, ranking of faculty member, ranking of program disciplines and even ranking of facilities.

The present invention further relates broadly to a method for automating an accreditation procedure including the steps of selecting an institution, retrieving protocol and/or procedure data, where the data evidences the protocol and/or procedures used by the institution to train and certify medical students. The method also includes the step of retrieving medical student data corresponding to each students performance on each protocol and/or procedure and comparing the protocol and student data to a standard to determine accreditation problems and/or deficiencies.

General System Design and Layout

The following figures illustrate the system design and layout of the present invention. Of course, the figures incorporate various flow diagrams and program layouts and structures, but to an ordinary artisan, these diagrams simply show or illustrate one particular way of programming the steps necessary for accomplishing the system functions.

Referring now to FIG. 1A, a block diagram of a preferred system start process 100 of the present is shown to include a logon/login step 102 where a user enters a user name and password. Because the database utilized in this system is a rational data base, the system makes use of so called a middleware product, such as Lasso, sold by Blue World, to interface with the rational database. The middleware allows the system to construct variable lists corresponding to the data in the database and to manage database polling functions and to streamline data entry and retrieval between the system and the database. The middleware also allows construction of certain auxiliary files, tables and database structures for storage and maintenance of variable lists and data associated with variable lists.

The entered name and password is then checked against a list of qualified users in stored in a middleware file in a middleware user test step 104. If the user name and password do not match a qualified user name and password, then control is transferred along a NO branch 106 back to the logon step 102. If the user name and password matches a member of the middleware list, then control is transferred along a YES branch 108 to a login activity step 110. Next, the user again enters in the user name and password along with a status in a second logon step 112. The status identifies the user as a student, clinician or a member of the faculty. Next, a global variable is assigned in an assign global variable step 114 and, then, the user name, password and status are compared to the database user list in a conditional step 116. If the user name, password and status do not match an entry in the database list, then control is transferred along a NO branch 118 back to the logon step 102; otherwise, controlled is transferred along a YES branch 120 to a branch step 122, which directs the user to the appropriate routines for accessing, entering, deleting, modifying, manipulating and analyzing data in the database. In the case of the GUI, the user is transferred to GUI screen (preferably a web page) corresponding to a selection procedure, an entry form, a report, or the like. The branch step 122 sends the user to at least eight subsystems: an employer survey subsystem 200, a graduate survey subsystem 220, a student survey subsystem 240, a program personnel survey subsystem 260, a student subsystem 124, a clinician subsystem 126, a staff subsystem 128, and a faculty subsystem 130.

Figure 1B:
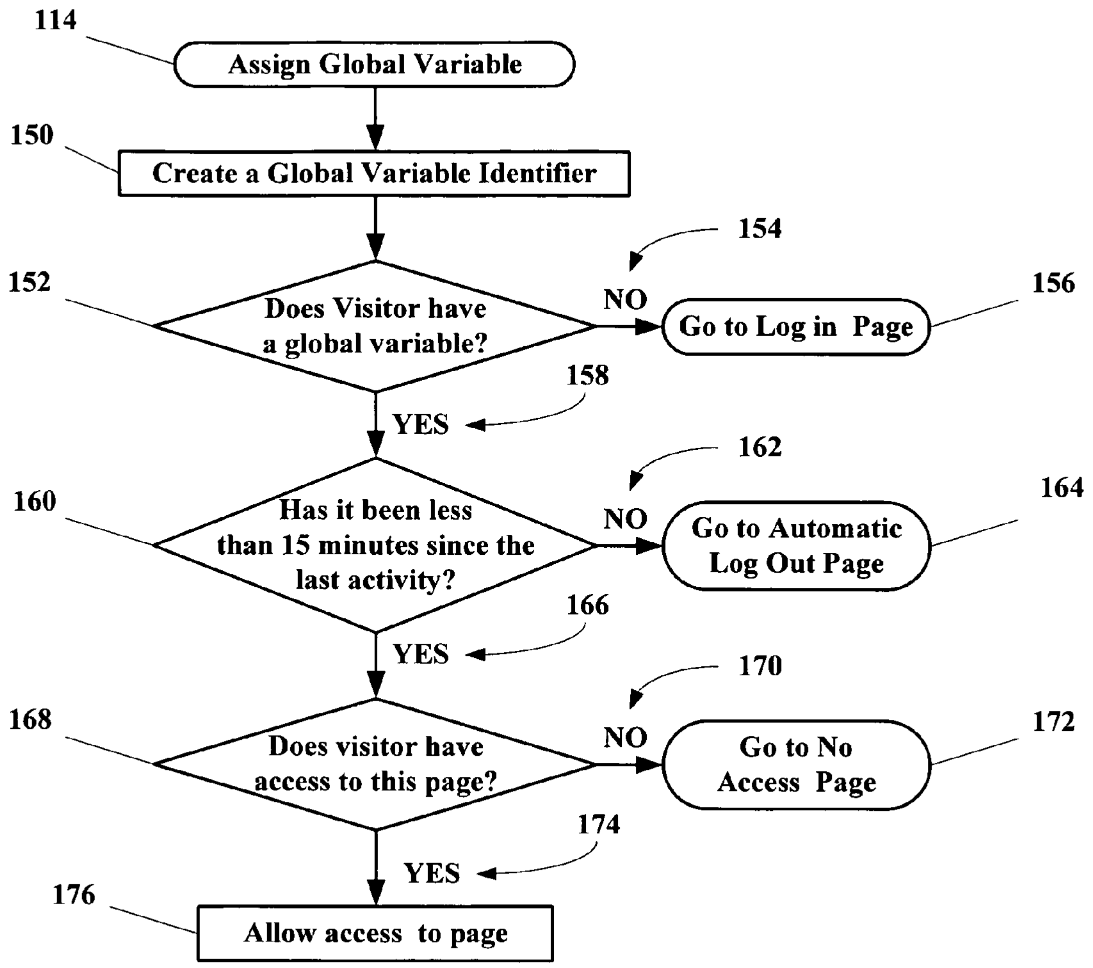
FIG. 1B depicts a block diagrams of a preferred embodiment of an assign global variable function of FIG. 1A.

Referring now to FIG. 1B, the global variable assignment routine 11.46 includes the step of creating a global variable identifier in an identifier step 150. The user name is then tested to determine whether a global variable is already established in a global variable test step 152. If no global variable matches the user, then control is transferred along a NO branch 154 to a log in step 156; otherwise control is transferred along a YES branch 158 to a check time of last activity step 160. If no activity has occurred in a period of time, preferably 15 minutes, then control is transferred along a NO branch 162 to an automatic logout step 164; otherwise control is transferred along a YES branch 166 to a check access privilege step 168. If the user is no privilege for the requested routine, then control is transferred along a NO branch 170 to a no access step 172; otherwise control is transferred along a YES branch 174 to allow access step 176.

Figure 2:
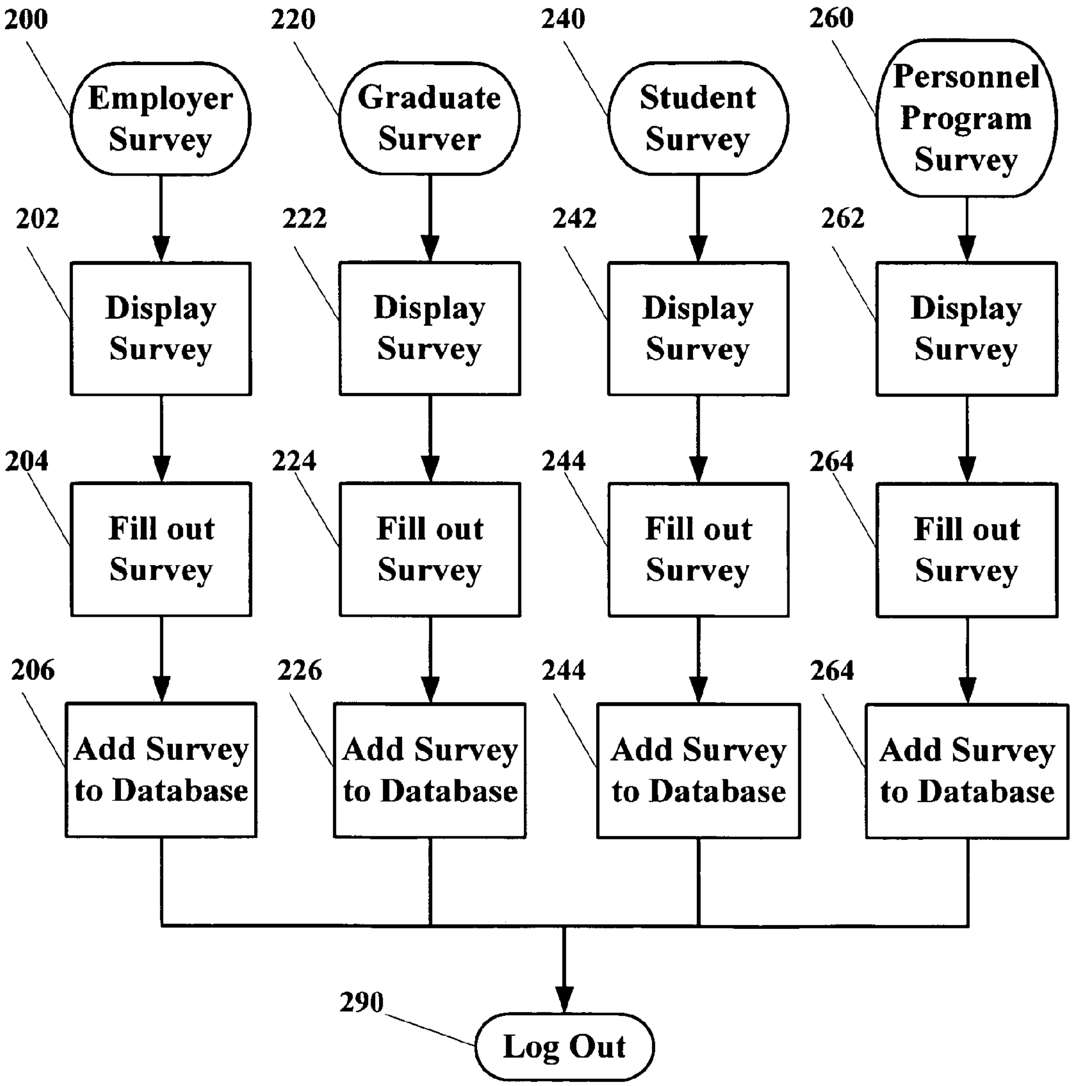
FIG. 2 depicts a block diagram of preferred embodiments of the survey subsystems of FIG. 1A.

Referring now to FIG. 2, a preferred embodiments of process for handling surveys 200, 220, 240, and 260 are shown in block diagram form. The employer survey handling process 200 includes a display survey step 202. The user then fills out the survey in a fill out survey step 204. Once complete, the survey is added to the employer survey database in an added survey to database step 206. The graduate survey handling process 220 includes a display survey step 222. The user then fills out the survey in a fill out survey step 224. Once complete, the survey is added to the graduate survey database in an added survey to database step 226. Similarly, the student survey handling process 240 includes a display survey step 242. The user then fills out the survey in a fill out survey step 244. Once complete, the survey is added to the student survey database in an added survey to database step 246. And finally, the program personnel survey handling process 260 includes a display survey step 262. The user then fills out the survey in a fill out survey step 264. Once complete, the survey is added to the program personnel survey database in an added survey to database step 266. After the completed survey is added to the database, each survey routine 200, 220, 240, and 260 transfers control to a log out step 280.

Figure 3:
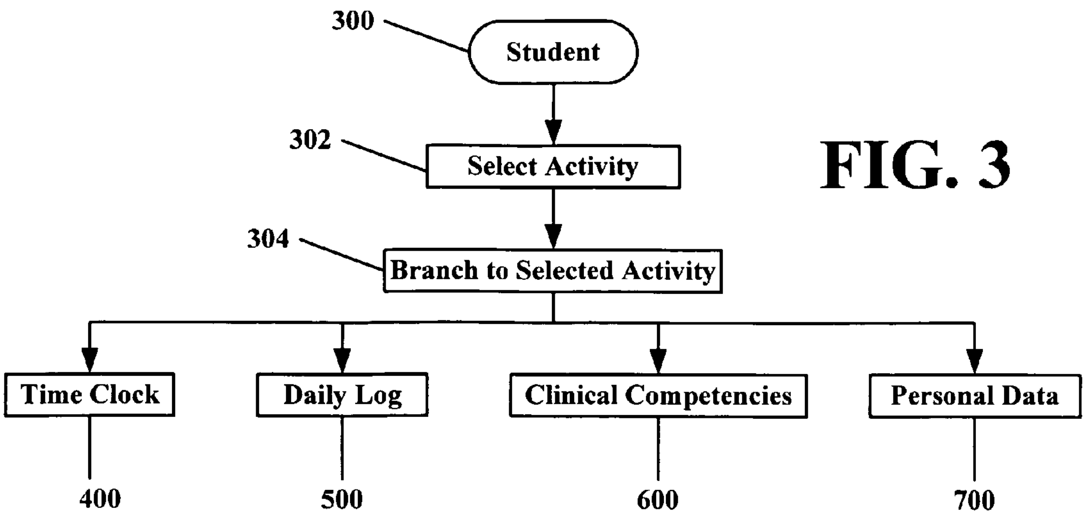
FIG. 3 depicts a block diagram of preferred embodiments of the student subsystem of FIG. 1A.

Referring now to FIG. 3, a block diagram of a preferred student subsystem 300 of the present is shown to include an activity selection step 302 where a user selects from a menu or from icons an activity the user desires to perform. The system then branches to the selected activity in a branch step 304, where control is transferred to a Time Clock function 400, a daily log function 500, a clinic competencies function 600 and a personal data function 700.

Figure 4:
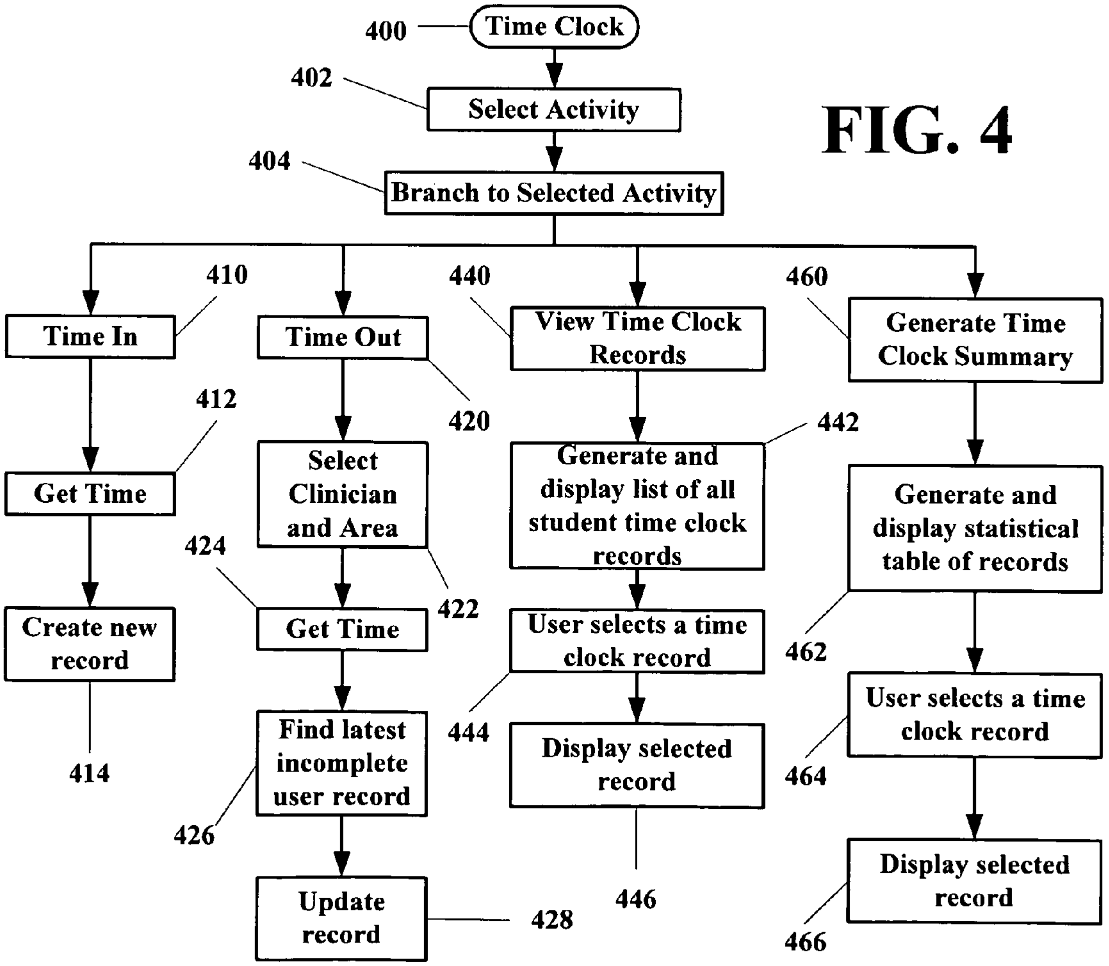
FIG. 4 depicts a block diagram of preferred embodiments of the Time Clock function of FIG. 3.

Referring now to FIG. 4, a block diagram of a preferred time clock function 400 of the present is shown to include an activity selection step 402 where a user selects from a menu or from icons the activity the user desires to perform. The system then branches to the selected activity in a branch step 404, where control is transferred to a Time In function 410, a Time Out function 420, a clinical competencies function 440 and a personal data function 460. The Time In function 410 includes a get time step 412, where the server obtains the current time and date from an atomic clock site and creates a record for the student with a time stamp in a create record step 414.

The time out function 420 includes a select clinician and hospital area step 422, where the user selects the clinician responsible for certifying the clinical activity, the area in the health care system in which the activity is to be performed and the activity to be performed such as performing an EKG in the cardiac care unit. The time out function 420 then gets the current time in a get time step 424, where the time is from an atomic clock. The function 420 then searches for the latest incomplete user record in a find step 426 and updates the record with the clinician identity, activity and hospital area in an update step 428.

The view time clock record function 440 includes a generate and display step 442, where the function 440 generates and displays a list of all time clock records for all students. Of course, the search can be narrowed to the user's records only or to any other subset of students by appropriate search restriction generally invokable from screen icons or menus. The user can then select a particular record in a record select step 444 and the function 440 displays the selected record in a display record step 446.

The generate time clock summary function 460 includes a generate and display step 462, where the function 460 generates and displays a table of records along with statistical data associated with the tabulated records. The user can then select a particular record in a record select step 464 and the function 460 displays the selected record in a display record step 466.

Figure 5:
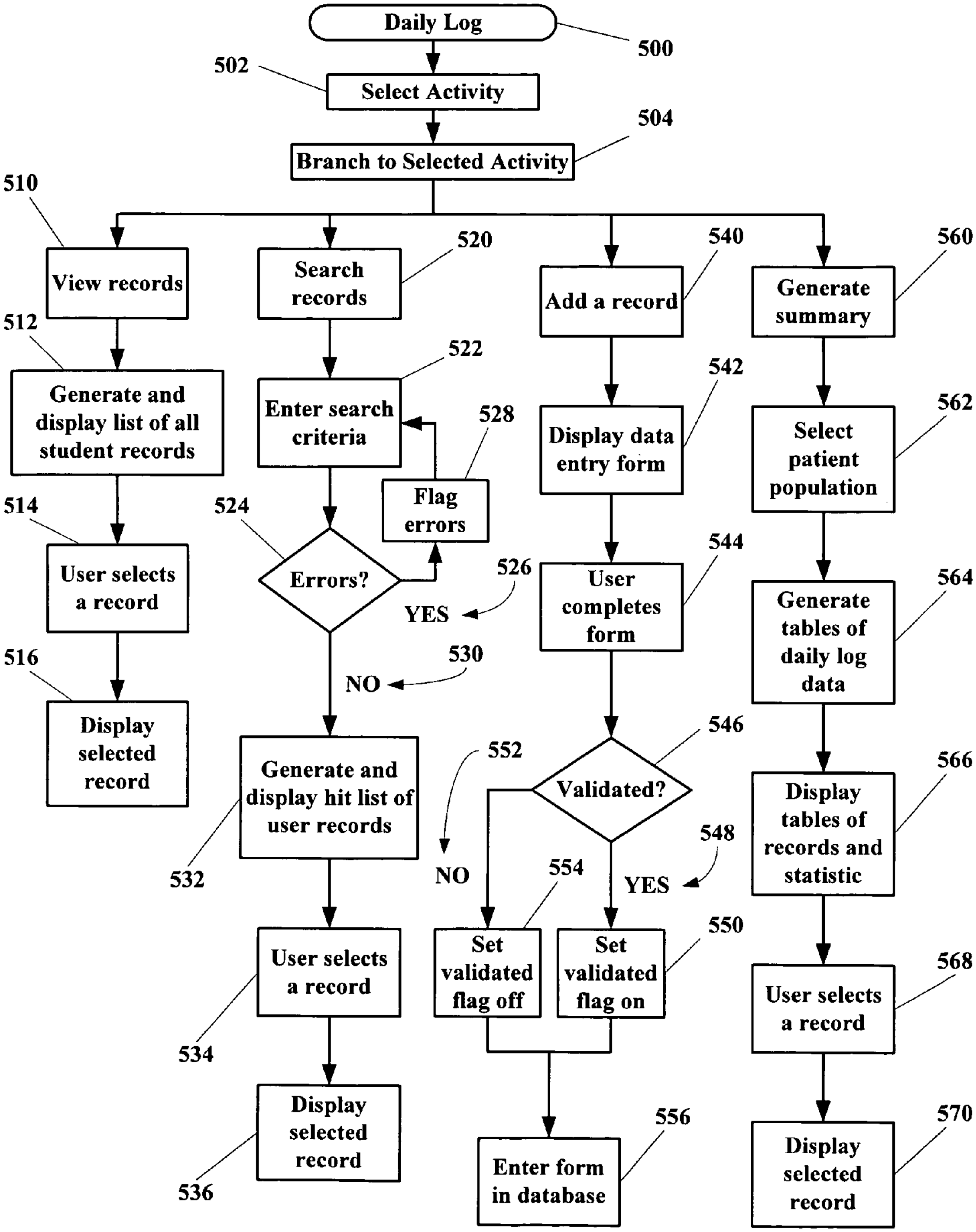
FIG. 5 depicts a block diagram of preferred embodiments of the Daily Log function of FIG. 3.

Referring now to FIG. 5, a block diagram of a preferred daily log function 500 of the present is shown to include an activity selection step 502 where a user selects from a menu or from icons the activity the user desires to perform. The system then branches to the selected activity in a branch step 504, where control is transferred to a view records function 510, a search records function 520, an add record function 540 and a generate summary function 560.

The view record function 510 includes a generate and display step 512, where a list of all student daily log records are generated and displayed on the user's screen. The user can then select any record in a select step 514, where upon the function 510 displays the selected record in a display step 516.

The search function 520 includes an enter search criteria step 522, where the user enters in a search string. The function 520, at the middleware level, check the search string for errors, missing criteria or the like in a check for errors step 524. If errors are found, control is transferred along a YES branch 526 to a flag error step 528, where the middleware highlights the fields that are incomplete or highlights incorrect or inaccurate criteria and forwards control back to the entry step 522. If no errors are found, then control is transferred along a NO branch 530 to a generate and display step 532, where the middleware finds all records (hits) satisfying the search criteria, generates a list of all hits and transfers the list to the GUI that then displays the information in list form on the user's screen or display device. Once the list is displayed, the user can select a particular record or list entry in a select step 534 and the selected record is displayed on the screen in a display step 536.

The add record function 540 includes a display data entry form step 542, where the function 540 displays a window including all of the fields needed for a student to complete and add a daily log record. The student then fills out the form placing data/information in the relevant fields in a complete form step 544. After the student completes the form, the record is checked for validation in a check validation step 546, where the clinician can validate the daily log entry currently with the students completion of the form. If the record is validated, then control is transferred along a YES branch 548 to a set validate flag to ON step 550; otherwise, control is transferred along a NO branch 552 to a set validate flag to OFF step 554. Once the validate flag is set to either a ON or OFF condition, the daily log record is entered into the database in a entry step 556.

The generate summary function 560 includes a select patient population step 562, where the student selects the type of patient population for which the student desires a summary. For example, if the student desires to look at daily log summaries for cardiac patients, then the student would select cardiac patient populations from patient population selection menus or icons or search string entries in the select patient population step 562. Once the student selects a desired student population, the function 560 generates a summary table of daily log data for the selected patient population in a generate step 564. The function 560 then displays the table along with statistics associated with the data stored in the daily log for which statistical data can be performed in a display table step 566. After the table is generated and displayed, the function 560 allows the student to select a particular record in a select record step 568 which is then displayed by the function 560 in a display selected record step 570.

Figure 6:
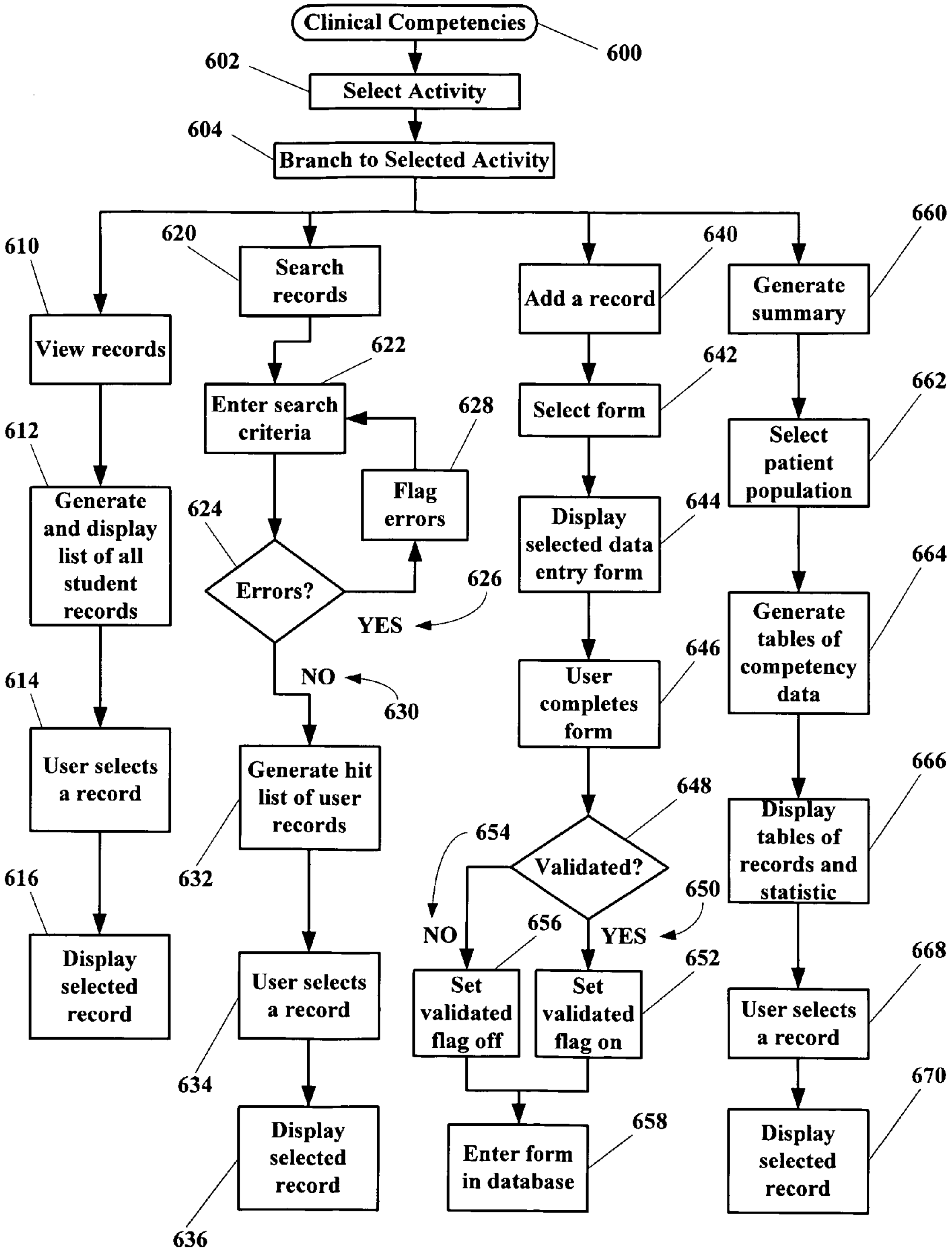
FIG. 6 depicts a block diagram of preferred embodiments of the Clinical Competencies function of FIG. 3.

Referring now to FIG. 6, a block diagram of a preferred student clinical competencies function 600 of the present is shown to an activity selection step 602 where the student selects from a menu or icons the activity the student desires to perform. The system then branches to the selected activity in a branch step 604, where control is transferred to a view records function 610, a search record function 620, an add record function 640 and a generate clinical competencies summary data function 660.

Figure 7:
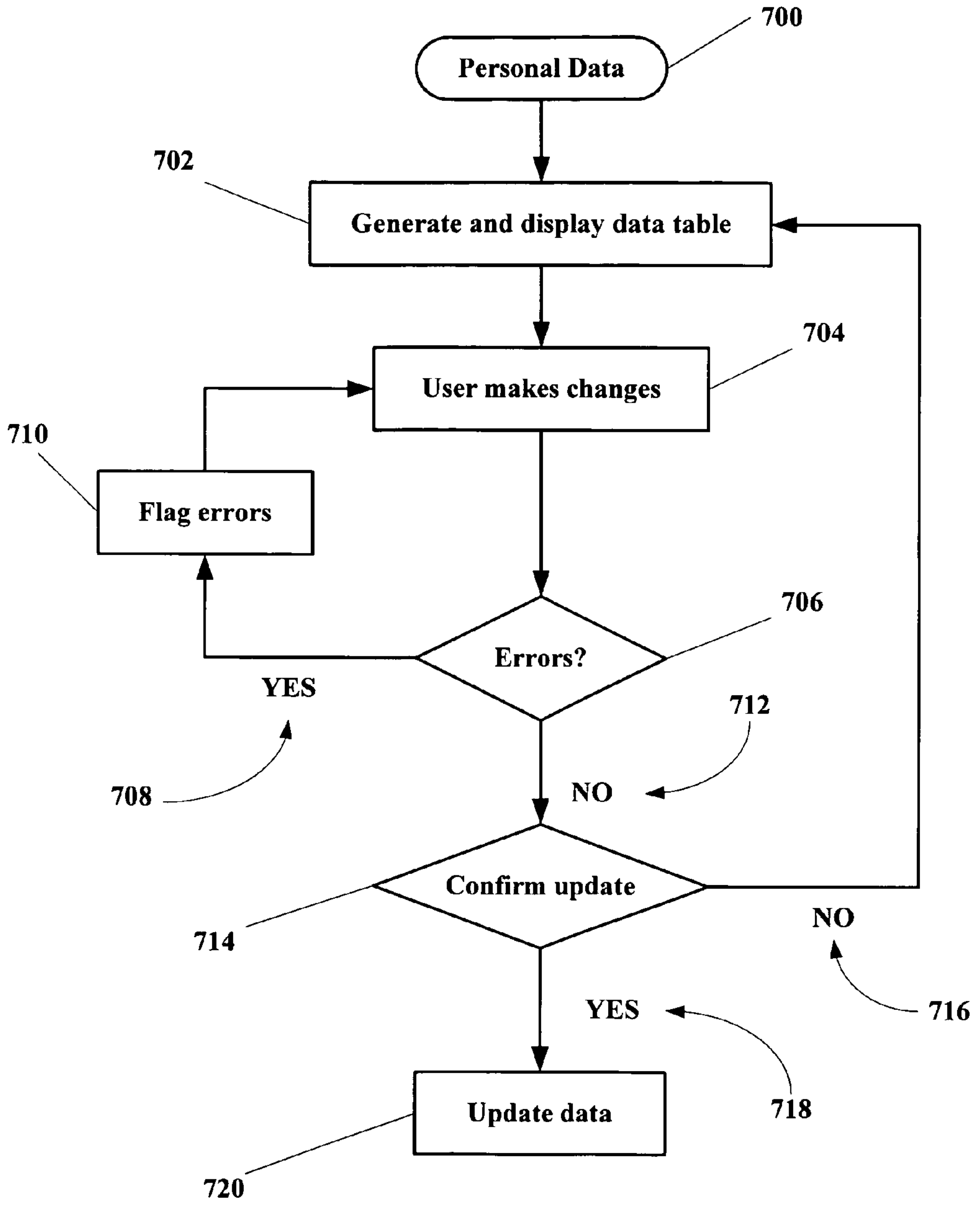
FIG. 7 depicts a block diagram of preferred embodiments of the Personal Data function of FIG. 3.

Referring now to FIG. 7, a block diagram of a preferred personal data function 700 of the present is shown to include a generate and display data table step 702 where the student's personnel data is displayed in one column and an adjacent column displays blank field where the student can enter updated data such as phone numbers, address information, or the like. The student then enters updated information in a make changes to data step 704. The function 700 then check the changes for errors in an error checking step 706. If errors are found, then control is transferred along a YES branch 708 back to the make changes in data step 704. The error checking step 706, leaves correct change data ready for database updating and highlight incorrect or incomplete data for reenter by the student. If no errors are found in the changed data, then control is transferred along a NO branch 710 to a confirm update data step 712. If the user confirms update, then control is transferred along a YES branch 714 to an update database step 716, where the updated data is entered into the students personal data record. If the student does not confirm the changes, then control is transferred along a NO branch to the make changes step 704. Of course, in all of these function, the student can logout of the system by activating a logout icon or by selecting the function from a selection menu.

Figure 8:
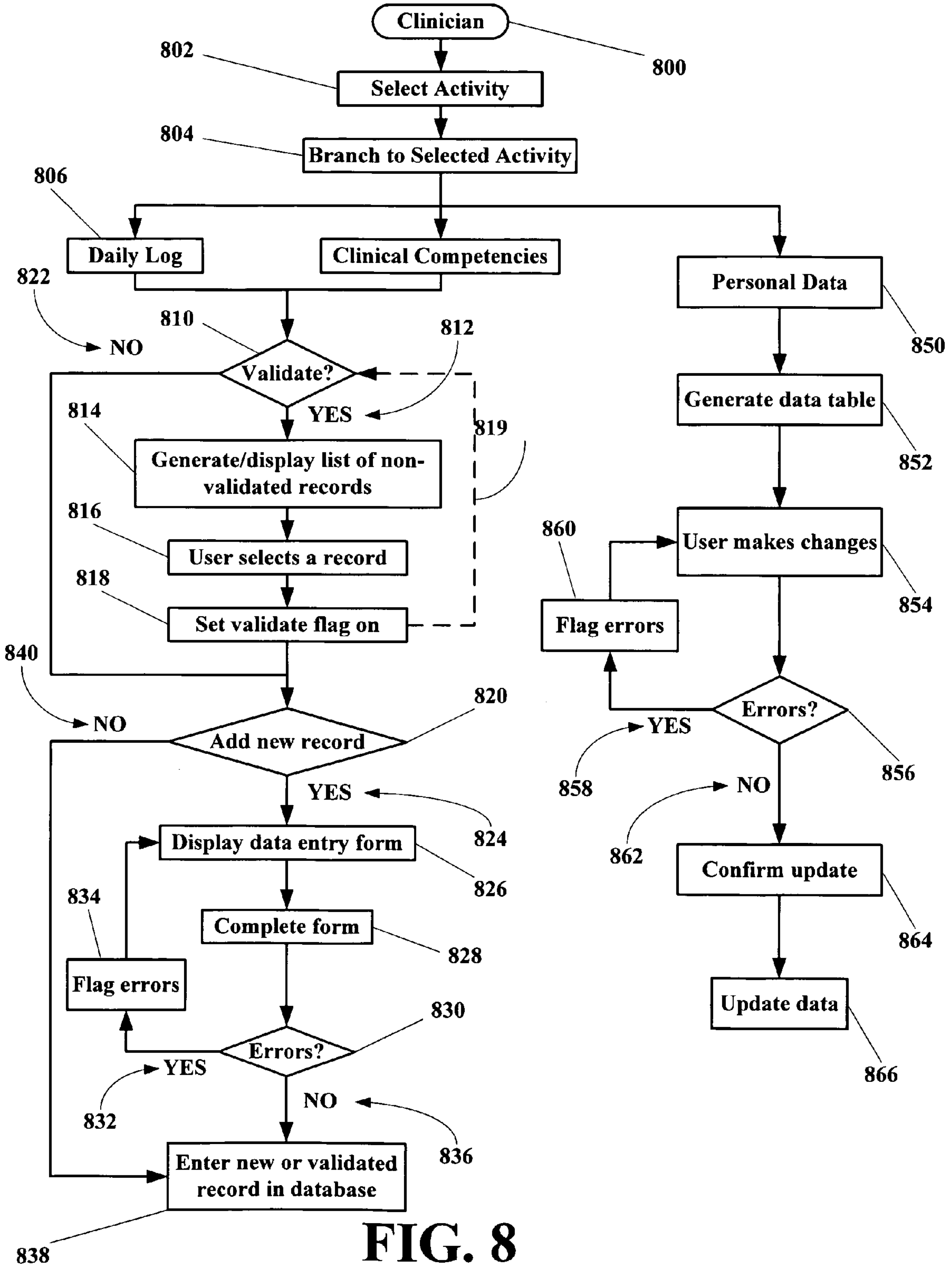
FIG. 8 depicts a block diagram of preferred embodiments of the clinician/instructor subsystem of FIG. 1A.

Referring now to FIG. 8, a block diagram of a preferred clinician or instructor subsystem 800 of the present is shown to include an activity selection step 802 where a user selects from a menu or from icons and activity the user desires to perform. The system then branches to the selected activity in a branch step 804, where control is transferred to a daily log function 806, a clinic competencies function 808 and a personal data function 850. The daily log function 806 and the clinical competencies function 808 both proceed to a check validate step 810, where student daily log records or competency records are checked to determine whether student records assigned to the clinician are present which have not been validated either by the clinician or a faculty member. If unvalidated records exist, then control is transferred along a YES branch 812 to a generate/display step 814, where student records assigned to this clinician are scanned and non-validated records are collected and a list of non-validated records displayed. The clinician can then select an unvalidated record in a select step 816 and validate the record in a validate record step 818, where the validation flag is set to ON from OFF.

Of course, the routine does not have to use a flag field, the routine can use any technique for designating the record a validated or unvalidated such as storing the validated records in one list and the unvalidated records in another list. Although the present flow chart shows only a single record being selected and then control transferred to an add new record step, control can also be transferred back up to the validate check step 810 along optional path 819 until all unvalidated records are validated or of course the clinician can validate as many records as the clinician desires and go onto the add record set or to an enter record step.

If no records are unvalidated, then control is transferred from the validate step 810 along a NO branch 820 to a add new record step 822, where the clinician can add a new daily log record or competency record. If the clinician desires to add a new record, then control is transferred along a YES branch 824 to a display data entry form 826 for either a daily log entry or a competency entry. The clinician then completes the form in a complete form step 828. Once complete, the function 800 checks the data for errors, incomplete data or missing data in a check for errors step 830. If errors exist, then control is transferred along YES branch 832 to a flag errors step 834, where correct data is shown in the appropriate fields and errors, missing data, incomplete data are highlighted and control is transferred back to the enter data step 826. If no errors are found or if all errors have been corrected, then control is transferred along a NO branch 836 to an enter validated records and/or added records to the database step 838. The routine can also include a confirm database entry step. If no new records are to be added, then control is transferred from the add new record step 820 along a NO branch 840 to the enter data into the database step 838.

Figure 9A:
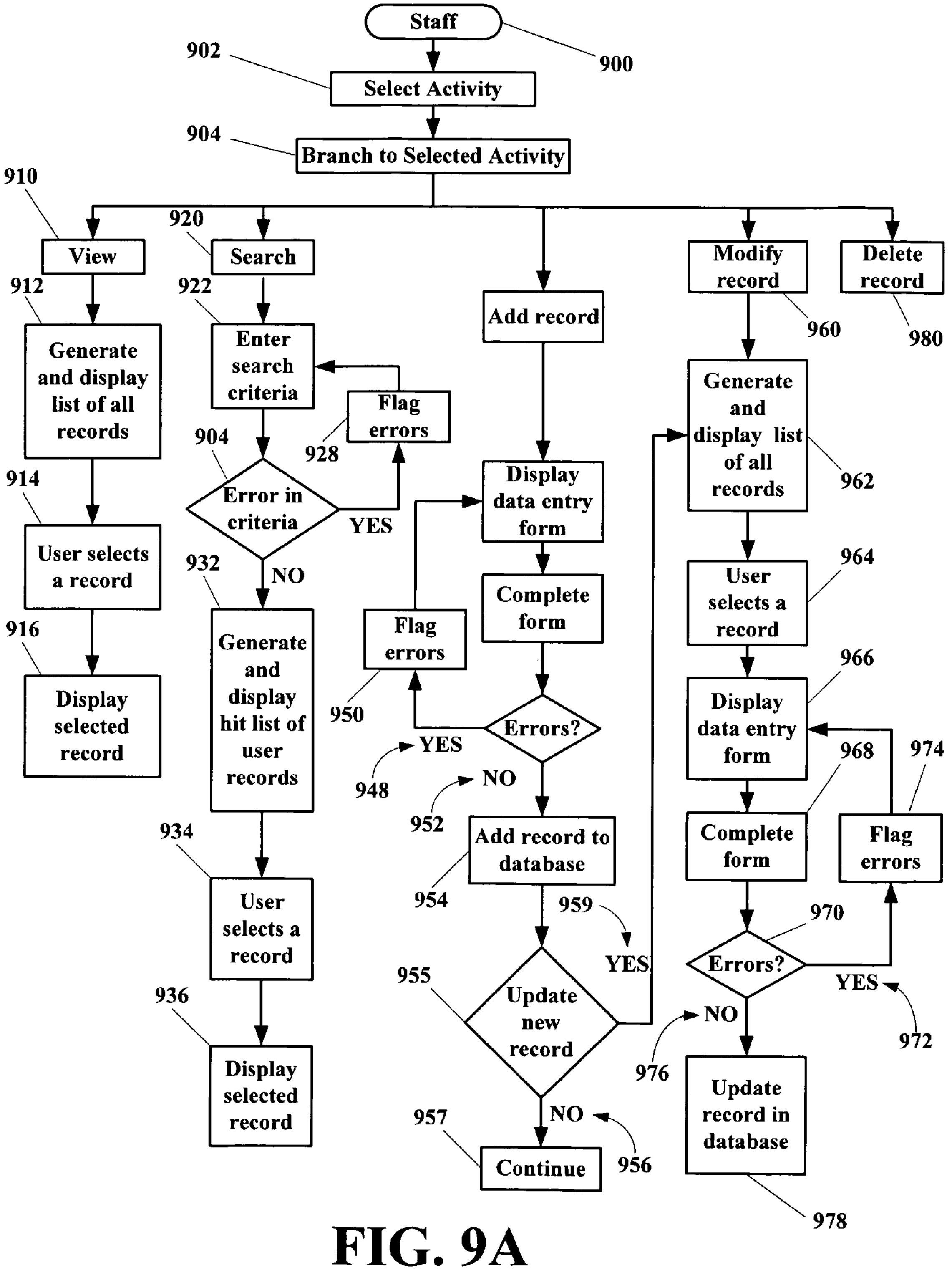
FIGS. 9A&B depicts a block diagram of preferred embodiments of the staff subsystem of FIG. 1A.
Figure 9B:
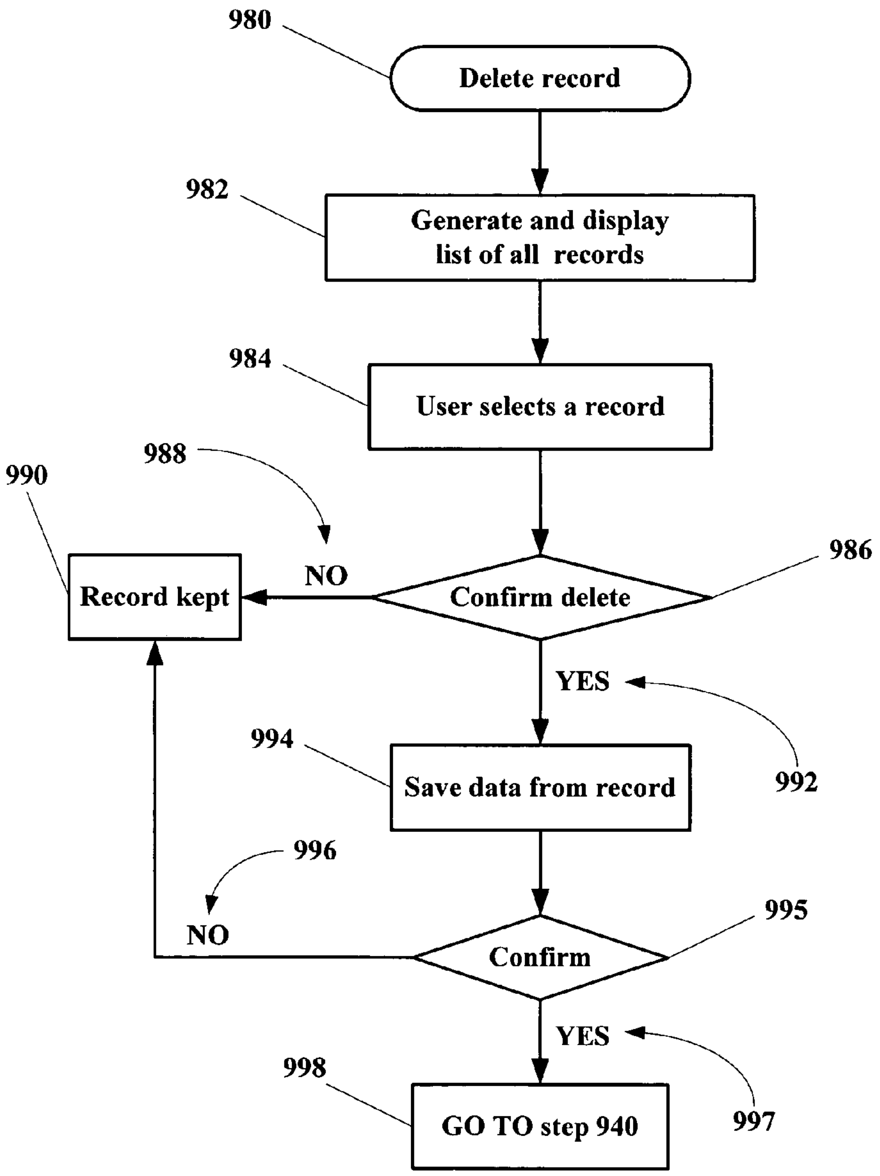

Referring now to FIGS. 9A&B, a block diagram of a preferred staff subsystem 900 of the present is shown to include an activity selection step 902 where a user selects from a menu or from icons and activity the user desires to perform. The system then branches to the selected activity in a branch step 904, where control is transferred to a view record function 910, a search records function 920, an add record function 940, a modify record function 960 and a delete record function 980.

The view record function 910 includes generate and display a list of all staff personal data records step 912. Once the data records have been generated and displayed, the staff member can select a particular record in a select step 914, which is then displayed by the function 910 in a display selected record step 916.

The search records function 920 includes an enter search criteria step 922, where the staff member enters the search criteria desired. The function 920 then check the search criteria for errors in a check for errors step 924. If the search has errors, incorrect entries or incomplete entries, then control is transferred along a YES branch 926 to a error flagging step 928, where correct enters are left filled in and inaccurate or incomplete entries or required fields are highlight and control is sent back to the enter search criteria step 922. Once the search passes the error check step 922, control is transferred along a NO branch 930 to a generate and display step 932, where a hit list of records corresponding to the search are displayed. The staff member can then select a particular record in a select step 934 and the function 920 displays the selected record in a display step 936.

The add record function 940 includes a display data entry form step 942, which allows the staff member to fill in the required information in a complete form step 944. The function 940 then checks the form for errors in an error checking step 946. If an error is found in the data, then control is transferred along a YES branch 948 to a flag error step 950, where correct data is left alone and errant or incomplete data are highlight and control is sent back to the data entry step 942. If no errors in the data are found, then the check error step 946 transfers control along a NO branch 952 to an add record to the database step 954. After the record has been added to the database, the staff member is asked whether the member desires to update the data in the new record in a conditional update step 955. If the staff member does not desire to update the data in the new record, the control is transferred along a NO branch 956 to a continue step 958 or to any other process the staff member desires to invoke from pull down menus or icons associated with the window in which the update new record step 955 is displayed. If the staff member desires to update the data in the added record, then control is transferred along a YES branch 959 to a generate and display step 962 associated with the modify record function 960.

The modify record function 960 includes a generate and display a list of all staff personal data records step 962, where all records containing data about the staff member is assembled and displayed in a selectable list format. The staff member can then select a record in a select step 964. The function 960 then displays the selected record as a data entry form in a display step 966. The staff member then updates the data by entering new data in any desired data entry field in the form in a complete form step 968. The updated data is then checked for errors in error checking step 970. If errors are found (errant data, inaccurate data or incomplete data), then control is transferred along a YES branch 972 to an flag error step 974 where correct data is left alone and errant, inaccurate or incomplete data is highlighted. After errors are highlighted, control is returned to the data entry step 966. If no errors are found, then control is transferred along a NO branch 976 to an update record in the database step 978.

The delete record function 980 includes a generate and display a list of all staff personal data records step 982. The staff member then selects a record to be deleted in a select step 984. The function 960, then requests the staff member to confirm the deletion in a confirm step 986. If the confirm step is negative, then control is transferred along a NO path 988 to a keep record step 990. If the staff member still wants the record desired, then control is transferred along a YES branch 992 to a save data from record step 994, where the data from the record is saved by the middleware routine in a deleted data table so that data deletion errors can be corrected later or scanned to determine what type of errors are being made so that functions can be augmented to reduce the incidence of such errors. After the data is save, the staff member is again asked if the data record is to be deleted in a second confirm step 995. Again, if the deletion is not to be made, then control is transferred along a NO branch 996 to the keep record step 990 and the middleware table is updated to remove the saved record corresponding to the record for which deletion has been aborted. If the staff member again confirms deletion, then control is transferred along a YES branch 997 to a go to step 998, which transfers control of the function to the add record function 940.

Figure 10A:
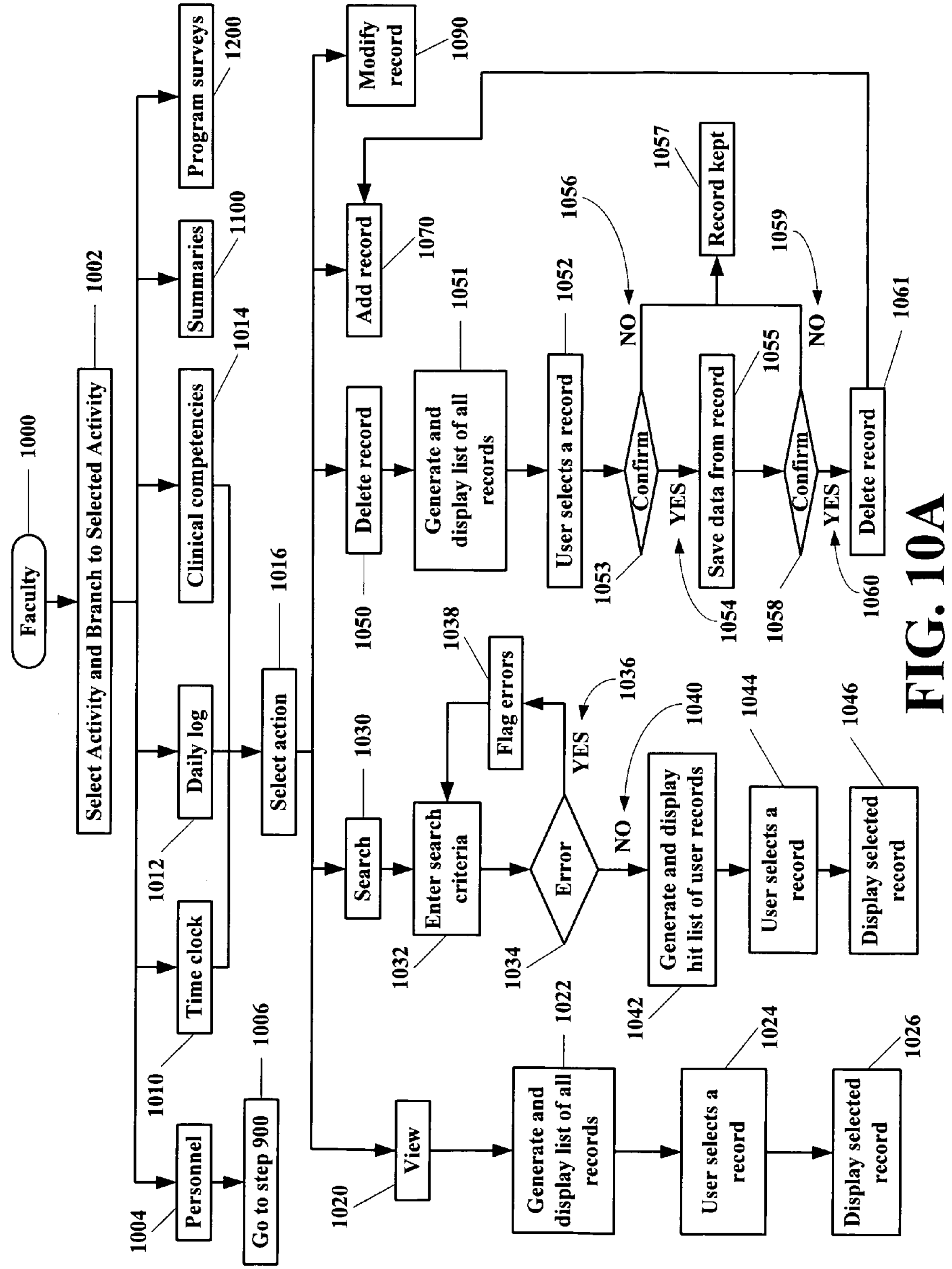
FIGS. 10A&B depicts a block diagram of preferred embodiments of the faculty subsystem of FIG. 1A.
Figure 10B:
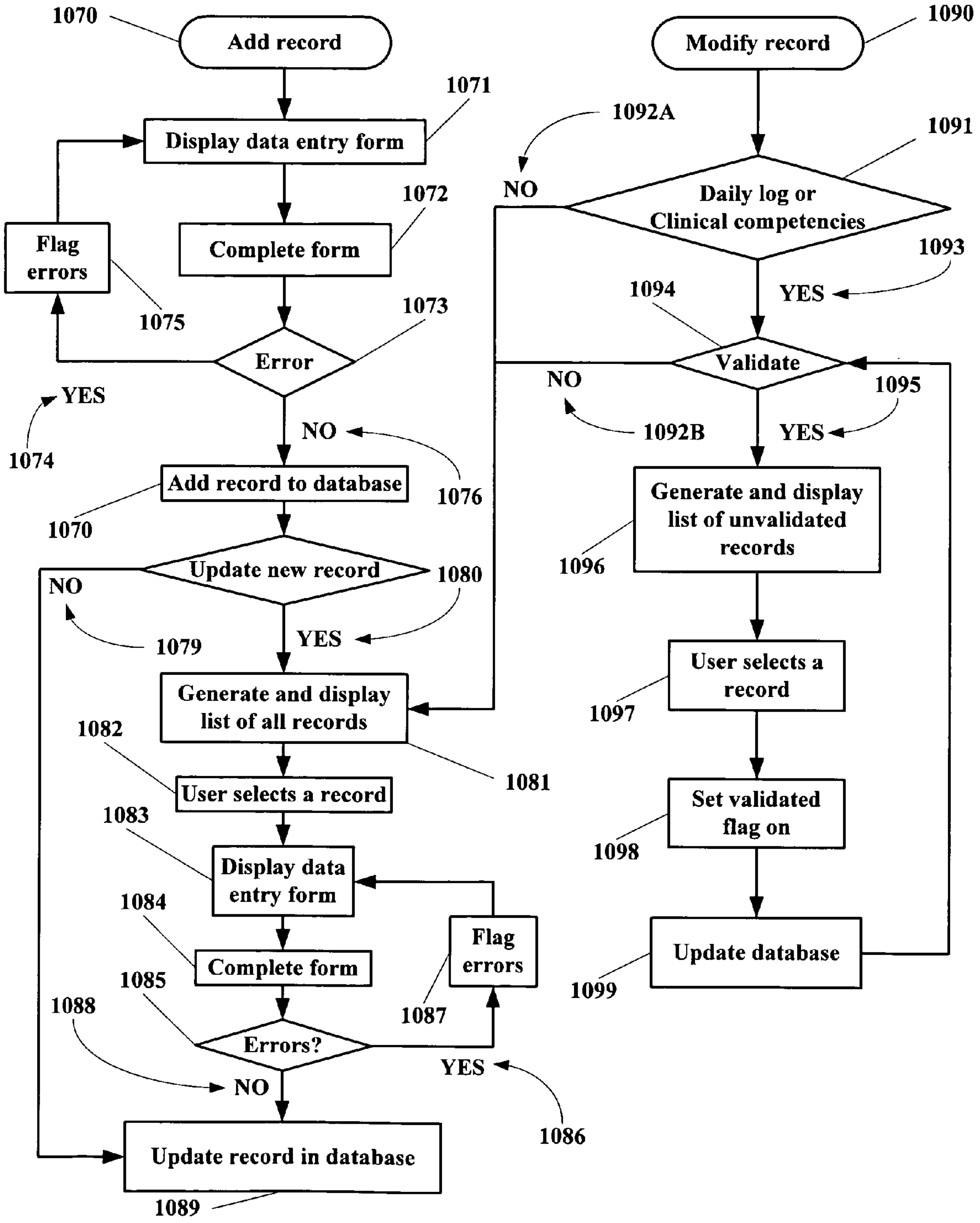

Referring now to FIG. 10, a block diagram of a preferred faculty subsystem 1000 of the present is shown to include a select activity and branch to selected activity step 1002 where a faculty member selects from a list of functions: a personal data function 1004, a time clock function 1010, a daily log function 1012, a clinical competencies function 1014, a summary function 1100 and a program survey function 1200. The personal data function 1004 routines the system to a faculty personal data subsystem 1006 that is identical to the staff subsystem of FIGS. 9A and B except that the data is associated with a faculty personal data database instead of the staff personal data database. Because the functionality if identical, the functionality of the subsystem will not be repeated here with language changes from staff to faculty member.

The time clock, daily log and clinical competencies function 1010, 1012 and 1014, respectively, all allow the faculty member to select from five record functions: view record function 1020, search records function 1030, delete record function 1050, add record function 1070 and a modify record function 1090. The view record function 1020 includes a generate and display step 1022 which generates and displays a list of all data records. Once the list is displayed, the faculty member can select a given record from a select step 1024, which causes the selected record to be displayed in a display step 1026.

The search function 1030 includes an enter search criteria step 1032, where the faculty member enters as set of search criteria. The function 1030 then checks the search criteria for errors in an error checking step 1034. If errors are found, then control is transferred along a YES branch 1036 to a flag errors step 1038, where correct data is left alone and errant or incomplete data is highlighted and control is returned to the enter search criteria step 1032. If no errors are found, then control is transferred along a NO branch 1040 to a generate and display step 1042, where a hit list of all records satisfying the search criteria are displayed. The faculty member can then select a particular record in a select step 1044, which is displayed in a display step 1046.

The delete function 1050 includes a generate and display step 1051, where a list of all records is displayed. Once the list is displayed, the faculty member can select a particular record in a select record step 1052. The function 1050 then asks the faculty member to confirm the deletion in a confirm test step 1053. If the faculty member confirms the deletion, then control is transferred along a YES path 1054 to a save data step 1055, where data from record is saved in a middleware deleted data table. If the faculty does not confirm deletion is confirm step 1053, then control is transferred along a NO branch 1056 to a keep record step 1057. After the record data is save in step 1055, the function 1050, then again asks the faculty member to confirm deletion is a second confirm test step 1058. If the faculty member decides to abort the deletion, then control is transferred along a NO branch 1059 to the keep record step 1057, which also cause the saved data table to be updated to remove the saved data corresponding to the aborted deletion attempt. If the faculty member confirms deletion, then control is transferred along a YES branch 1060 to a delete record step 1061, which removes the record from the database. Control is then transferred to the add function 1070 in a go to step 1062.

The add function 1070 includes display data entry step 1071, where a data entry form is displayed corresponding to the appropriate form for time clock data entry, daily log data entry and clinical competencies data entry. The faculty member then complete the appropriate data entry form 1072. The function 1070 then check the entered data for errors in an errors step 1073, where the data is checked for error and/or incomplete data entry. If errors exist, then control is transferred along a YES branch 1074 to an error flag step 1075, where correct data is left alone and errant or incomplete data is highlighted and control is returned to the complete form step 1072. If no errors exist in the entered data, then control is transferred along a NO branch 1076 to an add record to database step 1077. After record addition, the faculty member can alter the date in an update new record step 1078. If no alteration is needed, then control is transferred along a NO branch 1079 to an update record in database step 1089. If the new record needs updating, then control is transferred along a YES branch 1080 to a generate and display step 1081, where a list of all records is displayed. Once the list is displayed, the faculty member can select a particular record in a select record step 1082. After selection, the data entry form corresponding to the data record is displayed in a form display step 1083. The faculty member can then complete the form with updated information or data in a complete step 1084. Again, the function 1070 checks the data for errors in a error checking step 1085. If errors are found, then control is transferred along a YES branch 1086 to a flag error step 1087, where correct data is left alone and errant or incomplete data are highlighted and control is returned to the complete form step 1084. If no errors exist, then control is transferred along a NO branch 1088 to an update database step 1089, where the updated record information or data is stored to update the data in the database.

The modify function 1090 includes a test step 1091, where the function 1090 determines whether the faculty member is in the daily log or clinical competencies subsystem because these two functions, unlike the time clock function, can include non-validated student records. If the records are time clock records, then control is transferred along a NO branch 1092A to the generate display step 1081 of the add function 1070. If the records are daily log or clinical competency records, then control is transferred along a YES branch 1093 to a validate test step 1094, where the function 1090 checks to see if there are unvalidated records. If no unvalidated records exist, then control is transferred along a NO branch 1092B to the generate display step 1081 of the add function 1070. If unvalidated records exist, then control is transferred along a YES branch 1095 to a generate and display step 1096, where a list of all records is displayed. Once the list is displayed, the faculty member selects a record to be validated in a select step 1097 record is validated in a set validate flag step 1098, where the unvalidated record is set to validated. The newly validated record is then submitted to the database in an update database step 1099 and control is returned to the validate test step 1094.

Figure 11:
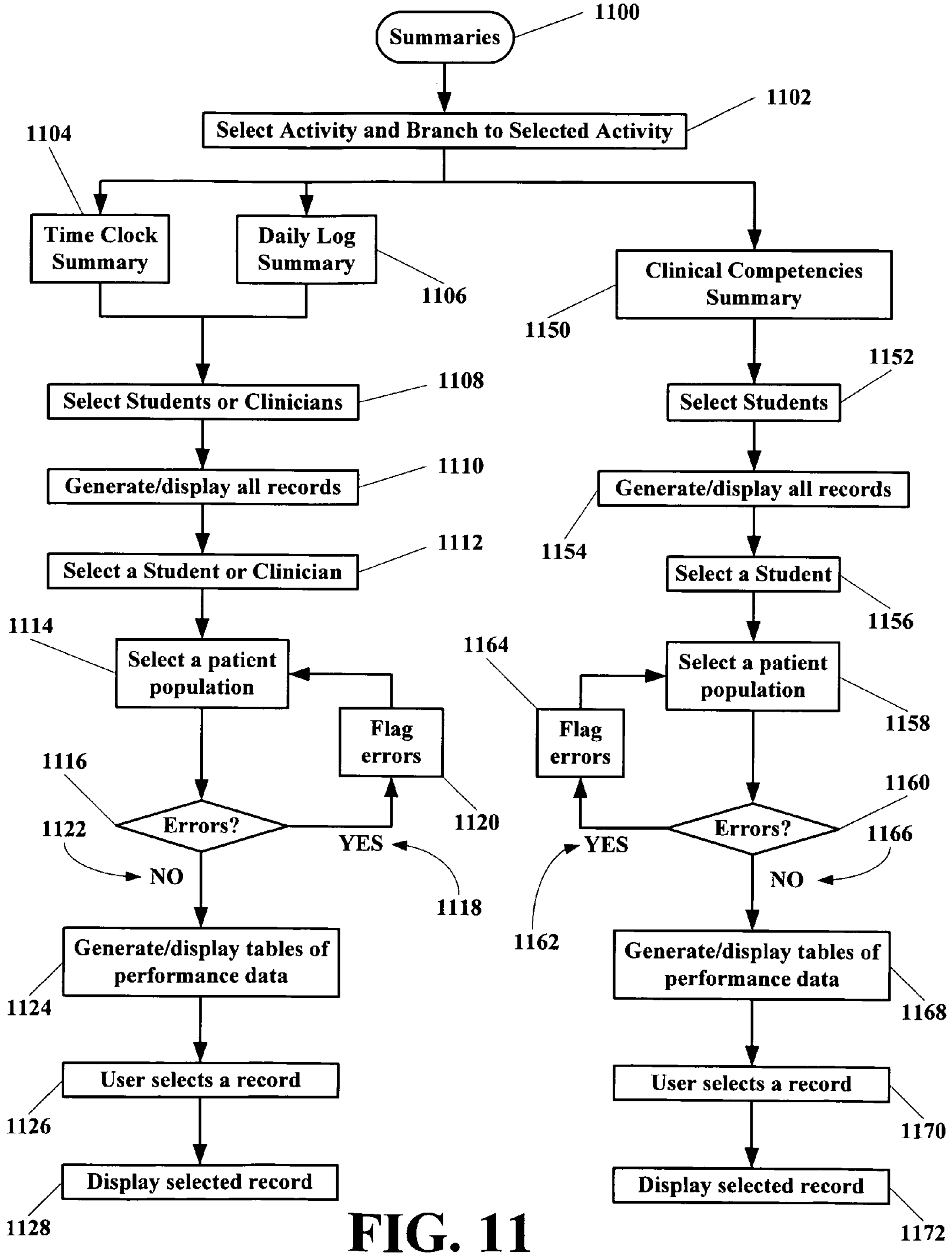
FIG. 11 depicts a block diagram of preferred embodiments of the summaries subsystem of FIG. 1A.

Referring now to FIG. 11, a block diagram of a preferred summary subsystem 1100 of the present is shown to include a select activity and branch to selected activity step 1102, where the faculty member selects a summary functions: time clock summary function 1104; a daily log summary function 1106 and a clinical competencies function 1150.

The time clock summary 1104 and the daily log summary 1106 include the same step which start with a select student or clinician step 1108. Once the record class is selected, the function 1104 or 1106 generates and displays all associated records in a generate and display records step 1110. Next, the faculty member selects a particular student or clinician in a second select step 1112. Of course, the selection step may allow for numerous students or clinicians to be selected. Next, the faculty member selects a patient population in a third select step 1114. Of course all three selection steps 1108, 1112 and 1114 can be combined and the generate and display step 1110 would not be necessary. Once all the selection are completed, the function 1104 or 1106 check for selection errors in an error checking step 1116. If errors exist, then control is transferred along a YES branch 1118 to a flag error step 1120, where correct data is unaffected, while errant and incomplete data is highlighted and control is returned to the select patient population step 1114. If no errors exist, then control is transferred along a NO branch 1122 to a generate and display step 1124, where a table containing all records corresponding to the selection criteria are displayed along with all performance data and statistical data associated therewith. The faculty member can then select a particular record in a select record step 1126 which is then displayed in a display step 1128.

Figure 12:
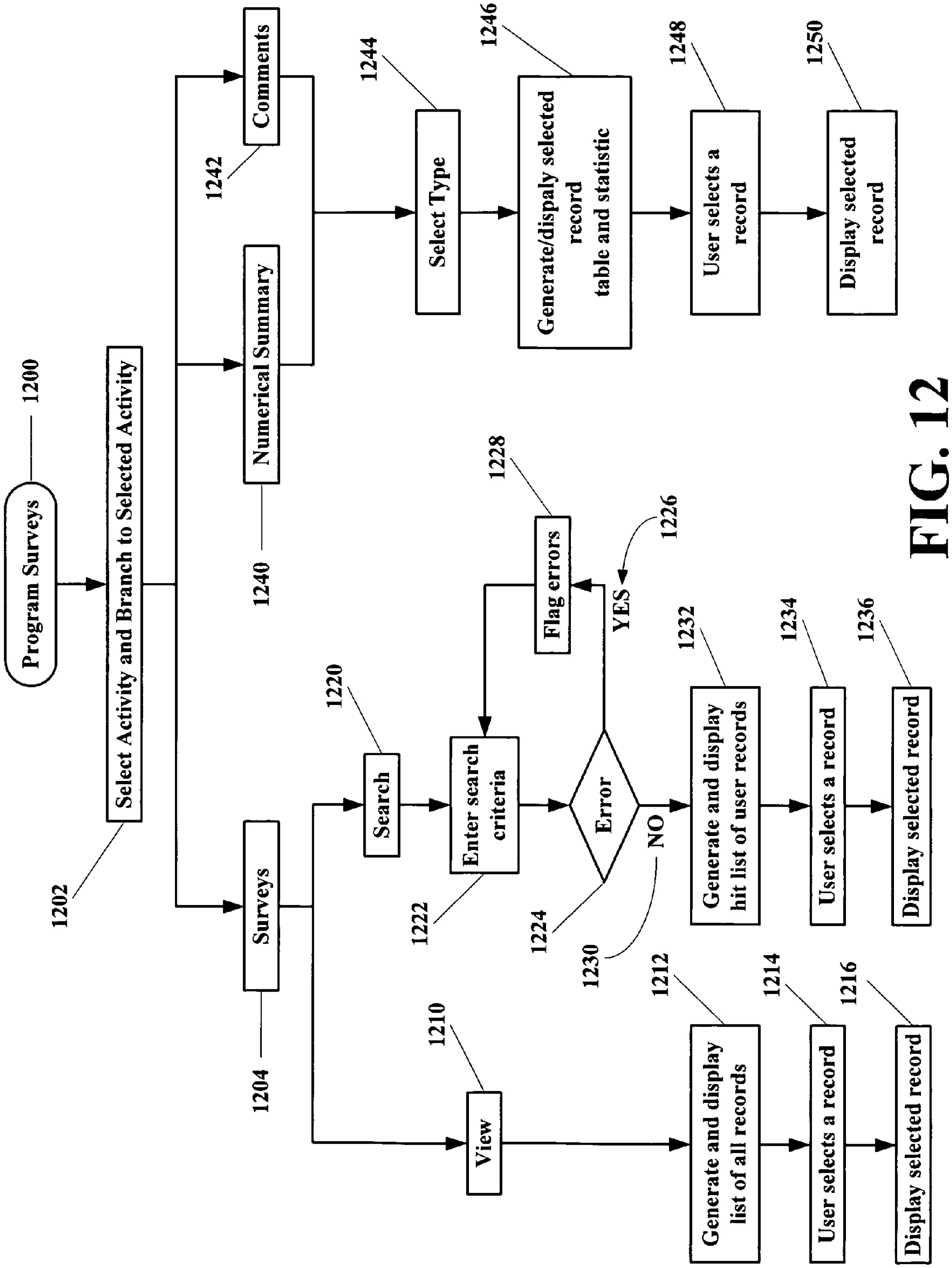
FIG. 12 depicts a block diagram of preferred embodiments of the Program Surveys subsystem of FIG. 1A.

Referring now to FIG. 12, a block diagram of a preferred survey subsystem 1200 of the present is shown to include a select activity and branch to selected activity step 1202 where the faculty member can select: a survey function 1204, a numerical summary function 1240 of a comments function 1242. The surveys function 1204 includes a view function 1210 and a search function 1220. The view function 1210 includes a generate and display step 1212, which generates and displays all relevant records. The faculty member can then select a particular record 1214 from the records which is then displayed in a display step 1216. The search function 1220 includes an enter search criteria step 1222 followed by an error checking step 1224. If errors are found, then control is transferred along a YES branch 1226 to a flag error step 1228, where correct data is unaffected and errant and incomplete data is highlighted and control is returned to the enter search step 1222. If no errors are found, then control is transferred along a NO branch 1230 to a generate and display step 1232 which generates and displays a hit list of records that correspond to the search criteria. The faculty member can then select a particular record in a select step 1234 which is then displayed in a display step 1236.

The numerical summary function 1240 and comments function 1242 each include a select type step 1244, where the faculty member selects the type of data desire, e.g., student, graduate, employer or program personnel. Once a selection has been made, the function 1240 and 1242 generates and displays a the selected records in a generate and display step 1246. The displayed data is obtained via the middleware which determines the count of each rating (1 to 5), percentage of each rating, the total number of responses, mean, median, standard deviations and other statistical data as well as the number of NA (not applicable) results and the number of blank entries. The faculty member can then select a particular record in a select step 1248 which is then displayed in a display step 1250.

Graphic User Interface Layout

The following figures illustrate the GUI interface between the user and the system. The figure all relate to one embodiment of this system to respiratory care medical program. The figures are include for illustration of the GUI interface, input screen and function screens corresponding to the system conceptual flow chart described in the preceding section.

Figure 13A:
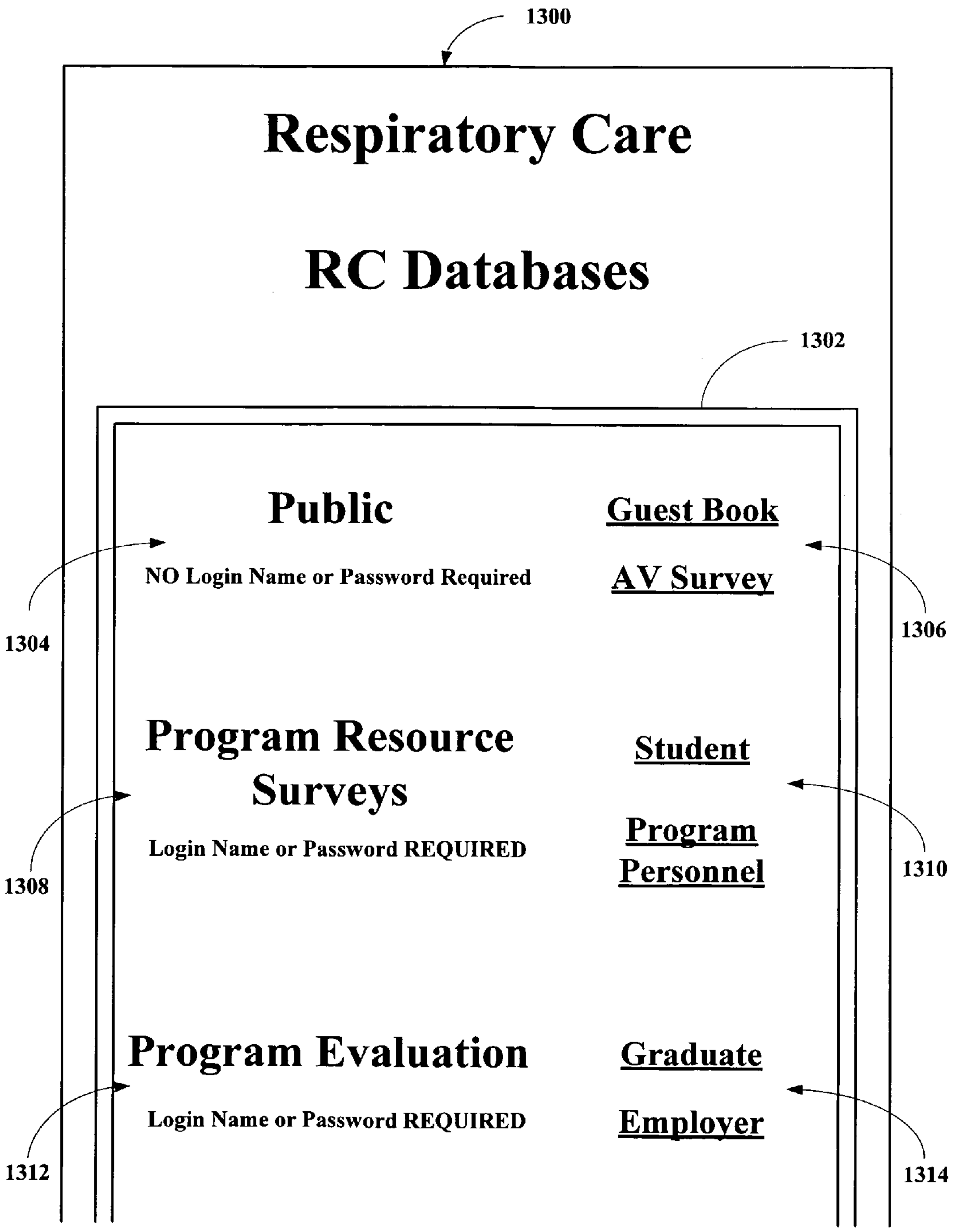
FIG. 13A-C depicts a preferred screen image for the main screen of a respiratory care embodiment of this invention.
Figure 13B:
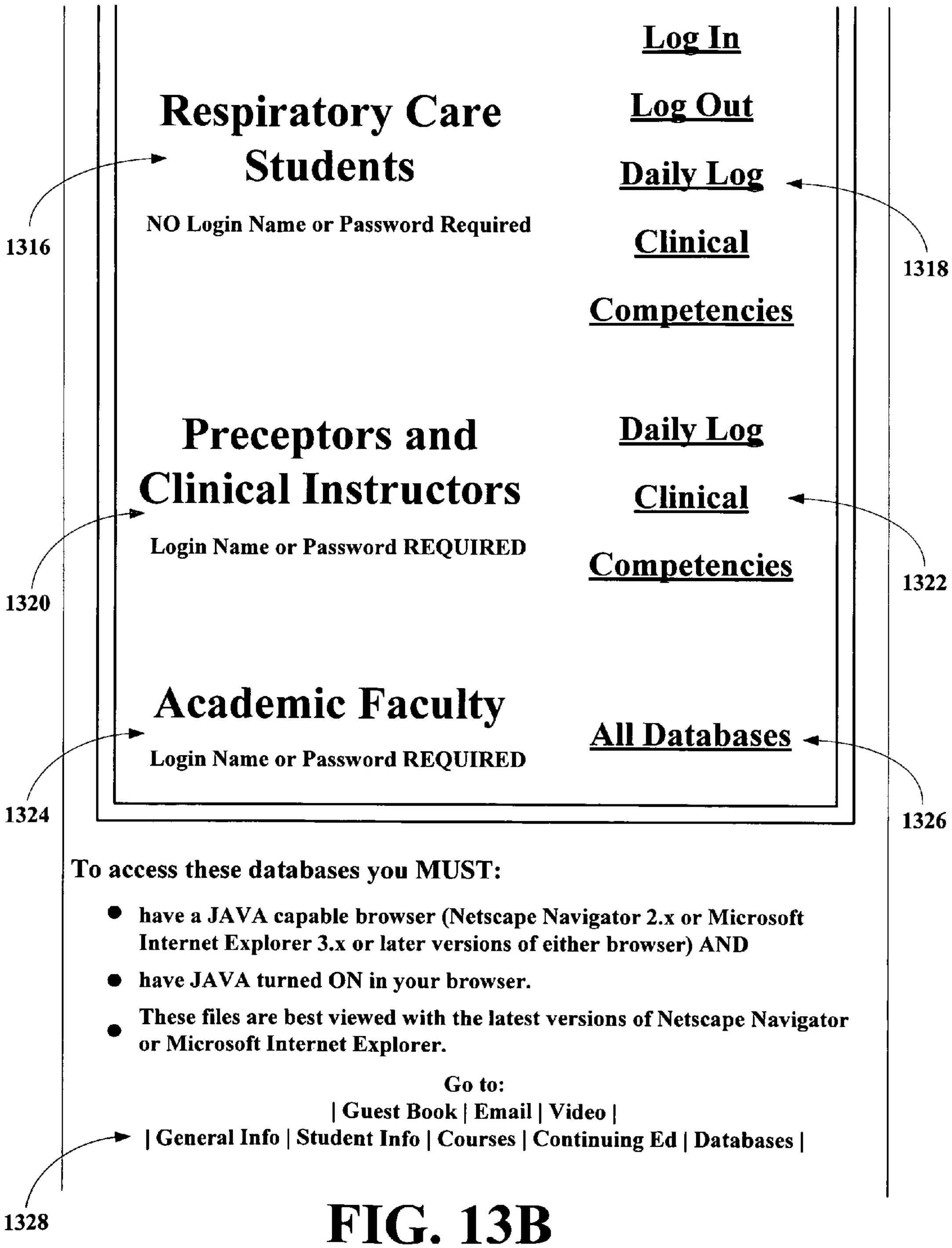
Figure 13C:
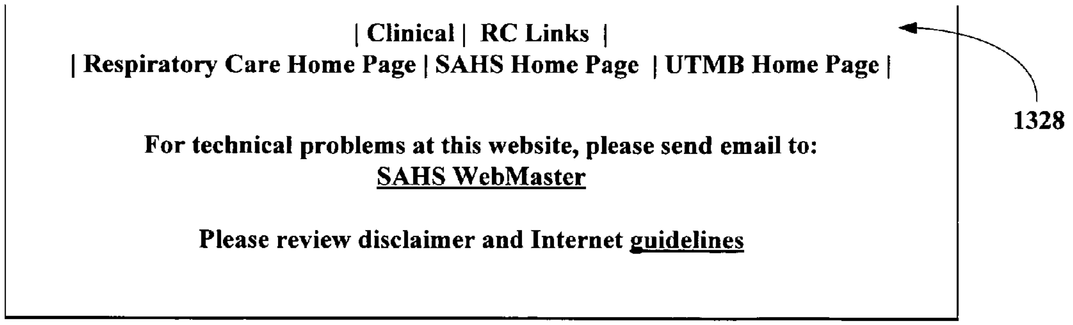

Referring now to FIGS. 13A-C, a preferred screen display 1300 for a system start process relating to a respiratory care program of the present is shown to include a window 1302. Within the window 1302, are six major subsystems: a public subsystem 1304 with corresponding function selectors 1306; a program resource surveys subsystem 1308 with corresponding function selectors 1310; a program evaluations subsystem 1312 with corresponding function selectors 1314; a students subsystem 1316 with corresponding function selectors 1318; a preceptors and clinical instructors subsystem 1320 with corresponding function selectors 1322; and an academic faculty section 1324 with accessible function selection area 1326 to all function and databases. The screen image 1300 also includes auxiliary web-links 1328 to traverse different parts of the web environment in which the system is installed. It should be recognized that these selection areas correspond to the function diagramed in FIG. 1-12. The public subsystem was not discussed previously and simply allows the public to enter as a guest and review publically available information such as AV surveys. The other subsystems were described in the previous section and the selectors correspond to the functions available to different class of users. The only subsystem not shown in this figure is staff subsystem.

Figure 14A:
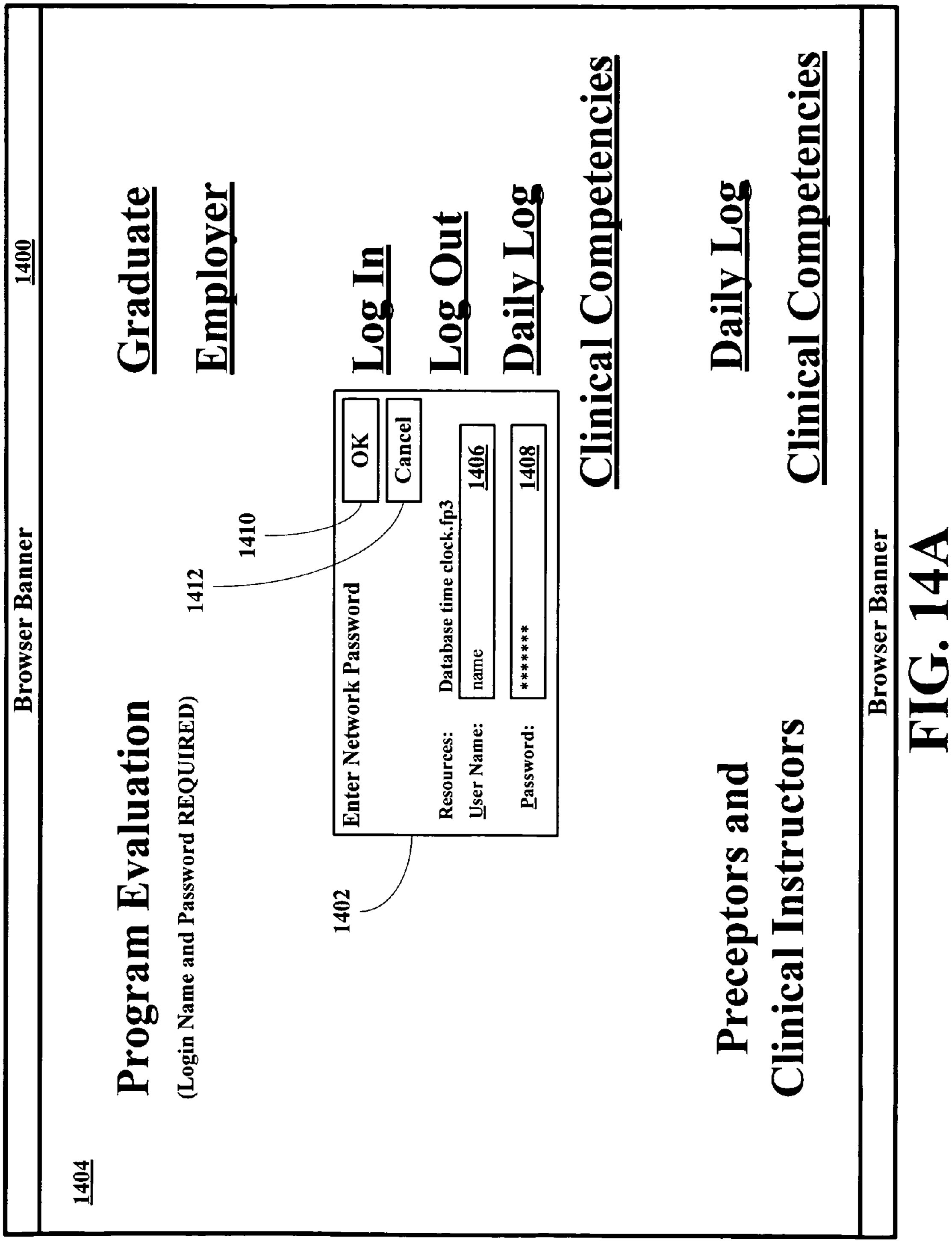
Figure 14B:
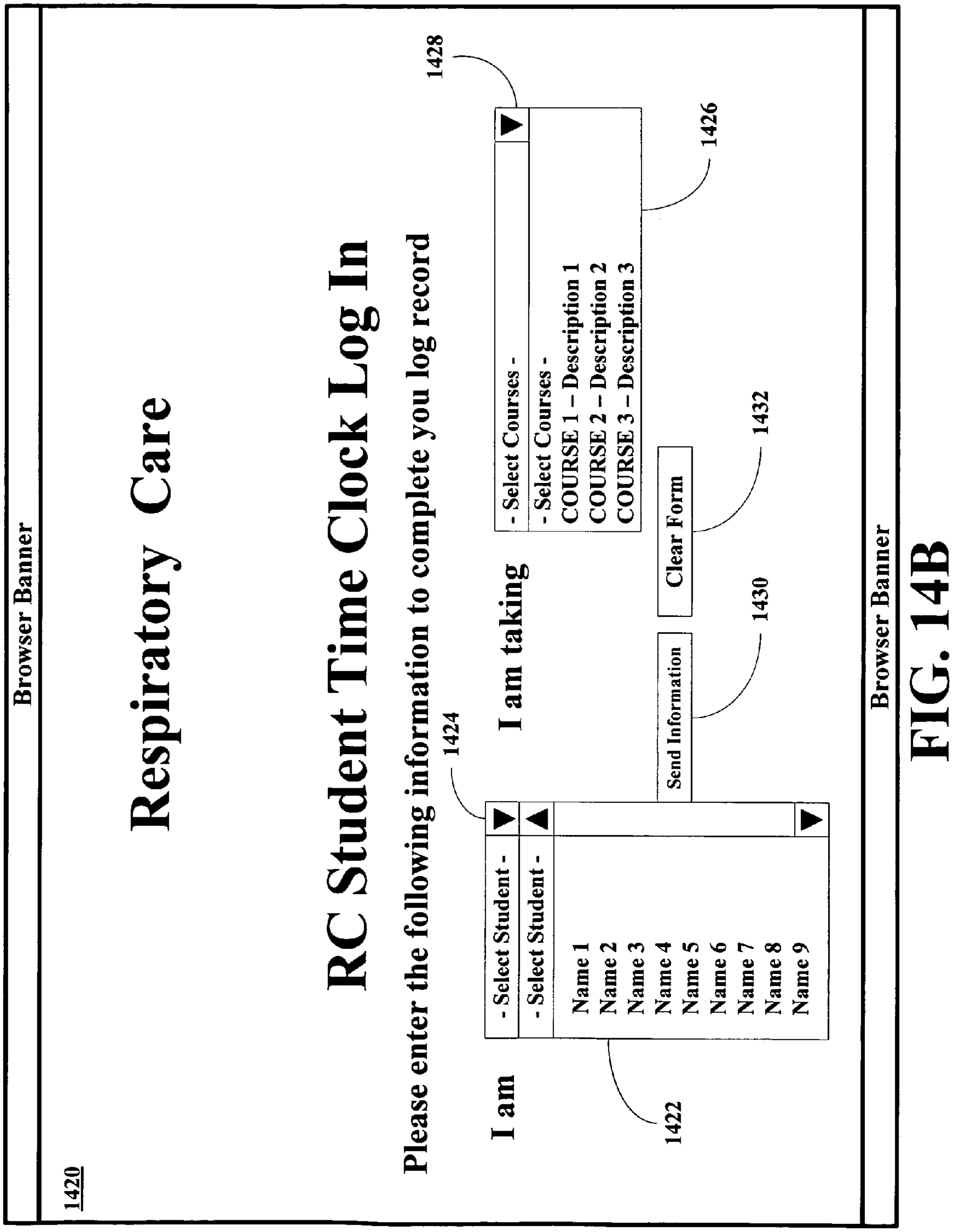
Figure 14C:
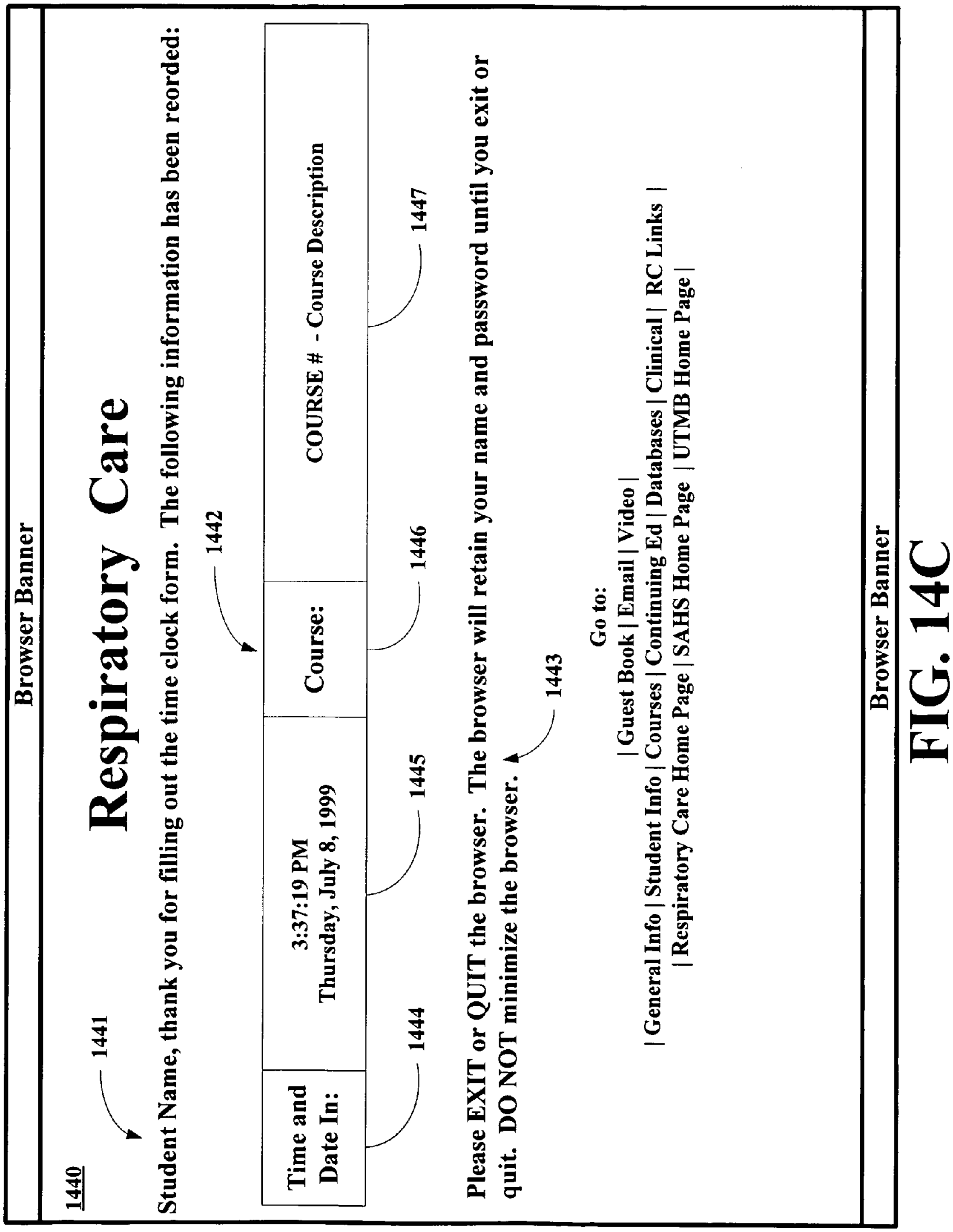
Figure 14D:
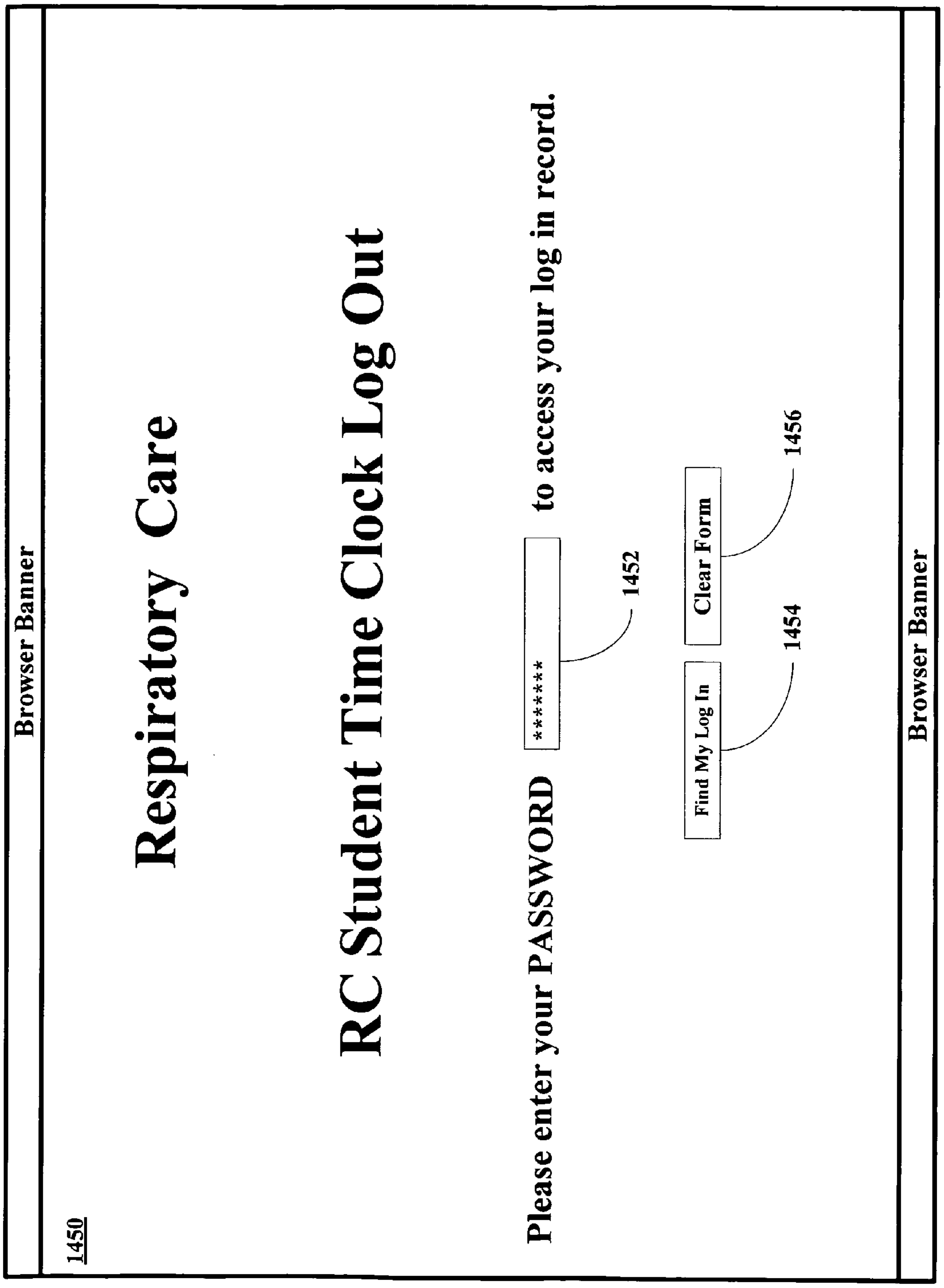

Referring now to FIGS. 14A-F, a preferred set of screen images associated with the student Time Clock functions—Time In and Time Out—is shown. Looking at FIG. 14A, an enter screen display 1400 is shown, where the student has already selected a Log In selector of FIG. 13B. The screen image 1400 includes an enter network password pop up window 1402 within a database selection window 1404, which pops up whenever a user selects a subsystem or function that requires a name and password to attain entry. The student enters his/her name in a name field 1406 and password in a password field 1408 and hits the ok button 1410. Of course, the user can abort the process by hitting the cancel button 1412. Because the system is shown here operating under a Windows operating system using Internet Explorer, internet and window icons and pull down menus are also available to the user. Once the student user enters in name and password and hits the ok button, then the system displays a student Time Clock Log In screen 1420 as shown in FIG. 14B. The Time Clock Log In screen 1420 includes a student select box 1422 and associated pull down menu 1424, which allows the user identify himself/herself and a course select box 1426 and associated pull down menu 1428, which allow the user to identify the appropriate course to which the Time Clock entry will ultimately associated. The screen 1400 also includes a send information button 1430, which submits the entry to the Time In function and a clear form button 1432, which clears the selection. Of course, the program can keep the student identity entered in the log in step allowing the student to skip the select student step. Once a completed form is submitted to the system, the Time In function outputs a confirmation screen 1440 as shown in FIG. 14C. The confirmation screen 1440 includes a student identification area 1441 with associated commentary; a summary table 1442; and a instruction comment area 1443, which tells the user how to Log Out (Exit or Quit). The box 1442 includes a time and date in labeled entry 1444, a time and date entry 1445, a course label entry 1446 and a course entry 1447. When the student exits or quits the browser or system, then the system output a Time Clock Log Out screen 1450 as shown in FIG. 14D. The Time Clock Log Out screen 1450 includes a password entry box 1452, where the student enter her/his password so that the Time Out entry can be matched to its corresponding Time In entry. The screen 1450 also includes a Find My Login button 1454, which submits the entry to the Time In function and a clear form button 1456, which clears the selection. After the student enters his/her password, the system matches the Time Out entry with its corresponding Time In entry and outputs a Time Clock Log Out identification screen 1460 as shown in FIG. 14E. The Time Clock Log Out identification screen 1460 includes an area selection box 1462 with an associated pull down menu 1464, where the student selects a hospital area where she/he performed the task and a clinician or instructor using a first name box 1466 and a last name box 1468. The screen 1460 also includes a send information button 1470, which submits the entry to the Time In function and a clear form button 1472, which clears the selection. Once the student has log out, the system outputs a Time Clock In/Out confirmation screen 1480 as shown in FIG. 14F. The confirmation screen 1480 includes a student identification area 1481 with associated commentary; a summary table 1482; and a instruction comment area 1483, which tells the user how to Log Out (Exit or Quit). The box 1482 includes a time and date in labeled entry 1484, a time and date in entry 1485, a course label entry 1486, a course entry 1487, a time and date out labeled entry 1488, a time and date out entry 1489, a location label entry 1490, a location entry 1491, a total time labeled entry 1492, a total time entry 1493, a clinical instructor label entry 1494, a instructor entry 1495.

Figure 15A:
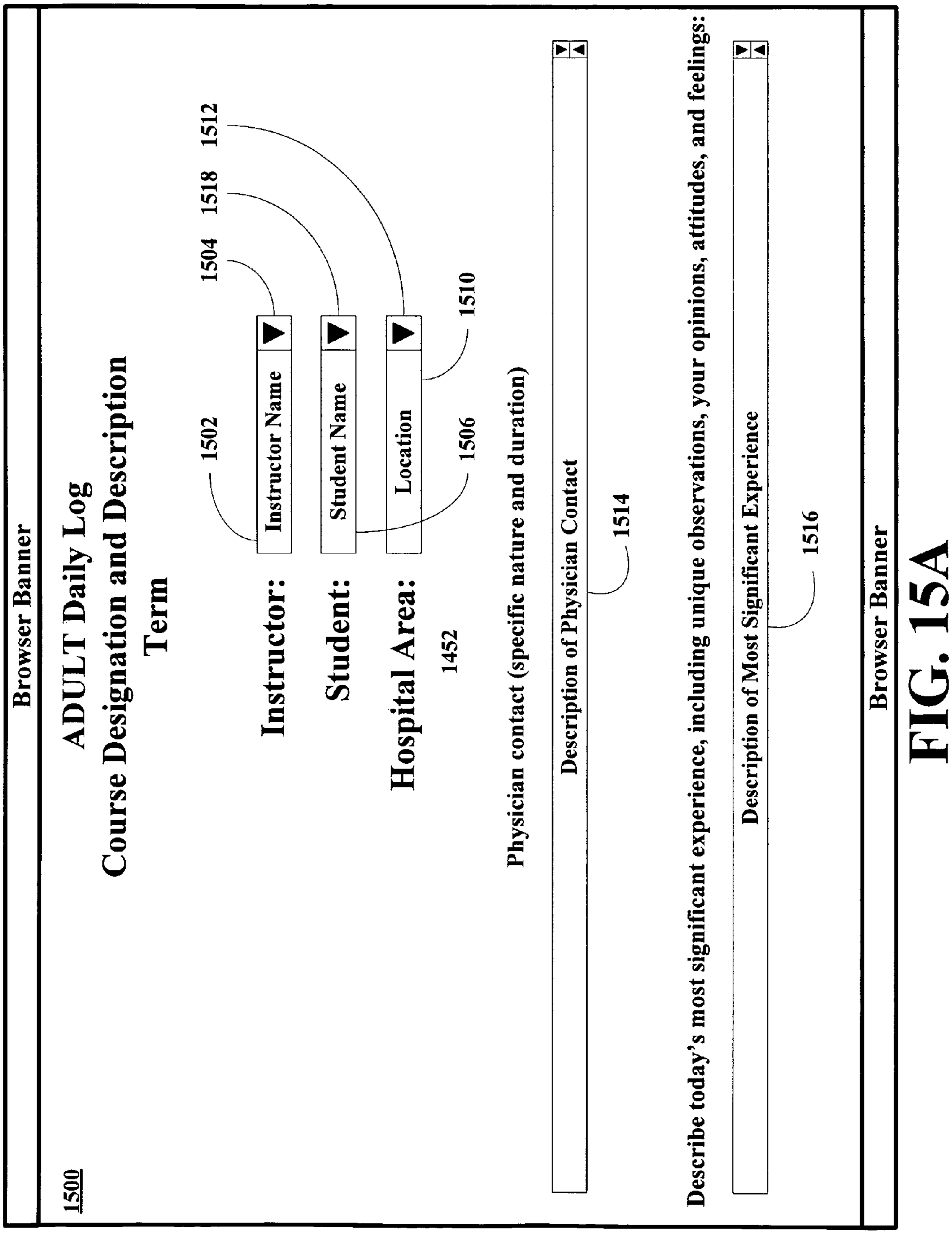
Figure 15B:
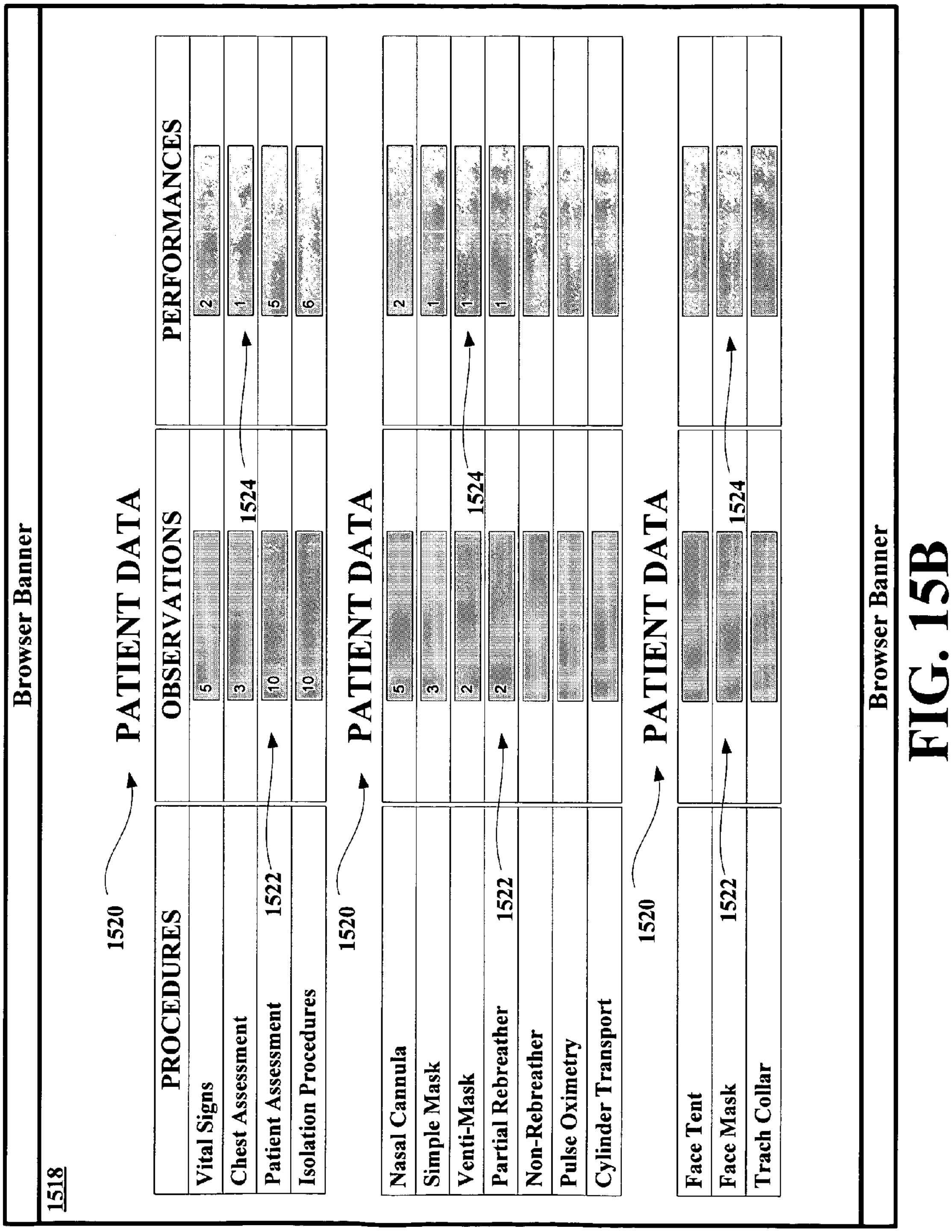
Figure 15C:
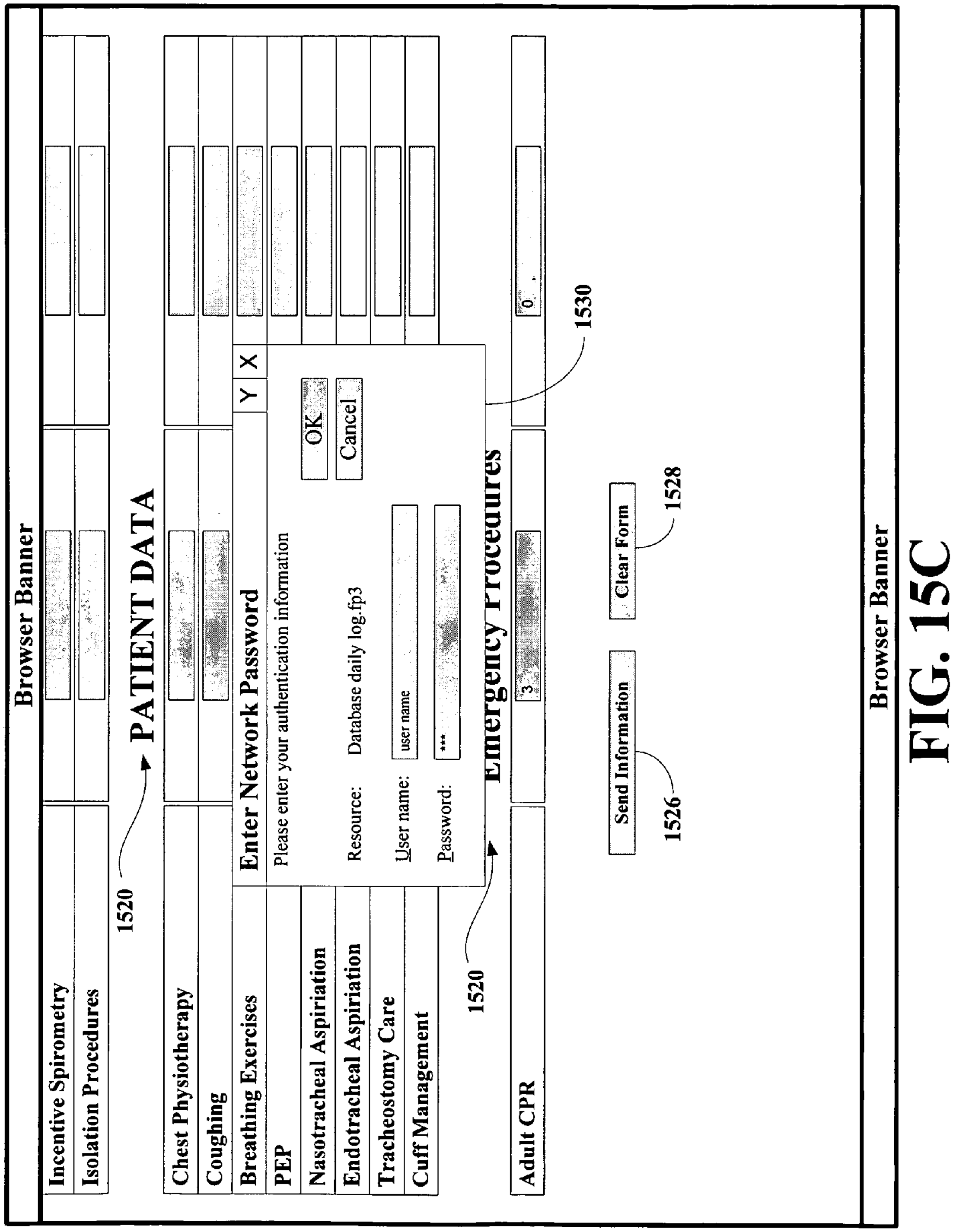

Referring now to FIGS. 15A-D, a preferred set of screen images associated with the instructor daily log function is shown for a student with validation by a clinician/instructor. Looking at FIG. 15A, an enter screen display 1500 is shown, where the student has already selected the Daily Log selector of FIG. 13B. The screen image 1500 includes an instructor identification box 1502 with associated pull down menu activation button 1504, which allows the student to identify clinician; a student identification box 1506 with associated pull down menu activation button 1508, which allows the student to identify herself/himself; and an area identification box 1510 with associated pull down menu activation button 1512, which allows the student to identify the applicable area. The image 1500 also includes a Physician contact entry box 1514, where the student enters the nature and duration of contact and a description box 1516, where the student enters any observation, opinions, attitudes or feeling. Looking at FIGS. 15B&C, the screen 1500, after scroll down with scroll bar 1518, also includes Data entry categories 1520 and associated observation fields 1522 and performance fields 1524 corresponding to the area and protocols within the area. The observation fields 1522 are filled out by the student and the performance fields 1524 are filled out by a clinician. The screen 1500 also includes a send information button 1526 and a clear form button 1528. FIG. 15C also demonstrates a clinical validating the daily log entry for the student after completion by entering the instructor's user name and password in a password pop up window 1530. After validation a confirmation screen 1532 is displayed by the system.

Figure 16A:
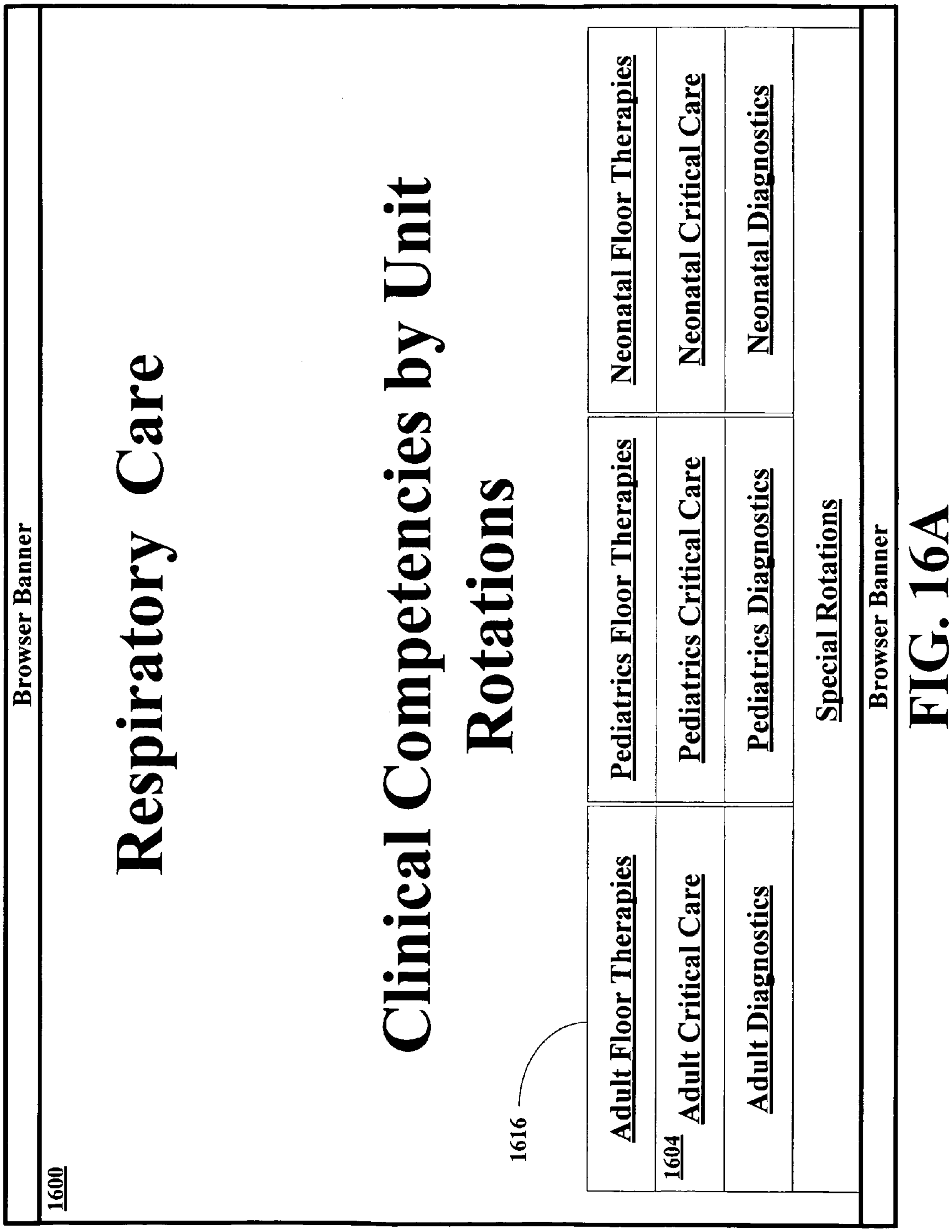

Referring now to FIGS. 16A-G, a preferred set of screen images associated with the clinical competencies function is shown for a student with validation by a clinician/instructor. Looking at FIG. 16A, a clinical competencies by unit and rotations selection screen 1600 is shown, where the student selects a particular unit and competency for a selection box 1602. For example, if the student selects the Adult Critical Care unit selector 1604, then the system outputs a adult critical care selection screen 1606 shown in FIG. 16B, which includes a therapy group column 1608 with associated therapies 1610 and a specific competency column 1612 with associated competency selectors 1614. As another example, if the student selects an Adult Floor Therapies selector 1616, then the system outputs the adult floor therapy competencies screen 1618 shown in FIG. 16C, which includes a therapy group column 1620 with associated therapies 1622 and a specific competency column 1624 with associated competency selectors 1626. Now, if the student selects the nasal cannula selector 1628 in the oxygen therapy group 1630, then the system outputs a nasal cannula data entry screen 1632 as shown in FIG. 16D. The data entry screen 1632 includes a data identification box 1634, an instructor identification box 1636, with associated pull down menu 1638 and a student identification box 1640 with associated pull down menu 1642. The data entry screen 1632 also includes a conditions description entry box 1644 and an additional comment box 1646. If the clinician is not available for immediate validation and evaluation, then the student can send the information to the database using a send information button 1648 or the student can clear the form using a clear form button 1650 as shown in FIG. 16E. If the clinician is available, then the clinician can evaluate the student's performance using a summary performance evaluation box 1652 with associated pull down menu 1654 also as shown in FIG. 16E. Once the clinician or student completes the form, then a user name/password pop up menu 1656 is displayed as shown in FIG. 16F. The system then enters the data as either validated or invalidated and displays a confirmation screen such as a clinician confirmation screen 1658 as shown in FIG. 16G.

Referring now to FIGS. 17A-H, a preferred set of screen images associated with the faculty subsystem of this invention is shown. Looking at FIG. 17A, a main faculty selection screen 1700 is shown, where the faculty member has already selected the all database selector of FIG. 13B. The screen 1700 includes selection window 1702. The selection window 1702 includes a database identification column 1704 where the accessible database are listed and an options section 1706 where options associated with each database are listed. The first four identified databases (student, clinical preceptors, daily log and competency evaluations) are shown with four options View, Add, Search, and Modify/Delete. Some of the other database only include the View and Search options. If the faculty member selects the modify/delete option for any one of the database, then the system displays a modify/delete selection screen 1720 as shown in FIG. 17B for modifying or deleting a student record. The modify/delete selection screen 1720 includes a first name field 1721, a last name field 1722, an ID field 1723, an email field 1724, an street address field 1725, a city field 1726, a state field 1727, a zip code field 1728, and a phone number field 1729. The screen 1720 also includes a student database record list pop up window 1730 for selecting a student. The screen 1720 also includes a Modify button 1731, a DELETE button 1732 and a Reset Form button 1733. Looking at FIG. 17C, a view time clock screen 1740 is shown which includes a student identification column 1741, a clinical instructor identification column 1742, a date column 1743, a time in column 1744, a time out column 1745, total time column 1746, a location column 1747 and a course column 1748. Looking at FIG. 17D, a search time clock records screen 1750 is shown which includes a student identification box 1751 with associated pull down menu activation button 1752, a clinical instructor identification box 1753 with associated pull down menu activation button 1754, a date restriction box 1755 with associated pull down menu activation button 1756 for selecting date restriction operators, a date box 1757, a location box 1758 with associated pull down menu activation button 1759, a course box 1760 with associated pull down menu activation button 1761, a send search request button 1762, and a clear form button 1763. Looking now to FIGS. 17E&F, a view screen 1765 is shown resulting from the selection of the View option for the competency evaluation database. The screen 1765 includes a student column 1766, a clinical instructor column 1767, a procedure column 1768, a location column 1769, an evaluation column 1770 and a date column 1771. If the faculty member desires to look at a given record say the record of Sputum Bowl 1772 shown highlighted in FIG. 17E, then the system outputs a screen 1773 showing the selected record. Looking now to FIGS. 17G&H, a search screen 1780 for searching the clinical competency database is shown. The screen 1780 includes a student identification box 1781 with associated pull down menu activation button 1782, a clinical instructor identification box 1783 with associated pull down menu activation button 1784, a patient identification box 1785 with associated pull down menu activation button 1786, a date restriction box 1787 with associated pull down menu activation button 1788A for selecting date restriction operators, a date box 1788B, a summary box 1789 with associated pull down menu activation button 1790, a location box 1791 with associated pull down menu activation button 1792, a therapy group box 1793 with associated pull down menu activation button 1794, a specific competency box 1795 with associated pull down menu activation button 1796, a send search request button 1797, and a clear form button 1798. Once the search has been completed, the system outputs a hit list screen 1799 as shown in FIG. 17H.

Figure 18A:
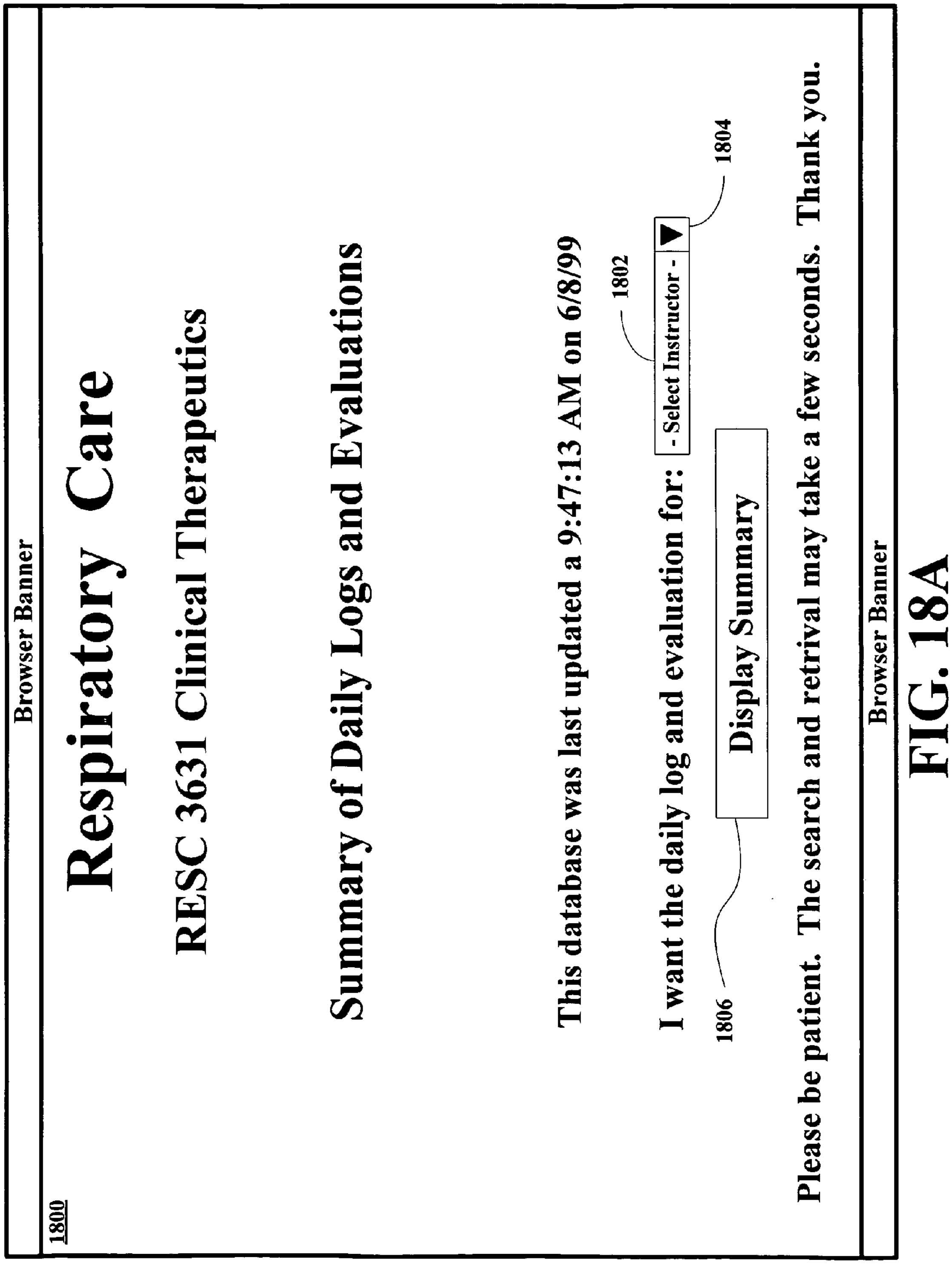
FIGS. 18A&B depicts a preferred set of screen images associated with the daily log summary function of this invention.
Figure 18B:
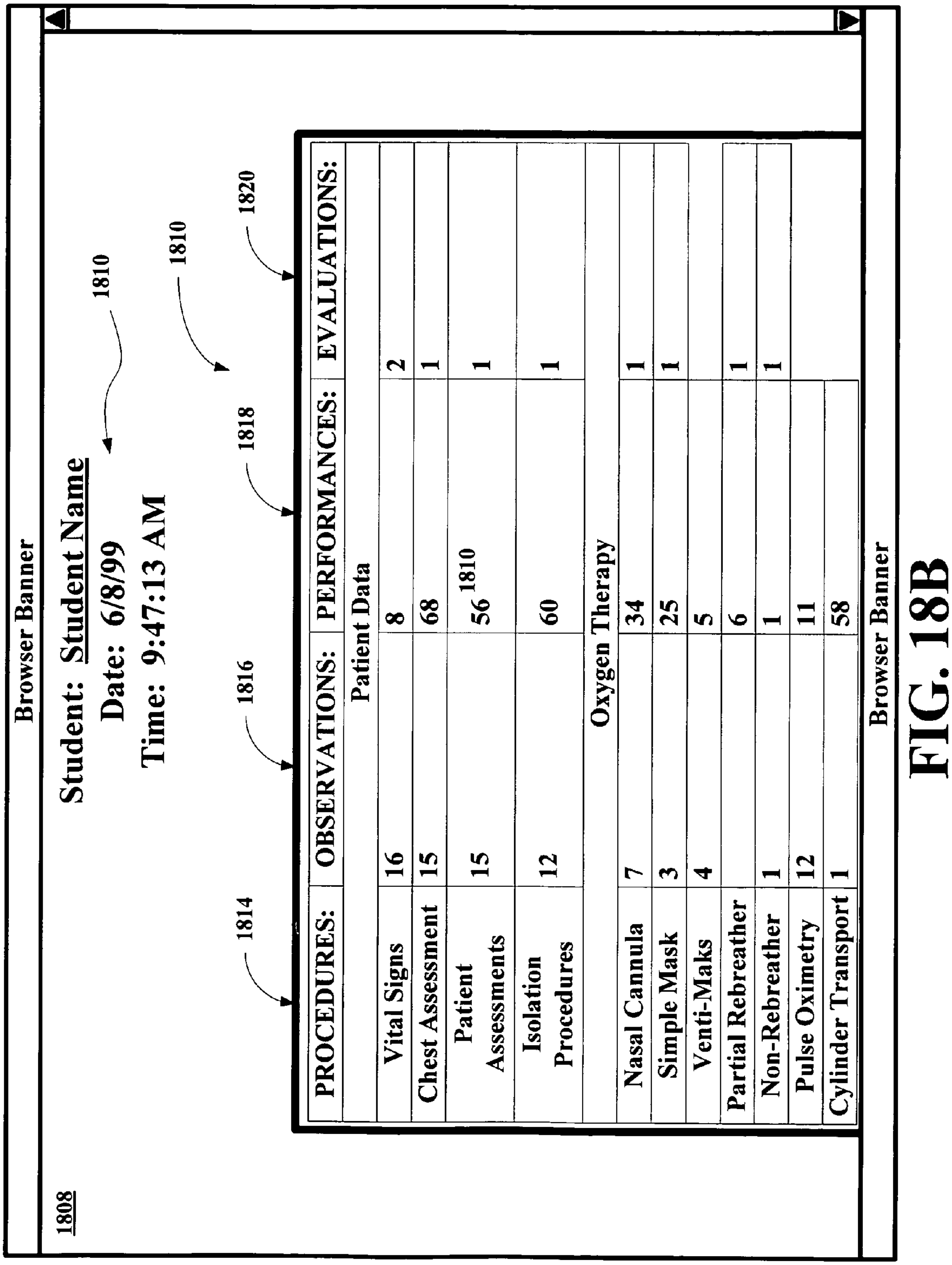

Referring now to FIGS. 18A&B, a preferred set of screen images associated with the daily log summary function is shown to include a summary of daily logs and evaluations screen 1800. The screen image 1800 includes a selection box 1802 with associated pull down menu activation button 1804, which allows the user to select a student and a display summary button 1806. Once a student is selected, the function outputs a corresponding daily log summary screen 1808 including an identification summary 1810 and a table 1812 having a procedures column 1814, an observations column 1816, a performances column 1818 and an evaluations column 1820.

Figure 19B:
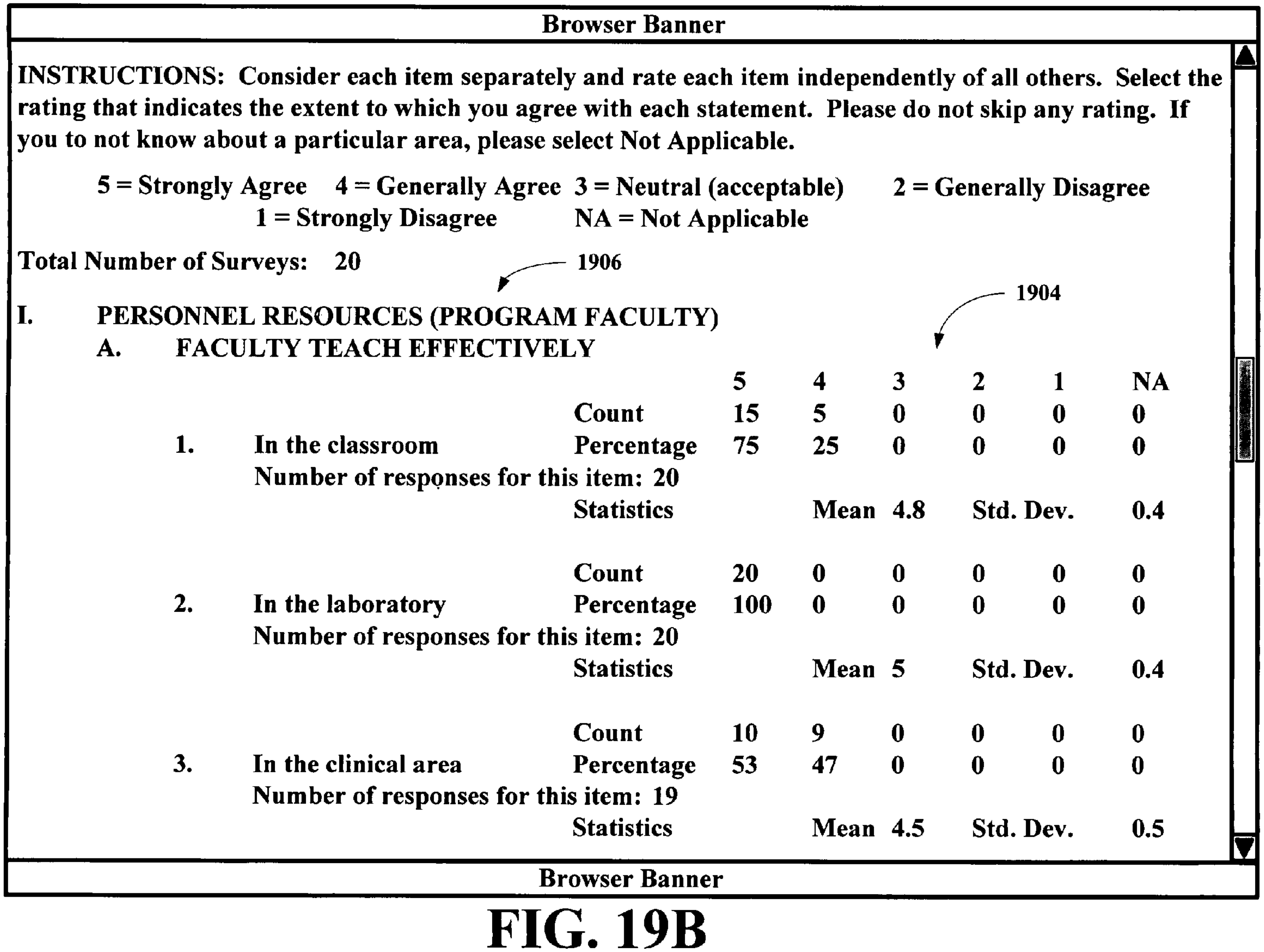
FIGS. 19A&B depicts a preferred set of screen images associated with the student program resource survey result function of the summaries subsystem of this invention.
Figure 20I:
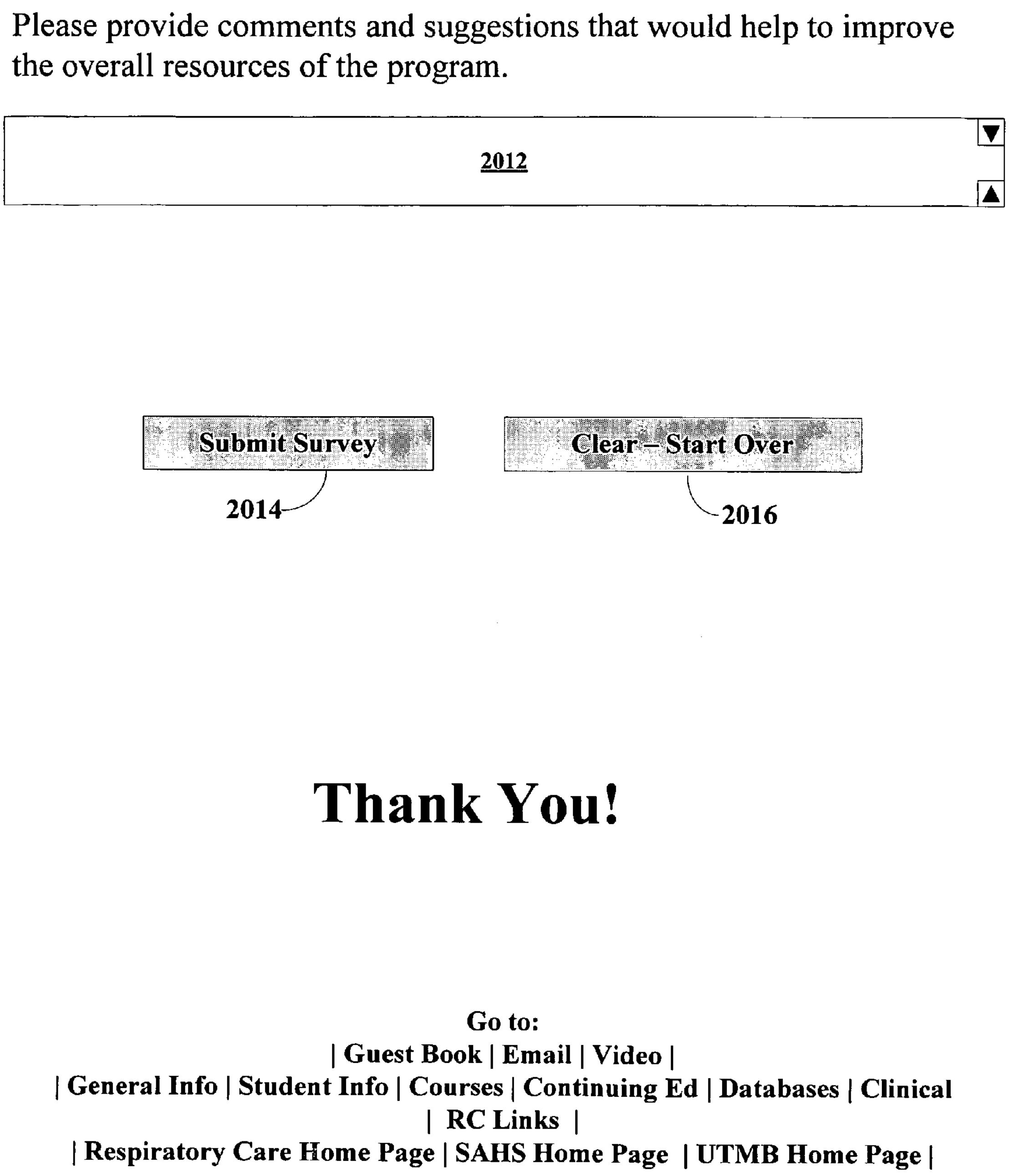

Referring now to FIGS. 19A&B, a preferred set of screen images associated with the student program resource survey result function of the summaries subsystem is shown. Looking at FIG. 19A, a survey results screen 1900, which identifies the survey results. Using a scroll control bar 1902, the user can scroll down to obtain the results and statistics 1904 associated with each survey question 1906 of the selected survey.

Referring now to FIGS. 20A-J, an example of a student program resource survey 2000 is shown. The survey 2000 includes a set of instructions 2002 and a set of identification box 2004 with associated pull down menu activation buttons 2006, which allows the student to identify herself/himself, the semester and year. The survey 2000 also includes a plurality of questions 2008 with ranked answers 2010 and a plurality of comment fields 2012. The survey 2000 also includes a send survey button 2014 and a clear-start over button 2016.

The system of the present invention is ideally suited for use on the internet where the world wide web allows students, clinicians and faculty members to be located at remote sites from each other. Thus, a user would jump on to the internet and establish contact with the server(s) on which the system of this invention resides. Once attached to the server, the user would login to the system and depending on the users name and password would be directed to the appropriate subsystems. The system of the present invention is preferably maintained on at single site which can comprise one or more servers, but the system can be implemented in a distributed form where the databases for each site reside at the site and not in a central repository. However, for security, tracking and accreditation reasons, a single site is preferred. A web based or linked system provides certain advantages for medical schools that have rotations or clinical competencies occurring in a number of different sites. A user would simply attach to the world wide web, point to the web address for the server on which the system resides and interact with the system to log his/her training session. Additionally, any authorized user can attain access from any place and perform whatever function that user would be able to perform.

Suitable computer include, without limitation, any digital processing digital process subsystems or units (DPUs) capable of being used with the present invention include, without limitation, any apparatus capable of inputting, manipulating, altering and/or changing and outputting digital and/or analog data, e.g., personal computers, laptop computers, desktop computers, palm computers, mainframe computers, minimainframe computers or any other digital and/or analog processing device that can receive data input, act on the data input via software and/or hardware and generate a corresponding output based on the input data and the internal hardware and/or software. Generally, the devices include a processing unit, a memory, e.g., on the processing unit or on electronically connected memory chips, a mass storage device, e.g., hard disks, solid state disks, tapes or the like, buses for interconnecting components, peripherals, e.g., a display, a speaker, a mouse, a keyboard, a touch pad, a eye tracking device, a VR device, or the like, communication hardware and all necessary software including the generating software of the present invention. The necessary software will generally include, without limitation, a windowing operating system, communication software, driver software for all peripherals, a database program including any well known database program, a browser such as MS Explore, NetScape, or the like or other software or the like.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. A computer server having encoded thereon a system of executable routines comprising:

a GUI subsystem of executable routines for interacting with a user including input screens having data input fields, selection fields and activation buttons and output screens including data output fields;

a database subsystem of executable routines for storing, manipulating and polling data including database fields corresponding to the input data field and output data field of the GUI screens;

a logon subsystem of executable routines including user identification routines to establish user identity and user system access status;

a survey subsystem of executable routines including a plurality of surveys;

a student subsystem of executable routines including a student time clock function, a student daily log function, a student clinical competencies function and a student personal data function;

a clinician subsystem including a clinician personal daily log function, a clinician clinical competencies function and a clinician personal data function;

a staff subsystem of executable routines including a staff personal data function; and a faculty subsystem of executable routines including a faculty personnel data function, a faculty time clock function, a faculty daily log function, a faculty clinical competencies function, a faculty summaries function and a faculty program surveys function, where the computer server is connected to a distributed computer network selected from the group of an intranet and the Internet, where the survey subsystem comprises an employer survey, a graduate survey, a student survey and a program personnel survey, where the student time clock function comprises a time in clock function, a time out clock function, a view time clock records function and a generate time clock summary function, where the time in and time out functions create a unique time stamp for time in and time out and an elapsed time tied to a particular clinician and hospital or associated with a given medical protocol, procedure or rotation, where the student daily log and student clinical competencies function comprise a view records function, a search records function, an add record function and summary function, where the staff personal data function comprises a view records function, a search records function, an add record function, a modify record function, and a delete record function, and where the clinician personal daily log function and clinician clinical competencies function comprises a validate student records function.

2. The system of claim 1, wherein the computer server is a computer server dedicated to entering, tracking and verifying medical student and/or medical staff patient and procedure activities.

3. The system of claim 1, wherein the network is the Internet and the system is web-based via the computer server.

4. A method implemented on a distributed computer network for entering student medical competency data comprising the step of:

providing a computer server having encoded thereon a system comprising:

a GUI subsystem of executable routines for interacting with a user including input screens having data input fields, selection fields and activation buttons and output screens including data output fields;

a database subsystem of executable routines for storing, manipulating and polling data including database fields corresponding to the input data field and output data fields of the GUI screens;

a logon subsystem of executable routines including user identification routines to establish user identity and user system access status;

a survey subsystem of executable routines including a plurality of surveys;

a student subsystem of executable routines including a student time clock function, a student daily log function, a student clinical competencies function and a student personal data function;

a clinician subsystem including a clinician personal daily log function, a clinician clinical competencies function and a clinician personal data function;

a staff subsystem of executable routines including a staff personal data function; and a faculty subsystem of executable routines including a faculty personnel data function, a faculty time clock function, a faculty daily log function, a faculty clinical competencies function, a faculty summaries function and a faculty program surveys function, where the network is an intranet or the Internet, where the survey subsystem comprises an employer survey, a graduate survey, a student survey and a program personnel survey, where the student time clock function comprises a time in clock function, a time out clock function, a view time clock records function and a generate time clock summary function, where the time in and time out functions create a unique time stamp for time in and time out and an elapsed time tied to a particular clinician and hospital or associated with a given medical protocol, procedure or rotation, where the student daily log and student clinical competencies function comprise a view records function, a search records function, an add record function and summary function, where the staff personal data function comprises a view records function, a search records function, an add record function, a modify record function, and a delete record function, and where the clinician personal daily log function and clinician clinical competencies function comprises a validate student records function logging onto the system using the logon subsystem;

selecting a time in function which generates a unique time in stamp;

selecting a time out function after completion of a medical protocol or procedure which generates a unique time out stamp;

selecting a clinician and an area identifying an instructor and the protocol or procedure;

entering data associated with the protocol or procedure in appropriate fields in a GUI screen associated with the protocol or procedure, and updating the time entry record.

5. The method of claim 4, further comprising the steps of:

submitting the protocol data to the database after review by a supervisor and polling the entered data.

6. The method of claim 4, wherein the computer server is a computer server connected to the network and dedicated to performing the method of claim 4.

7. The method of claim 4, wherein the network is the Internet and the system is web-based.

8. A method for documenting medical professional competency and accrediting medical schools comprising the steps of:

retrieving medical student data for each medical student from a computer server having encoded thereon a system comprising:

a GUI subsystem of executable routines for interacting with a user including input screens having data input fields, selection fields and activation buttons and output screens including data output fields;

a database subsystem of executable routines for storing, manipulating and polling data including database fields corresponding to the input data field and output data field of the GUI screens;

a logon subsystem of executable routines including user identification routines to establish user identity and user system access status;

a survey subsystem of executable routines including a plurality of surveys;

a student subsystem of executable routines including a student time clock function, a student daily log function, a student clinical competencies function and a student personal data function;

a clinician subsystem including a clinician personal daily log function, a clinician clinical competencies function and a clinician personal data function;

a staff subsystem of executable routines including a staff personal data function; and a faculty subsystem of executable routines including a faculty personnel data function, a faculty time clock function, a faculty daily log function, a faculty clinical competencies function, a faculty summaries function and a faculty program surveys function, where the network is an intranet or the Internet, where the survey subsystem comprises an employer survey, a graduate survey, a student survey and a program personnel survey, where the student time clock function comprises a student time in clock function, a student time out clock function, a student view time clock records function and a student generate time clock summary function, where the time in and time out functions create a unique time stamp for time in and time out and an elapsed time tied to a particular clinician and hospital or associated with a given medical protocol, procedure or rotation, where the student daily log and student clinical competencies function comprise a student view records function, a student search records function, a student add record function and student summary function, where the staff personal data function comprises a staff view records function, a staff search records function, a staff add record function, a staff modify record function, and a staff delete record function, and where the clinician personal daily log function and clinician clinical competencies function comprises a clinician validate student records function; and determining an accreditation score therefrom.

9. The method of claim 8, further comprising the steps of:

retrieving medical staff data for each medical staff from the system; and determining an institution or department accreditation score therefrom.

* * * * *